US010905401B2

(12) United States Patent
Li et al.

(10) Patent No.: US 10,905,401 B2
(45) Date of Patent: Feb. 2, 2021

(54) ULTRASOUND IMAGING WITH SPECTRAL COMPOUNDING FOR SPECKLE REDUCTION

(71) Applicant: The Board of Trustees of the Leland Stanford Junior University, Stanford, CA (US)

(72) Inventors: Yilei Li, Palo Alto, CA (US); Steven Chu, Menlo Park, CA (US)

(73) Assignee: The Board of Trustees of the Leland Stanford Junior University, Stanford, CA (US)

(*) Notice: Subject to any disclaimer, the term of this patent is extended or adjusted under 35 U.S.C. 154(b) by 0 days.

(21) Appl. No.: 16/029,254

(22) Filed: Jul. 6, 2018

(65) Prior Publication Data

US 2019/0008485 A1    Jan. 10, 2019

Related U.S. Application Data

(60) Provisional application No. 62/530,241, filed on Jul. 9, 2017.

(51) Int. Cl.
*A61B 8/08*    (2006.01)
*A61B 8/14*    (2006.01)
*A61B 8/00*    (2006.01)

(52) U.S. Cl.
CPC ............ *A61B 8/5269* (2013.01); *A61B 8/145* (2013.01); *A61B 8/4488* (2013.01); *A61B 8/461* (2013.01); *A61B 8/5207* (2013.01); *A61B 8/5253* (2013.01)

(58) Field of Classification Search
CPC ... A61B 8/5269; A61B 8/5253; A61B 8/4488; A61B 8/5207; A61B 8/461; A61B 8/145;
(Continued)

(56) References Cited

U.S. PATENT DOCUMENTS 3,987,673 A    10/1976    Hansen
4,016,750 A *  4/1977    Green ..................... A61B 8/08
                                                      73/629
(Continued)

FOREIGN PATENT DOCUMENTS

WO    WO 99/040847    8/1999

OTHER PUBLICATIONS

Magnin ["Frequency Compounding for Speckle Contrast Reduction in Phased Array Images", Ultrasonic Imaging 4, 267-281 (1982)]. (Year: 1982).*
(Continued)

*Primary Examiner* — Oommen Jacob
(74) *Attorney, Agent, or Firm* — Kilpatrick Townsend & Stockton LLP

(57) ABSTRACT

Ultrasound imaging systems and methods with frequency (spectral) compounding for speckle reduction are disclosed. In one aspect, an ultrasound imaging system includes a transducer probe with interleaved transmit and receive arrays. The system may utilize ultrasound pulses having an optimized time-bandwidth product. In one aspect, a transducer probe with separate transmit and receive elements can enable transmission and reception of multiple ultrasound pulses, each centered at a different frequency, during the time of one A-scan. Thus, such a system can capture multiple independent speckle images without reducing overall B-mode framerate. In another aspect, the system may transmit a broadband pulse and may obtain separate speckle images by filtering the received echo using multiple spectral filters. The system may compound multiple images captured at different frequencies to provide speckle reduction. The ultrasound imaging system further includes a processor configured to generate an ultrasound image based on the echoes.

20 Claims, 32 Drawing Sheets

(58) Field of Classification Search
CPC .. A61B 8/481; A61B 8/06; A61B 8/08; A61B 8/4494; A61B 8/085; A61B 8/488
USPC ......................................... 600/447, 444, 437
See application file for complete search history.

(56) References Cited

U.S. PATENT DOCUMENTS

| | | | | |
|---|---|---|---|---|
| 4,478,085 | A * | 10/1984 | Sasaki | G01S 7/52025 367/155 |
| 4,817,617 | A | 4/1989 | Takeuchi et al. | |
| 5,261,280 | A * | 11/1993 | Matzuk | G01S 7/52025 600/454 |
| 5,575,290 | A * | 11/1996 | Teo | G01S 15/8925 600/456 |
| 5,577,505 | A | 11/1996 | Brock-Fisher et al. | |
| 5,601,086 | A | 2/1997 | Pretlow, III et al. | |
| 5,632,277 | A | 5/1997 | Chapman et al. | |
| 5,653,235 | A | 8/1997 | Teo | |
| 5,696,737 | A * | 12/1997 | Hossack | G01N 29/2462 367/138 |
| 5,697,372 | A * | 12/1997 | Hughes | G01S 7/5205 600/441 |
| 5,736,642 | A | 4/1998 | Yost et al. | |
| 5,833,613 | A | 11/1998 | Averkiou et al. | |
| 5,879,303 | A | 3/1999 | Averkiou et al. | |
| 5,903,516 | A | 5/1999 | Greenleaf et al. | |
| 5,957,852 | A | 9/1999 | Hossack et al. | |
| 5,991,239 | A | 11/1999 | Fatemi-Booshehri et al. | |
| 5,999,639 | A * | 12/1999 | Rogers | B25J 15/04 382/132 |
| 6,137,898 | A * | 10/2000 | Broussard | B25J 15/04 382/132 |
| 6,139,501 | A | 10/2000 | Roundhill et al. | |
| 6,401,539 | B1 * | 6/2002 | Langdon | G01N 29/06 73/609 |
| 6,440,075 | B1 | 8/2002 | Averkiou | |
| 6,494,839 | B1 | 12/2002 | Averkiou | |
| 6,530,885 | B1 | 3/2003 | Entrekin et al. | |
| 6,537,220 | B1 | 3/2003 | Friemel et al. | |
| 6,544,182 | B2 * | 4/2003 | Averkiou | G01S 7/52038 600/455 |
| 6,638,230 | B2 | 10/2003 | Brock-Fisher et al. | |
| 6,827,685 | B2 * | 12/2004 | Lin | G01S 7/52046 600/437 |
| 7,391,872 | B2 * | 6/2008 | Pompei | B06B 1/0292 367/119 |
| 7,682,309 | B2 * | 3/2010 | Ji | G03B 42/06 600/437 |
| 8,708,913 | B2 * | 4/2014 | Yamamoto | G01S 7/52046 600/443 |
| 9,465,009 | B2 * | 10/2016 | Tsuruno | G01N 29/52 |
| 2002/0040188 | A1 * | 4/2002 | Averkiou | G01S 7/52095 600/458 |
| 2003/0055337 | A1 * | 3/2003 | Lin | G01S 15/8915 600/459 |
| 2004/0054284 | A1 | 3/2004 | Cai et al. | |
| 2004/0087857 | A1 | 5/2004 | Napolitano et al. | |
| 2004/0267129 | A1 | 12/2004 | Angelsen et al. | |
| 2007/0083109 | A1 | 4/2007 | Ustuner et al. | |
| 2008/0132791 | A1 * | 6/2008 | Hastings | G01S 15/8954 600/447 |
| 2008/0194958 | A1 | 8/2008 | Lee et al. | |
| 2008/0199063 | A1 * | 8/2008 | O'Halloran | G01R 33/4824 382/131 |
| 2008/0249417 | A1 | 10/2008 | Averkiou et al. | |
| 2009/0112090 | A1 * | 4/2009 | Yamamoto | G01S 7/52046 600/445 |
| 2010/0268083 | A1 * | 10/2010 | McLaughlin | G01S 15/8954 600/443 |
| 2011/0224551 | A1 * | 9/2011 | Barnard | A61B 8/56 600/445 |
| 2011/0301466 | A1 | 12/2011 | Wang et al. | |
| 2012/0095699 | A1 | 4/2012 | Angelsen et al. | |
| 2014/0066767 | A1 | 3/2014 | Mammone et al. | |
| 2015/0151142 | A1 | 6/2015 | Tyler et al. | |
| 2015/0366542 | A1 * | 12/2015 | Brown | A61B 8/5207 600/447 |
| 2016/0140738 | A1 | 5/2016 | Asaka et al. | |
| 2016/0262729 | A1 * | 9/2016 | Srinivasan | A61B 8/5269 |
| 2017/0074978 | A1 * | 3/2017 | Miller | G01S 7/5208 |
| 2017/0209121 | A1 * | 7/2017 | Davis, Sr. | B06B 1/0622 |
| 2018/0192194 | A1 * | 7/2018 | Pompei | H03F 3/183 |
| 2019/0008485 | A1 * | 1/2019 | Li | A61B 8/4488 |

OTHER PUBLICATIONS

Berson, M., et al., "Compound Scanning with an Electrically Steered Beam", Laboratoire de Biophysique Medicale, *Ultrasonic Imaging 3*, pp. 303-308, 1981.

Choi, Myoung Hwan, et al., "Spatial Compounding of Ultrasonic Diagnostic Images for Rotating Linear Probe with Geometric Parameter Error Compensation", *Journal of Electrical Engineering and Technology*, pp. 742-749, 2014.

Choudry, Sabina, et al., "Comparison of Tissue Harmonic Imaging with Conventional US in Abdominal Disease", Imaging and Therapeutic Technology, vol. 20, No. 4, pp. 1127-1135, 2000.

Fatemi, Mostafa, et al., "Ultrasound-Stimulated Vibro-Acoustic Spectrography", *Science*, vol. 280, pp. 82-85, Apr. 3, 1998.

Gehlbach, Steve M., et al., "Frequency Diversity Speckle Processing," Ultarsonic Imaging 9, 92-105, 1987.

Liba, Orly, et al., "Speckle-Free Coherence Tomography of Turbid Media", pp. 1-55, Aug. 2016.

Liba, O, et al., "Speckle-modulating optical coherence tomography in living mice and humans," Nature Communications 8, Article No. 15845, Jun. 20, 2017.

Klimonda, Z., et al., "Spatial and Frequency Compounding in Application to Attenuation Estimation in Tissue," Archives of Acoustics, vol. 39, No. 4, pp. 519-527, 2014.

Magnin, P.A. et al., "Frequency Compounding for Speckle Contrast Reduction in Phased Array Images," Ultrasonic Imaging 4, 267-281 (1982).

Melton, H.E., et al., "A-Mode Speckle Reduction with Compound Frequencies and Compound Bandwidths", *Ultrasonic Imaging 6*, pp. 159-173, 1984.

PCT Invitation to Pay Additional Fees and, Where Applicable, Protest Fee, dated Sep. 11, 2018 in International Application No. PCT/US18/41134.

Shattuck, David P., et al., "Compound Scanning with a Phased Array", Department of Biomedical Engineering, *Ultrasonic Imaging 4*, pp. 93-107, 1982.

Trahey, G.E., et al., "A Quantitative Approach to Speckle Reduction via Frequency Compounding", *Ultrasonic Imaging 8*, pp. 151-164, 1986.

Trahey, G.E., et al., "Speckle Pattern Changes with Varying Acoustic Frequency: Experimental Measurement and Implications for Frequency Compounding," *IEEE 1986 Ultrasonics Symposium*, pp. 815.

PCT International Search Report and Written Opinion dated Aug. 23, 2018 in PCT Application No. PCT/US18/41134, 20 pages.

\* cited by examiner

ULTRASOUND IMAGING WITH SPECTRAL COMPOUNDING FOR SPECKLE REDUCTION

RELATED APPLICATIONS

This application claims the benefit of U.S. Provisional Patent Application No. 62/530,241, filed Jul. 9, 2017, entitled "SPECKLE SUPPRESSION IN ULTRASOUND IMAGING BY SPECTRAL COMPOUNDING," the contents of which are hereby incorporated by reference herein in their entirety and for all purposes.

BACKGROUND

Technological Field

The disclosed technology relates to spectral compounding in ultrasound imaging.

Description of the Related Technology

Ultrasound imaging is an increasingly important tool for diagnostic imaging with many desirable characteristics. Ultrasound imaging is used to image internal structures of a patient, such as muscles, blood vessels, organs, and to diagnose (or exclude) various diseases and conditions. Ultrasound imaging is widely used on pregnant women to monitor healthy growth of fetuses in utero.

Ultrasound waves are sound waves with frequencies above the audible range of humans, which generally extends up to about 20 kilohertz (kHz). Ultrasonic images are generated by sending ultrasound pulses into tissue of a patient (or other object being imaged) using an ultrasonic emitter or transducer. The ultrasound pulses reflect or echo off of the tissue. An ultrasound receiver or transducer receives the echoes and processes them into an image that provides useful information about the patient's tissues. A common type of ultrasound image is a B-mode image. A B-mode image illustrates the acoustic impedance of a two-dimensional cross-section of the tissue being imaged. The acoustic impedance of tissue is a linear elastic property given by the product of the density and velocity of sound in the tissue.

Ultrasound imaging has several advantages over other forms of medical imaging as it is relatively fast, provides real-time imaging, has a low cost, and does not expose patients to ionizing radiation such as would be the case with x-ray diagnostics. However, ultrasound imaging methods and systems can suffer from the presence of significant speckle noise (e.g., significant and widespread background noise in ultrasound images due to back-scattering of sound by the tissue being imaged), and useful resolution of ultrasound imaging in clinical practice can be degraded.

SUMMARY OF CERTAIN INVENTIVE ASPECTS

The innovations described in the claims each have several aspects, no single one of which is solely responsible for its desirable attributes. Without limiting the scope of the claims, some prominent features of this disclosure will now be briefly described.

One aspect of this disclosure is a method of ultrasound imaging with frequency compounding for speckle reduction. The method includes transmitting, from a transducer array, N ultrasound pulses each having a different center frequency into a medium being imaged during a round trip time for a first pulse of the N ultrasound pulses, where the round trip time for the first pulse is time for the first pulse to propagate from a transducer array to the medium and to propagate from the medium to the transducer array, wherein N is a positive integer that is greater than one. The method also includes receiving, with the transducer array, echoes of the Nultrasound pulses from the medium; generating a plurality of images from the received echoes, where each of the images is formed from an echo associated with a particular pulse of the N ultrasound pulses; and frequency compounding, with a processing circuit, the images so as to generate a plurality of frequency-compounded ultrasound images.

In the method, the transmitting can be performed with a first linear transducer array of the transducer array and the receiving can be performed with a second linear array of the transducer array.

In the method, the transmitting and the receiving can be performed at least partly concurrently.

In the method, the first linear array can be interleaved with the second linear array.

In the method, the N ultrasound pulses propagate along a line scan.

In the method, the transmitting of the N ultrasound pulses includes chirping the N ultrasound pulses.

In the method, the generating of the frequency-compounded ultrasound images can include frequency filtering the received echoes and compensating for time delays of the N ultrasound pulses.

The method can further include generating a B-mode ultrasound image based on the frequency compounded images from a plurality of line scans and visually displaying the B-mode ultrasound image.

In the method, the B-mode ultrasound image has a frame rate of at least 10 Hertz.

In the method, the Nultrasound pulses can include three consecutive pulses with increasing center frequencies.

In the method, the images formed from the echoes and the frequency-compounded ultrasound images have a transverse resolution at least partially defined by properties of the transducer array and have an axial resolution at least partially defined by pulse durations of the Nultrasound pulses. Transmitting, from the transducer array, the Nultrasound pulses can include transmitting N ultrasound pulses with pulse durations short enough that the axial resolution is within 10% of the transverse resolution.

Another aspect of this disclosure is an ultrasound system for generating frequency compounded ultrasound images with reduced speckle. The ultrasound system includes a first phased transducer array configured to transmit a plurality of ultrasound pulses having different respective center frequencies into a medium being imaged, where the first phased transducer array can include a plurality of transmitting elements; a second phased transducer array configured to receive ultrasound echoes associated with the ultrasound pulses from the medium, where the second phased transducer array can include a plurality of receiving elements and where the transmitting elements of the first phased transducer array are interleaved with the receiving elements of the second phased transducer array; and a processing circuit in communication with the second phased transducer array, the processing circuit configured to generate frequency compounded images based on the received echoes.

In the ultrasound system, the first phase transducer array can be configured to transmit the ultrasound pulses during a round trip time for a first pulse of the ultrasound pulses.

In the ultrasound system, the ultrasound system can be configured to perform a line scan.

In the ultrasound system, the ultrasound system can be configured to perform a plurality of line scans and the processing circuit can be configured to generate a B-mode image based on frequency compounded images associated with the line scans.

The ultrasound system can further include a display configured to visually present the B-mode image.

In the ultrasound system, the transmitting elements of the first phased transducer array can be configured to receive excitation signals having configurable phase delays so as to provide transmit focusing and the processing circuit can be configured to implement receive focusing.

Another aspect of this disclosure is a method of ultrasound imaging with frequency compounding for speckle reduction. The method includes applying a drive signal to a transducer array so as to excite the transducer array and compensate for a frequency response of the transducer array; transmitting a broadband ultrasound signal in a medium being imaged, where the applying causes the transmitted broadband ultrasound signal to have a flattened spectrum across a bandwidth of the transducer array; receiving echoes of the broadband ultrasound signal from the medium; frequency filtering, with a plurality of digital filters, the received echoes to produce a plurality of ultrasound images; and generating a frequency-compounded ultrasound image by compounding the ultrasound images.

The method can also include generating a plurality of additional frequency-compounded ultrasound images, forming a B-mode scan from the additional frequency compounded ultrasound images and the frequency-compounded ultrasound image, and outputting a representation of the B-mode scan.

In the method, the transmitting of the broadband ultrasound signal can include transmitting the broadband ultrasound signal with a phased array that focuses the broadband ultrasound signal on at least one voxel within the medium being imaged.

In the method, the receiving of the echoes can include receiving the echoes with a phased array configured to focus on at least one voxel within the medium being imaged.

In the method, the transmitting of the broadband ultrasound signal can include transmitting the broadband ultrasound signal with a first phased array that focuses the broadband ultrasound signal at a least one voxel within the medium being imaged and the receiving of the echoes can include receiving the echoes with a second phased array configured to focus on at least one voxel within the medium being imaged.

In the method, the first and second phased array can each include a plurality of array elements and the array elements of the first phased array can be interleaved with the array elements of the second phased array.

In the method, the frequency-compounded ultrasound image can be a nonlinear ultrasound image.

Another aspect of this disclosure is a method of ultrasound imaging with frequency compounding for speckle reduction. The method can include transmitting a broadband ultrasound signal in a medium being imaged, where the transmitting of the broadband ultrasound signal can include applying a drive signal to a transducer so as to excite the transducer and compensate for a frequency response of the transducer such that the broadband ultrasound signal has a substantially flat spectrum; transmitting a broadband ultrasound signal in a medium being imaged, where the applying causes the transmitted broadband ultrasound signal to have a flattened spectrum across a bandwidth of the transducer array; receiving echoes of the broadband ultrasound signal from a plurality of depths within the medium; frequency filtering, with a plurality of digital filters, the received echoes to produce a plurality of A-scan speckle images; and generating an A-scan frequency-compounded ultrasound image by compounding the A-scan speckle images together.

The method can also include repeating the transmitting, receiving, frequency filtering, and generating steps to generate a plurality of A-scan frequency-compounded ultrasound images and combining the plurality of A-scan frequency-compounded ultrasound images to form a B-mode frequency-compounded ultrasound image of the medium being imaged.

In the method, the transmitting of the broadband ultrasound signal can include transmitting the broadband ultrasound signal with a phased array that focuses the broadband ultrasound signal at a least one voxel within the medium being imaged.

In the method, the receiving of the echoes can include receiving the echoes with a phased array configured to focus on at least one voxel within the medium being imaged.

In the method, the transmitting of the broadband ultrasound signal can include transmitting the broadband ultrasound signal with a first phased array that focuses the broadband ultrasound signal at a least one voxel within the medium being imaged and the receiving of the echoes can include receiving the echoes with a second phased array configured to focus on at least one voxel within the medium being imaged.

In the method, the first and second phased array can each include a plurality of array elements and the array elements of the first phased array can be interleaved with the array elements of the second phased array.

Another aspect of this disclosure is a method of ultrasound imaging with frequency compounding for speckle reduction. The method can include transmitting N ultrasound pulses each having a different center excitation frequency into a medium being imaged; receiving echoes of the N ultrasound pulses from the medium being imaged; generating a plurality of A-scan speckle images by frequency filtering the received echoes, where each of the A-scan speckle images can be formed by echoes associated with a different center excitation frequency; and frequency compounding the A-scan speckle images into an A-scan frequency-compounded ultrasound image.

The method can also include obtaining a plurality of A-scan frequency-compounded ultrasound images, where obtaining each of the A-scan frequency-compounded ultrasound images can include performing the transmitting, receiving, generating, and frequency compounding steps and generating a frequency-compounded B-mode ultrasound image by combining the plurality of A-scan frequency-compounded ultrasound images.

In the method, the transmitting of the N ultrasound pulses can include transmitting the N ultrasound pulses with a first transducer array and the receiving of the echoes can include receiving the echoes with a second transducer array.

In the method, the transmitting of the N ultrasound pulses can include chirping the N ultrasound pulses such that the pulses have center excitation frequencies that rise over time.

In the method, frequency filtering the received echoes can include compensating for time delays and for the chirping of the N ultrasound pulses.

The method can also include repeating the steps of obtaining the plurality of A-scan frequency compounded ultrasound images and generating the frequency-compounded B-mode ultrasound image in real-time at a framerate of at least 10 Hertz.

The method can also include visually displaying the frequency-compounded B-mode ultrasound image.

Another aspect of this disclosure is an ultrasound transducer probe. The ultrasound transducer probe can include a first phased transducer array configured to transmit ultrasound signals into a medium, where the first phased transducer array can include a plurality of transmitting elements and a second phased transducer array configured to receive ultrasound echoes from the medium, where the second phased transducer array can include a plurality of receiving elements. In the method, the transmitting elements of the first phased transducer array can be interleaved with the receiving elements of the second phased transducer array.

In the method, the transmitting elements of the first phased transducer array can be driven with signals have configurable phase delays so as to provide transmit focusing and echoes received by the receiving elements of the second phased transducer array can be processed with configurable phase delays to provide receive focusing.

For purposes of summarizing the disclosure, certain aspects, advantages and novel features of the innovations have been described herein. It is to be understood that not necessarily all such advantages may be achieved in accordance with any particular embodiment. Thus, the innovations may be embodied or carried out in a manner that achieves or optimizes one advantage or group of advantages as taught herein without necessarily achieving other advantages as may be taught or suggested herein.

BRIEF DESCRIPTION OF THE DRAWINGS

Embodiments of this disclosure will now be described, by way of non-limiting example, with reference to the accompanying drawings.

DETAILED DESCRIPTION

Figure 1A:
FIG. 1A illustrates an ultrasonic transducer probe that includes a transmitting array interwoven with a receiving array according to an embodiment of the disclosed technology.

The following detailed description of certain embodiments presents various descriptions of specific embodiments. However, the innovations described herein can be embodied in a multitude of different ways, for example, as defined and covered by the claims. In this description, reference is made to the drawings where like reference numerals can indicate identical or functionally similar elements. It will be understood that elements illustrated in the figures are not necessarily drawn to scale. Moreover, it will be understood that certain embodiments can include more elements than illustrated in a drawing and/or a subset of the elements illustrated in a drawing. Further, some embodiments can incorporate any suitable combination of features from two or more drawings. The headings provided herein are for convenience only and do not necessarily affect the scope or meaning of the claims.

I. Ultrasonic Imaging Systems and Methods

As discussed above, ultrasound imaging is becoming an increasingly important tool for diagnostic imaging. In ultrasound imaging, an A-scan image can be formed emitting an ultrasound pulse and recording echoes of the ultrasound pulse as it propagates within a medium. The time delay between transmitting of an ultrasound pulse from a transducer and the resulting echo returning to the transducer give an indication of the depth in the medium at which the ultrasound pulse reflected or echoed off the medium. Thus, the set of echoes resulting from a single ultrasound pulse can be used to form a one-dimensional ultrasound image. A two-dimensional B-scan image can be formed by collecting a sweeping series of A-scans, such that each of the one-dimensional A-scans forms a separate line in the two-dimensional B-scan image.

Ultrasound imaging has many desirable characteristics, such as relatively fast, real-time imaging, low cost, and no exposure to ionizing radiation such as would be the case with x-ray diagnostics. However, ultrasound imaging can suffer from the presence of significant speckle noise (e.g., significant and widespread background noise in ultrasound images due to back-scattering of sound by the tissue being imaged). In clinical and other settings, the useful resolution of such ultrasound images can be degraded by the speckle noise.

Speckle noise can be the result of coherent back-scattering of sound by the distribution of scatterers within each scattering voxel. A voxel is the individual unit of spatial volume being imaged. In each voxel, suppose we have scattering amplitudes $A_1(\vec{x}_1)$, $A_2(\vec{x}_2)$, $A_3(\vec{x}_3)$, . . . . If these amplitudes interfere constructively or destructively, the scattered signal $|A_1(\vec{x}_1)+A_2(\vec{x}_2)+A_3(\vec{x}_3)+ \ldots |^2$ can be either more or less than the sum of the scattering intensities of each of the scatterers, $|A_1(\vec{x}_1)|^2+|A_2(\vec{x}_2)|^2+|A_3(\vec{x}_3)|^2+ \ldots$, thus producing speckle.

There are several approaches for speckle reduction. One method is to average over N independent speckle images, which can reduce the speckle by $\sqrt{N}$. The multiple images can be obtained by using different portions of an ultrasound array. In a linear array of total aperture length L, the resolution at any given depth z is approximately proportional to L/z. If the aperture is broken up into N sub-segments for the purposes of speckle reduction, the spatial aperture of each view is decreased by N and the resolution becomes (L/N)/z. Thus, this method of speckle reduction sacrifices both image acquisition time and spatial resolution. There are also post data-collection image processing algorithms. However, due to the randomness and high density of the speckle pattern, post data-collection algorithms in general have not been able to recover all the lost information hidden in the speckle image.

II. Speckle Suppression by Frequency Compounding

Technology disclosed herein involves compounding of ultrasound images at different frequency bands to reduce or suppress speckle in ultrasound images. Frequency compounding can exploit a frequency (temporal) degree of freedom in suppressing speckle. The ultrasound images may be obtained separately using different excitation signals or may be obtained using a broadband excitation signal and spectral-filtering of an ultrasonic return signal, as examples.

In some embodiments, ultrasound images may be obtained using acoustic frequency mixing, where sound at two frequencies (e.g., two excitation pulses, which may propagate collinearly or non-collinearly) interacts in a nonlinear medium to generate a third frequency. In certain embodiments, difference-frequency generation is used. Sum-frequency and/or higher-order nonlinear mixing can alternatively or additionally be used. In other embodiments, A-scans in ultrasound images may be obtained using a single ultrasonic pulse (e.g., without using acoustic frequency mixing).

A. Frequency Compounding Via Time-Bandwidth Optimization

One trade-off in frequency compounding is between the axial resolution and speckle reduction. A narrower bandwidth generally gives rise to longer pulse duration and coarser longitudinal resolution. Additionally, the correlation between speckle images increases as the separation of their central frequencies decreases. In other words, the speckle of images obtained using similar central frequencies is more closely correlated than speckle images obtain using relatively distant central frequencies. Hence, averaging images having relatively close central frequencies together is less effective for speckle reduction (as compared to images obtained with greater separation between their respective central frequencies). For at least these reasons and within the fixed total bandwidth of a transducer, more independent speckle images can be acquired when the bandwidths of the excitation frequencies are reduced. Accordingly, the speckle reduction can be improved. While relatively narrow bandwidth pulses are useful for maximizing the number of independent speckle images that can be acquired, narrow bandwidth pulses also generally give rise to longer pulse duration and coarser longitudinal resolution.

The technology disclosed herein provides frequency compounding, in some embodiments, using optimized (or semi-optimized) time-bandwidth product ultrasound pulses. With such ultrasound pulses, the pulse duration is shortened as compared to non-optimized pulses for the same bandwidth. With proper choice of pulse duration, the axial resolution can be adjusted to remain comparable or less than the transverse resolution defined by the numerical aperture of the ultrasound source. A compounded image can then be obtained by obtaining multiple images (referred to herein as speckle images) at different respective center frequencies and then averaging the speckle images together. In at least some embodiments, the center frequencies of the speckle images may collectively span over substantially all of the bandwidth of the transducer.

A Gaussian pulse of duration $\Delta t$ has a temporal envelope profile of $$g(t) = \frac{1}{(2\pi\sigma^2)^{\frac{1}{2}}} \exp\left[-\frac{t^2}{2\sigma^2}\right], \quad \text{(Equation 1)}$$

$$\Delta t \Delta \omega = 0.5,$$

where $\Delta\omega = 2\pi\Delta f$ and $\Delta t$ are the 1 σ widths of the intensities of the Gaussian Fourier transform pair. The full-width at half maximum of the pulse $\Delta t_{FWHM} = 2.35 \Delta t$. Gaussian pulses can optimize the time-bandwidth product (Equation 1) and may further improve or optimize the trade-off between speckle reduction and axial resolution. The time-bandwidth relation shows that the axial resolution, which is proportional to $\Delta t$, is coarser for narrower bands. The values of $\Delta\omega$ and $\Delta t$ in Equation 1 can be chosen such that the axial and transverse resolutions are similar (e.g., are within 50% of each other, within 10% of each other, or within 5% of each other). In particular, $\Delta t$ can be chosen such that the axial resolution (which is proportional to $\Delta t$) is similar to the transverse resolution (which is defined at least partially by the numerical aperture of the ultrasound source).

B. Frequency Compounding Embodiments

In some embodiments, imaging is performed in a pulse-echo configuration and the pulses at different frequencies are transmitted sequentially. Two interwoven linear arrays of an ultrasound probe, sometimes referred to as an ultrasound transducer head, may be used for the transmitter and receiver, respectively. FIG. 1A illustrates an interwoven linear array 100 that includes transmitter array elements 110 and receiver array elements 120, which are interwoven together. The transmitter array elements 110 may form a phased array such that the propagation direction of the emitted sound is determined by selecting appropriate phase delays for each of the transmitter array element 110. This may be referred to herein as transmit focusing. In addition to the propagation direction of the sound, imaging voxels (e.g., regions of material being imaged by the system) may be further located by the delay time of the echo. This can give depth information (e.g., the round-trip time between transmission of a pulse and the reception of an echo from a given distance away from the transducer probe gives depth information). Similar phase delays may be applied to the receiver array elements 120, in at least some embodiments, such that the receiver array elements 120 track the propagation of the pulses (e.g., such that the receiver is focused on the current imaging voxel, which may move around as an ultrasound image is captured).

Figure 1B:
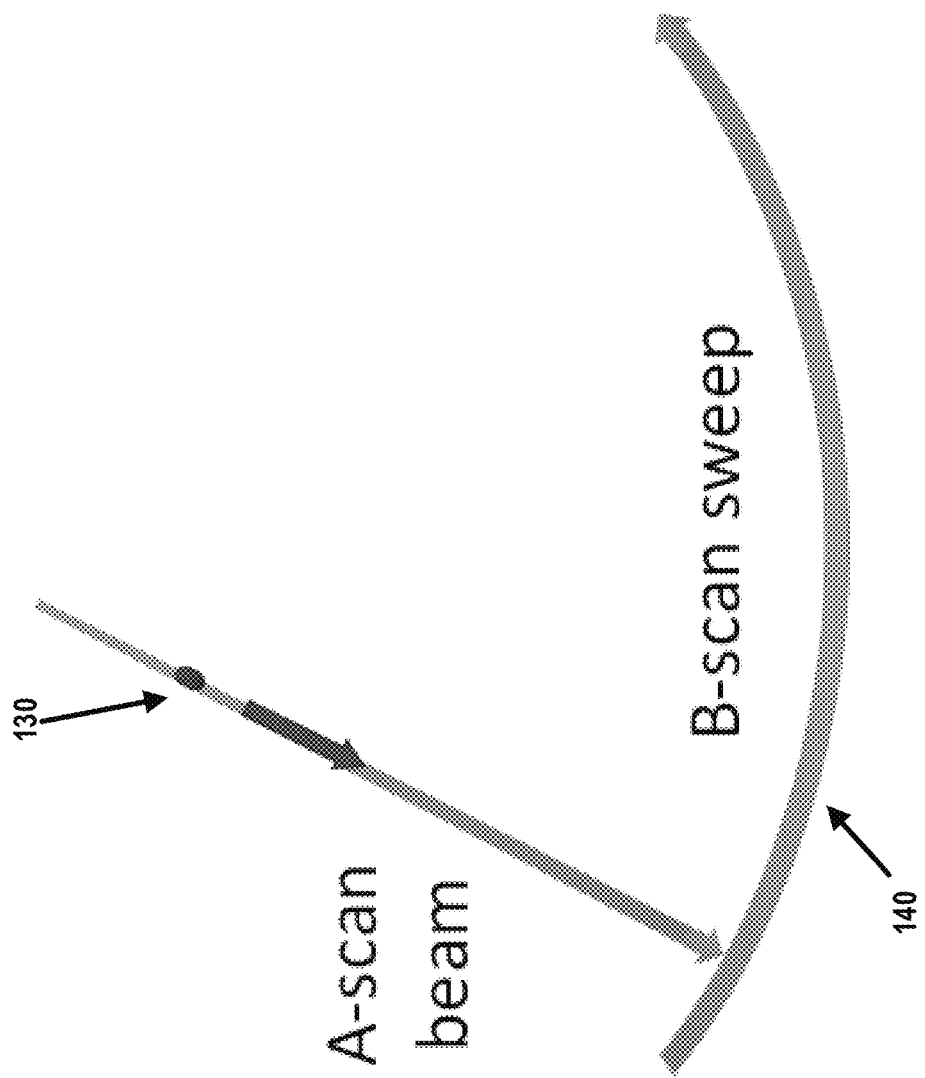
FIG. 1B illustrates ultrasonic pulses for an A-scan and also illustrates how a B-scan image can be formed with a sweep of A-scan according to an embodiment of the disclosed technology.

FIG. 1B illustrates an A-scan beam formed from one or more ultrasonic pulses such as pulse 130 that travel along a line through a medium being imaged and echo or reflect off of various structures the medium along the line. Detection of an echo at the frequency of the pulse (or at a difference or sum frequency when utilizing nonlinear embodiments as described herein) at different time delays corresponds to different z-positions along the scan line of the A-scan.

A B-mode image can be formed by the coordinated sweep of the A-scan beams. A processing circuit of the ultrasound imaging system can image the response from the voxels associated with each A-scan. After the pulses associated with a single A-scan have been emitted, the A-scan beam can be stepped to another direction (e.g., along the B-scan sweep 140) such that additional voxels can be imaged. In some embodiments, the A-scan beam can be stepped to another direction before an entire round-trip time has elapsed, particularly when utilizing a transducer probe with separate transmit and receive elements or arrays. In this manner, the system can obtain a B-scan or B-mode image of the object being imaged.

Figure 2:
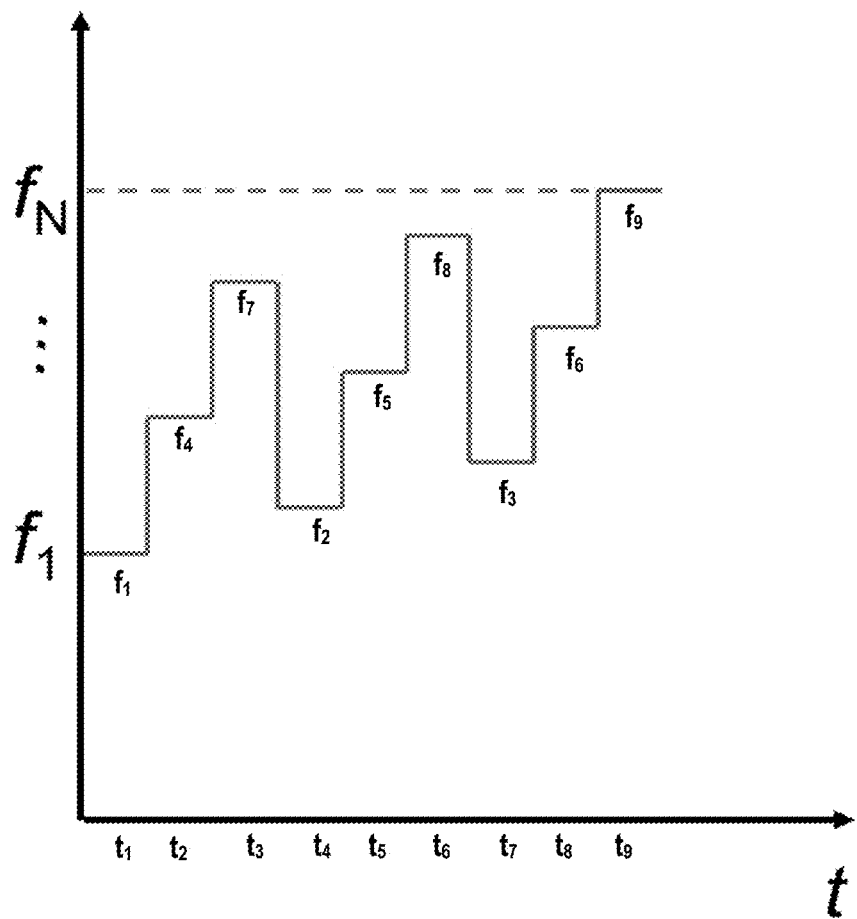
FIG. 2 illustrates a graph of ultrasonic pulses that can be transmitted by the transducer probe of FIG. 1A according to an embodiment of the disclosed technology.

In the time of one A-scan, N Gaussian pulses centered at a corresponding number of frequencies $f_1, f_2, f_3, \ldots, f_N$ can be transmitted. The pulses may be Fourier-transform limited pulses centered at frequencies $f_1, f_2, f_3, \ldots, f_N$ and may be generated digitally from a look-up table and amplified by a pulsed amplifier. As shown in FIG. 2, adjacent ultrasound pulses are separated in frequency to facilitate spectral separation and to facilitate forming N independent speckle images. By separating the transmitting and receiving functions (e.g., by utilizing a transducer with the capability to simultaneously receive and transmit ultrasound signals such as transducer array 100 of FIG. 1A), multiple pulses can be sent during the round-trip transit time of a single ultrasound pulse, while detection is performed simultaneously or approximately simultaneously. In this way, the time to image a frequency compounded A-scan is not increased relative to a single frequency A-scan. As examples, the number of pulses sent during an A-scan and/or the round-trip transit time may be 3 pulses, 5 pulses, 10 pulses, 15 pulses, or more than 15 pulses. In general, the number of pulses sent during an A-scan and/or the round-trip transit time may be any desired number of pulses.

In at least some embodiments, the time to image a frequency compounded A-scan is sufficiently low that frequency-compounded B-mode ultrasound images can be obtained in real-time at a framerate of at least 10 Hertz. In other words, the system disclosed herein may capture frequency-compounded ultrasound images of at least 100 by 100 pixels, at least 200 by 200 pixels, or at least 400 by 400 pixels and may capture such images at a real-time frame rates such as at least 1 Hz, at least 5 Hz, at least 10 Hz, at least 20 Hz, or at least 30 Hz.

As shown in FIG. 2, nine Gaussian pulses centered at nine difference frequencies can be transmitted in the time of one A-scan (e.g., N equals nine), in at least some embodiments. Additionally, Gaussian pulses may be transmitted in a stair-step order such that pulses of relatively similar frequencies are separated by pulses of relatively dissimilar frequencies. The temporal separation of the pulses with similar frequencies may reduce the interference of their echoes when forming images at these frequencies with receive focusing. As an example and as shown in FIG. 2, an initial pulse at $f_1$ may be transmitted at $t_1$, while the pulse at $f_2$ may be transmitted at $t_4$ after pulses at $f_4$ and $f_7$ are transmitted at $t_2$ and $t_3$, respectively. In other words, FIG. 2 illustrates how pulses may be transmitted in steps that increase, then decrease (e.g., a pattern of two increasing steps and a decreasing step, with each pulse being at a unique frequency). In this manner, pulses covering most or all of the bandwidth of an ultrasound probe may be transmitted while avoiding transmitting pulses of relatively similar frequencies in close succession. This may help facilitate the imaging process.

The pulses may be separated in time (e.g. 3Δt, where Δt is the pulse duration) to allow for the separation of the pulses through receive focusing. In some embodiments, the receive numerical aperture may be significantly higher than the transmit numerical aperture. In such embodiments, the system may have tighter receive focusing capabilities, which may facilitate distinguishing between echoes associated with different excitation frequencies (e.g., different excitation pulses at different frequencies). The signal can be further separated by frequency domain filtering using digital Fourier transforms. The driving voltages of the pulses can compensate for the natural response of the transducers such that the pulse energies at frequencies $f_1, f_2, f_3, \ldots, f_N$ are approximately the same (e.g., in a manner similar to that described in connection with FIGS. 4A and 4B below).

Compounding of the speckle images can be performed by averaging the amplitudes or the intensities. Envelope detection for the A-scan signal can be performed either digitally (e.g., using a Hilbert transform) or in the analog domain (e.g., using a low-pass filter, a band-pass filter, a high-pass filter, or a combination thereof). A B-scan image is formed by scanning the direction of the A-scan signal. Compounding of the images is performed by averaging the values of the corresponding pixels in the images.

Figure 3:
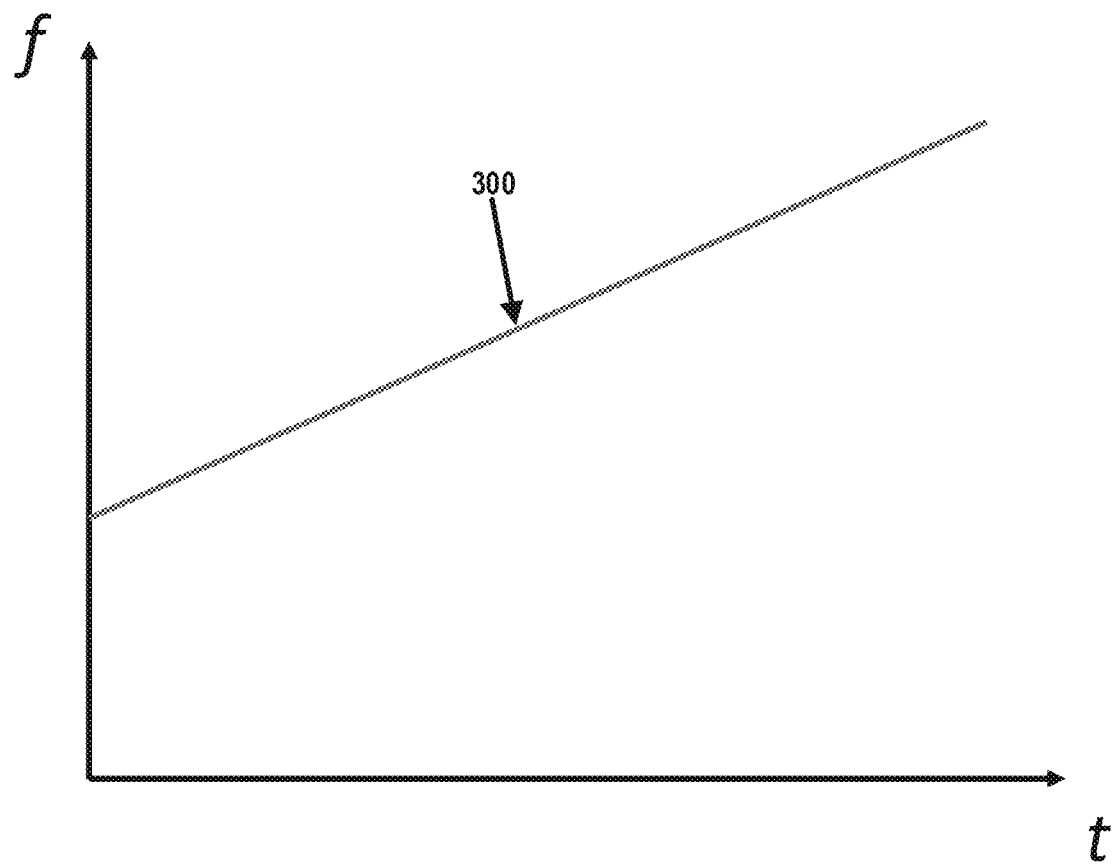
FIG. 3 illustrates a graph of central frequencies of the ultrasonic pulses of FIG. 2 according to an embodiment of the disclosed technology.

In some embodiments, a frequency chirp is applied to the transmission signal 300, as shown in FIG. 3. A frequency chirp may help spread out the acoustic power over time and thereby reduce the peak acoustic power. In some situations, the peak acoustic power can be limited by safety considerations. A frequency chirp allows for more acoustic power to be transmitted as compared to the non-chirped pulse, without exceeding limitations on peak acoustic power, and also improves the signal to noise in the acquired image. The central frequencies of individual pulses (which may be optimized time-bandwidth product ultrasound pulses) may rise over time (e.g., monotonically rise over time) such that the pulses span some or all of the bandwidth of the transducer probe such as transducer probe that includes the transducer array 100. The spectrum of the frequency chirped signal(s) may also be normalized by driving the transducer with a signal that compensates for the natural response of the transducer, for example, as described in connection in FIGS. 4A and 4B.

An interwoven linear array such as transducer array 100 of FIG. 1A may be used to allow for simultaneous transmission and detection. Alternatively, the same transducer elements may be used for transmission and detection. In this case, a dead period in receive is applied until the transmission is finished.

The different frequency bands may be obtained by frequency filtering of the receive signal. This can be accomplished, for example, by the following procedure. For a single A-scan, the amplitude of the back-scattered sound wave A(t) is recorded. The time t covers the entire time record of the detected ultrasound signal as the pulse propagates into the tissue being imaged. Digital Gaussian filters can be applied in the Fourier space of the detected signal to generate $F_{f(i)}(v)$, where f (i) are the center frequencies of the spectrally filtered Fourier-transformed data. The set of functions $F_{f(i)}(v)$ can then transformed back into the time domain $A_{f(i)}(t)$. Each $A_{f(i)}(t)$ is delayed to compensate for the time delay of the different frequency bands caused by the frequency chirp (thus the frequency chirp of FIG. 3 may facilitate frequency compounding by facilitating the digital filtering of different excitation pulses). The signal envelope of these signals can then be obtained digitally using Hilbert transform, low-pass filtering, or other suitable filtering. The axial resolution may be determined by the spectral width Δf(i) for the spectral filtering and the chirp in frequency.

C. Broadband Transmission Signals with Spectral Filtering

Figure 4A:
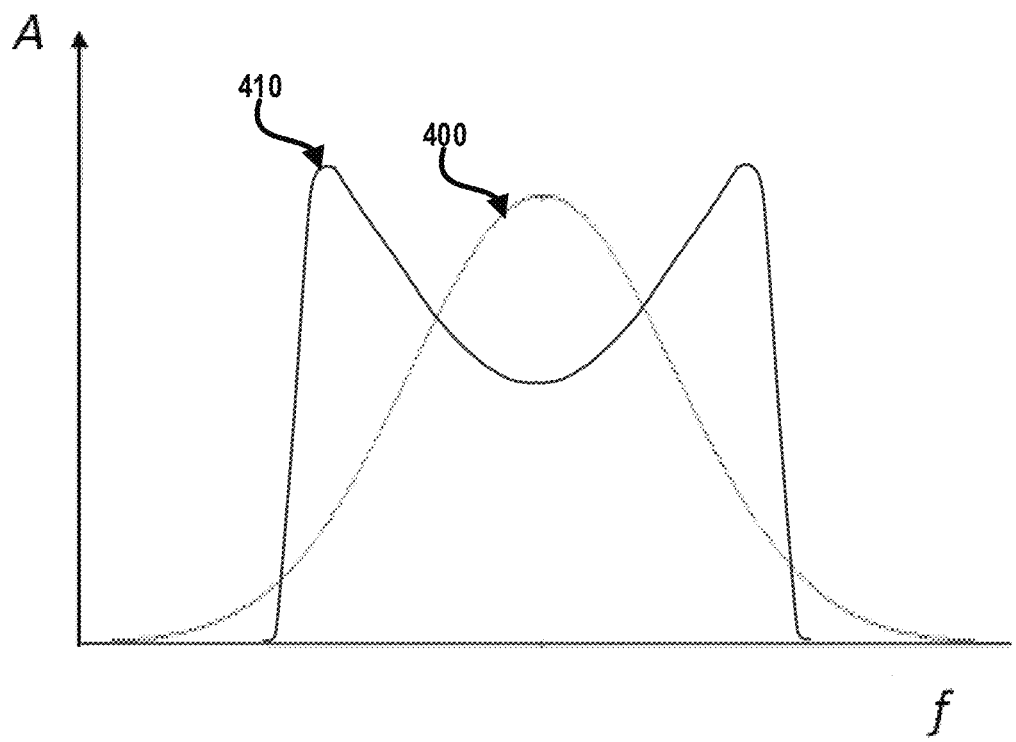
FIG. 4A illustrates a graph of the response of the transducer probe of FIG. 1A and of a transmission signal that may drive the transducer probe according to an embodiment of the disclosed technology
Figure 4B:
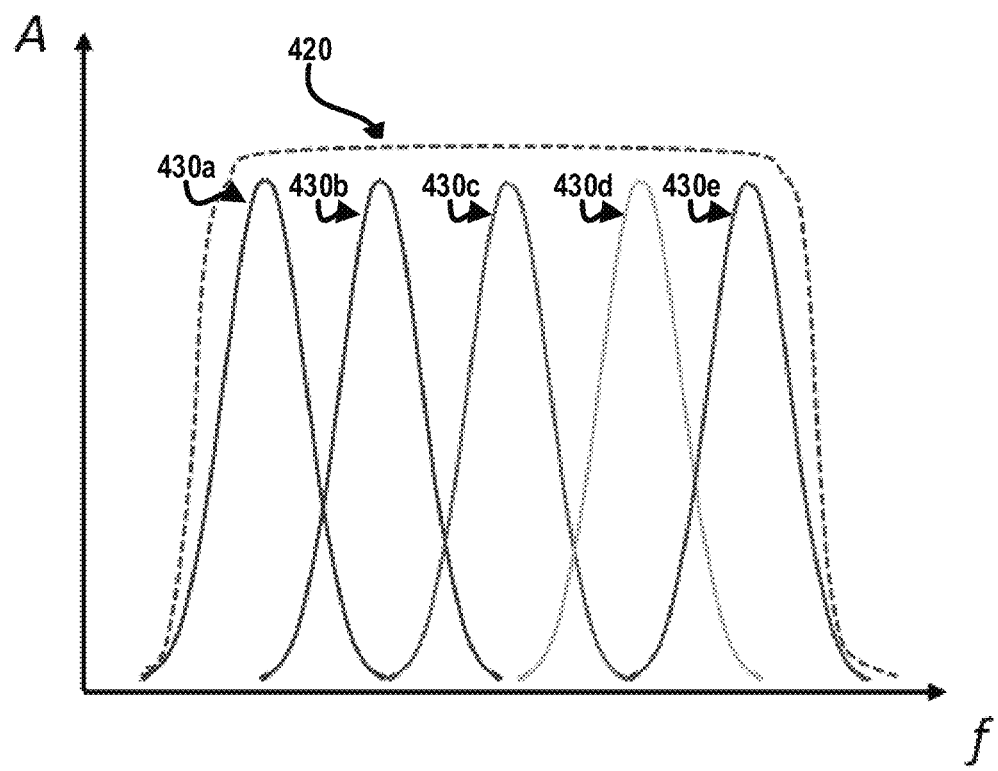
FIG. 4B illustrates a graph of the output of the transducer probe of FIG. 1A when driven with the transmission signal of FIG. 4A and also illustrates Gaussian filters that may be used as part of a frequency-compounding technique according to an embodiment of the disclosed technology.

In various embodiments, a single pulse with a broadband spectrum is used to excite a medium in a pulse-echo configuration. As shown in FIG. 4A, transducers such as transducer array 100 of FIG. 1A may have a natural response 400, which may be indicative of the amplitude of ultrasound signals as a function of frequency produced by the transducer. This can correspond to when the transducer is driven by substantially constant-power and variable-frequency excitation signal. To compensate for the natural response 400 and produce a more constant spectral response over a relatively wide bandwidth such as response 420 of FIG. 4B, transducers such as transducer array 100 can be driven with signals that follow transmission input spectrum 410 of FIG. 4A. Accordingly, an input signal driving transducers of an ultrasound transducer array can compensate for a frequency response of the transducer array to generate more constant frequency response for the ultrasound transducer array. As a result, various embodiments may excite a medium in a pulse-echo configuration using an ultrasound pulse (or multiple pulses) with a broadband spectrum having the shape of the response 420 of FIG. 4B. Using arrangements of this type, non-linearity in a transducer's response can be compensated for and removed. Arrangements of this type may be used for any desired type of transducer. In general, different types of transducers, different transducer models, and transducers from different manufacturers may have different properties such as different natural responses. To compensate for these differences, the transmission input spectrum may be varied, based on the particular transducer in use, to produce desired spectral responses. Different types of transducers that may be used in the embodiments disclosed here including, but are not limited to, linear transducers, convex (or other shaped) transducers, phased array transducers, pencil transducers, and transducers designed to fit within and/or image specific body parts. These are merely illustrative examples.

In at least some embodiments, one or more pulses with a broadband spectrum is used to excite a medium and the resulting ultrasound echo signal A(t) are received. Then, a Fourier transform of the ultrasound echo signal A(t) is taken to obtain $\tilde{A}(\omega) = \int_0^{t_{final}} A(t) \exp(-i\omega t)\, dt$. If desired, normalization constants may be ignored. The resulting data (e.g., $\tilde{A}(\omega)$) can then be digitally filtered, by frequency, to form $\tilde{A}_{f1}(\omega), \tilde{A}_{f2}(\omega), \tilde{A}_{f3}(\omega), \ldots$. The digitally-filtered signals can then be Fourier transformed back to the time domain to create $A_{f1}(t), A_{f2}(t), A_{f3}(t), \ldots$. Each of these time-domain signals can then be used to create ultrasound images at difference frequencies (e.g., images having independent speckle that can be averaged together to reduce speckle). Thus, with a single pulse, a plurality of images that are effectively associated with difference frequencies can be obtained. If desired, the ultrasound images may be normalized relative to each other.

In at least some embodiments, the broadband spectrum may have a bandwidth that covers substantially all of the bandwidth of a transducer array (e.g., the transducer array 100 of FIG. 1A). Spectral filtering is then performed (e.g., digitally), for example, as described above. As an example, digital filters such as Gaussian filters 430a, 430b, 430c, 430d, and 430e may be applied to the echoes resulting from a broadband pulse to form a plurality of independent speckle images (e.g., to form a separate speckle images associated with each of the filters). In some embodiments, the filters may be non-Gaussian. With arrangements of this type, a plurality of independent speckle images can be obtained using a single pulse. If desired, however, multiple pulses, which may each be broadband pulses, may be used to achieve further speckle reduction. A B-mode image can be acquired by scanning the A-scan lines using a phased array. A compound image is obtained by averaging the ultrasound images of the frequency-filtered images.

III. Example Results for Speckle Suppression by Frequency Compounding

Figure 5:
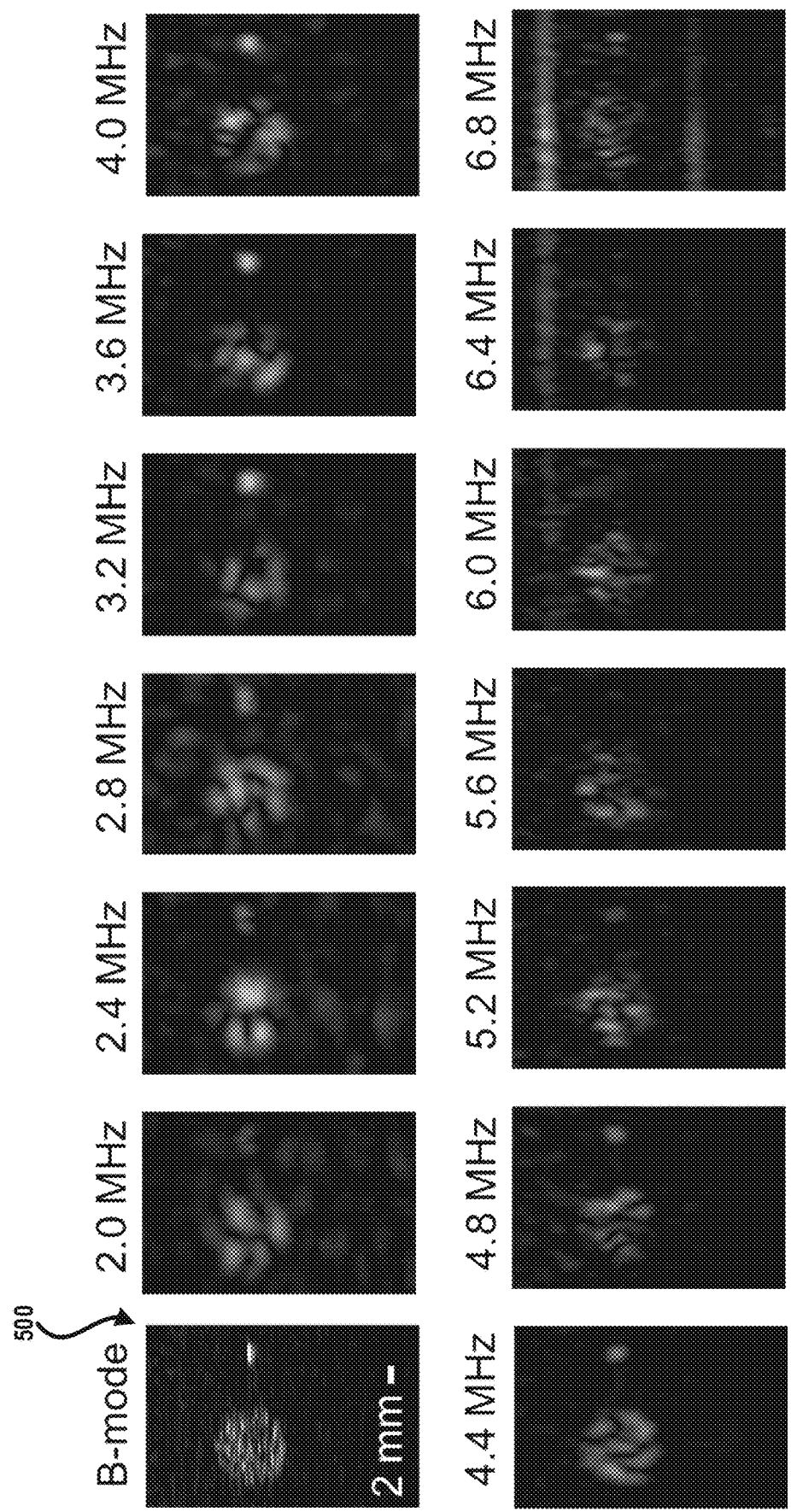
FIG. 5 illustrates an unfiltered ultrasonic image of an ultrasound phantom and illustrates ultrasonic images that have been filtered using Gaussian filters at various frequencies according to an embodiment of the disclosed technology.

The top-left panel of FIG. 5 shows the B-mode image 500 of an ultrasound phantom, obtained without frequency compounding. The circular region on the left of the B-mode 500 image corresponds to a hyperechoic region, namely, a region that generates stronger echo compared to the background. The hyperechoic region contains a higher concentration of scatterers as compared to the background region. The bright spot on the right is the echo from a 100 μm diameter nylon wire running perpendicular to the image. Since the diameter of the nylon wire is much smaller than the sound wavelength in the frequency range tested, the shape of the bright spot corresponds to the point-spread function of the system. The width of the spot gives the transverse resolution and the height of the spot gives the axial resolution. As shown in the image, the axial resolution is approximately 5× finer than the transverse resolution, which is defined by the Abbe criterion $\delta x = \lambda/2NA$, where $\lambda$ is wavelength of the sound wave and NA is the numerical aperture of the ultrasound imaging "optics." The much finer axial resolution is a result of the use of a broadband transducer.

FIG. 5 shows the ultrasound images filtered with relatively narrow Gaussian bands. The speckle in the Fourier-filtered images (FFIs) has a lower spatial frequency in the axial direction compared to the B-mode image 500, which is a direct consequence of the narrower spectral bandwidth of the FFIs. Additionally, the speckle noise is significantly different for each center frequency. Consequently, the frequency compounding of several images is effective at reducing and/or eliminating speckle noise.

Figure 6A:
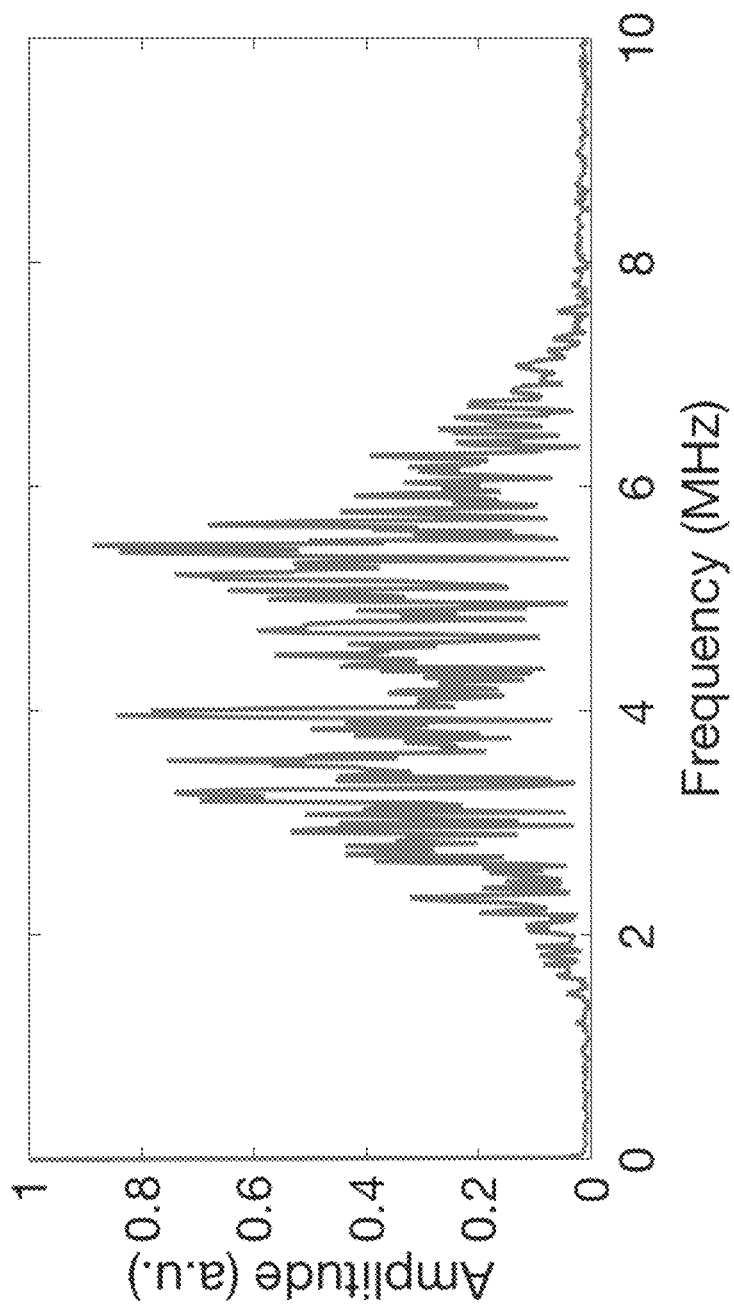
FIG. 6A shows the spectra of an ultrasound return signal that may be filtered as part of a frequency-compounding technique according to an embodiment of the disclosed technology.
Figure 6B:
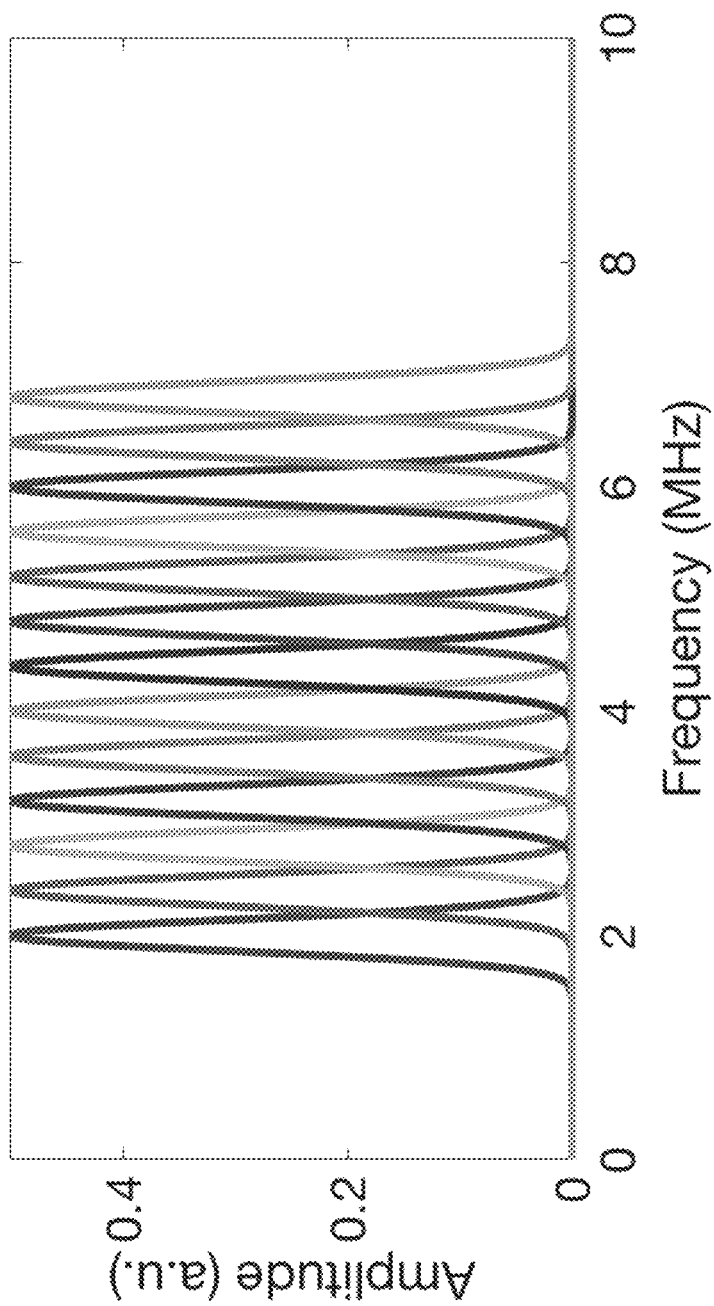
FIG. 6B shows the spectra of Gaussian filters that may be used in filtering an ultrasound return signal according to an embodiment of the disclosed technology.

FIG. 6A shows the amplitude spectrum (phase not shown) of a representative line scan (e.g., a single A-scan, which may be part of a B-mode image). The complex spectrum with both the amplitude and phase information may be multiplied with 13 Gaussian bands, shown in FIG. 6B, to yield 13 filtered spectra. The Gaussian bands can be chosen to have the same width of σ=0.14 MHz. If desired, the Gaussian bands may have different widths. The central frequencies of the Gaussian bands span from 2.0 MHz to 6.8 MHz with a separation of 0.4 MHz between the adjacent bands. In general, it may be desirable for the Gaussian bands to span more or substantially all of entire bandwidth of the transducer, to maximize speckle reduction. The filtered waveforms may be obtained by an inverse Fourier transform of the filtered spectra as described above. The Fourier filtered images at center frequencies f(i) are obtained by detecting the amplitude of the envelope of the filtered waveforms.

Figure 7:
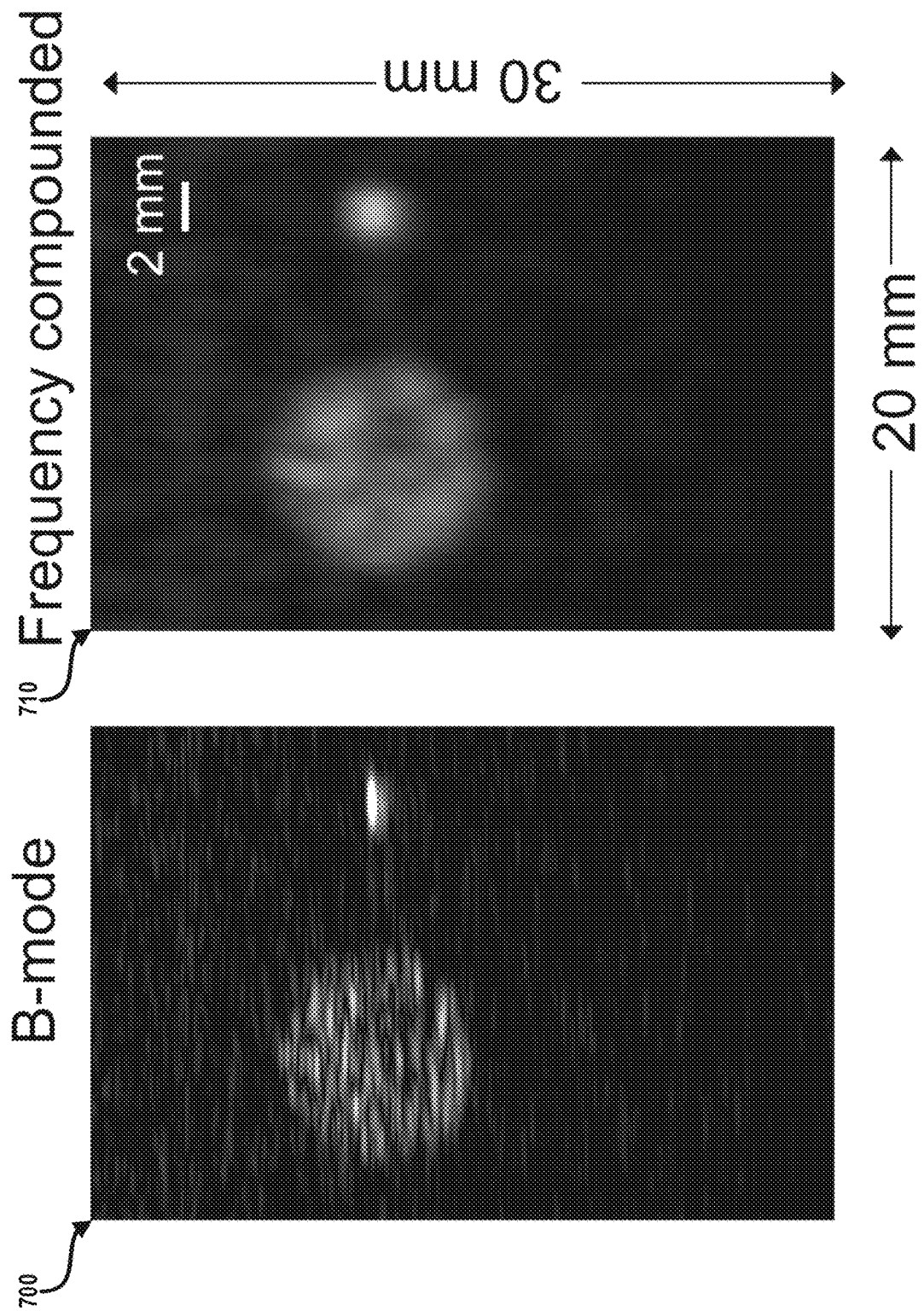
FIG. 7 illustrates the unfiltered ultrasonic image of FIG. 5 and a frequency-compounded ultrasonic image according to an embodiment of the disclosed technology

FIG. 7 compares the frequency compounded image 710 (e.g., using a broadband pulse and digital filtering of the received echoes to generate a plurality of speckle images that are then averaged together) with the original B-mode image 700 (e.g., a B-mode image captured without frequency compounding). The frequency width of each Fourier-filtered signal can be chosen such that the axial resolution is substantially the same as the transverse resolution, as demonstrated by the round point spread function of the 100 μm diameter nylon wire in the example with Gaussian bandwidths of σ=0.14 MHz.

Figure 8:
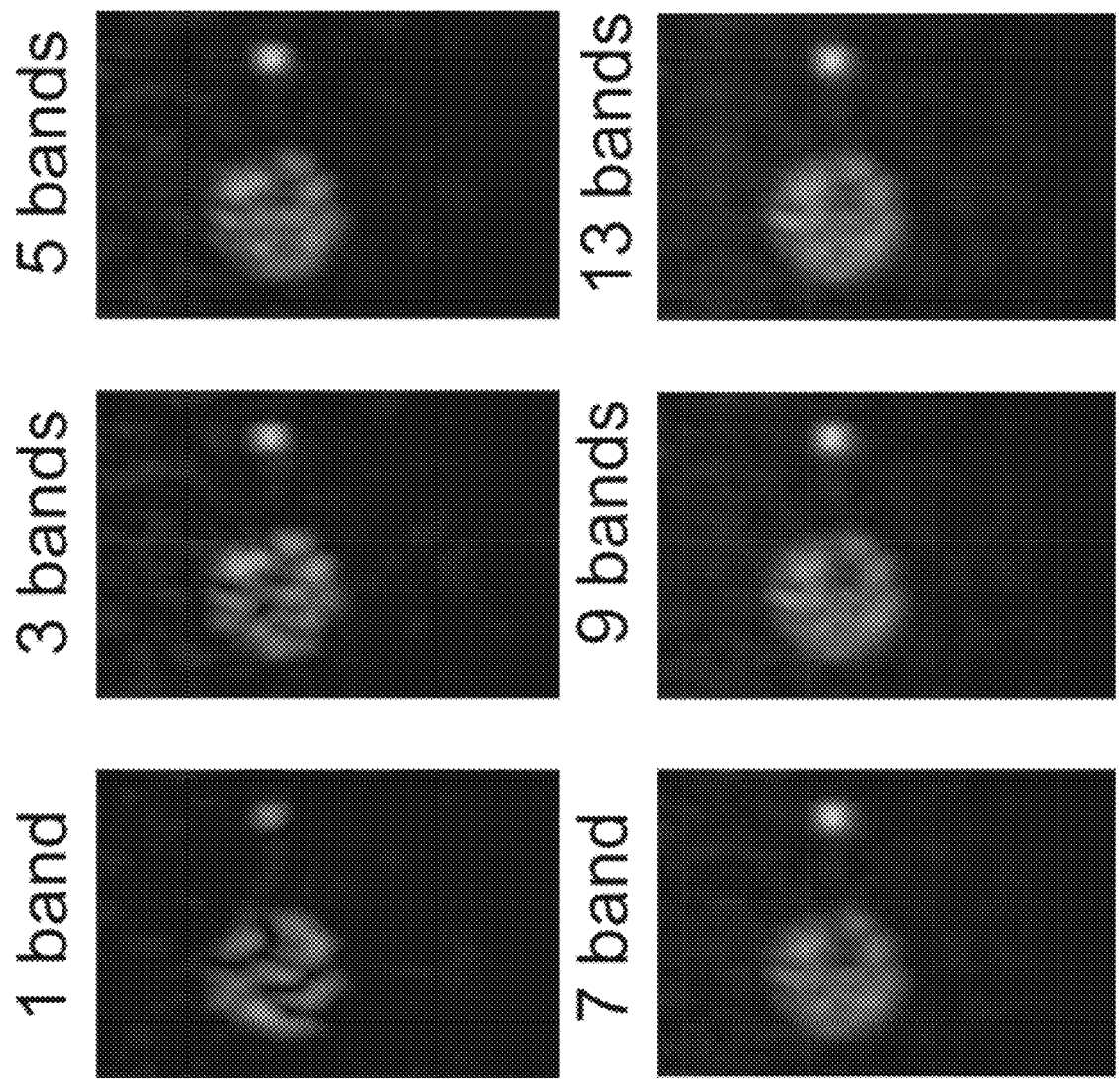
FIG. 8 shows a progression of frequency-compounded ultrasonic images having various levels of frequency-compounding according to an embodiment of the disclosed technology.

Evolution of the compounded speckle image as a function of the number of frequency bands is shown in FIG. 8. The compounded image 710 of FIG. 7 and the fully and partially compounded images of FIG. 8 illustrate the effectiveness of the technology disclosed herein in reducing speckle, as significant reduction of speckle in the compounded images is evident.

Figure 9:
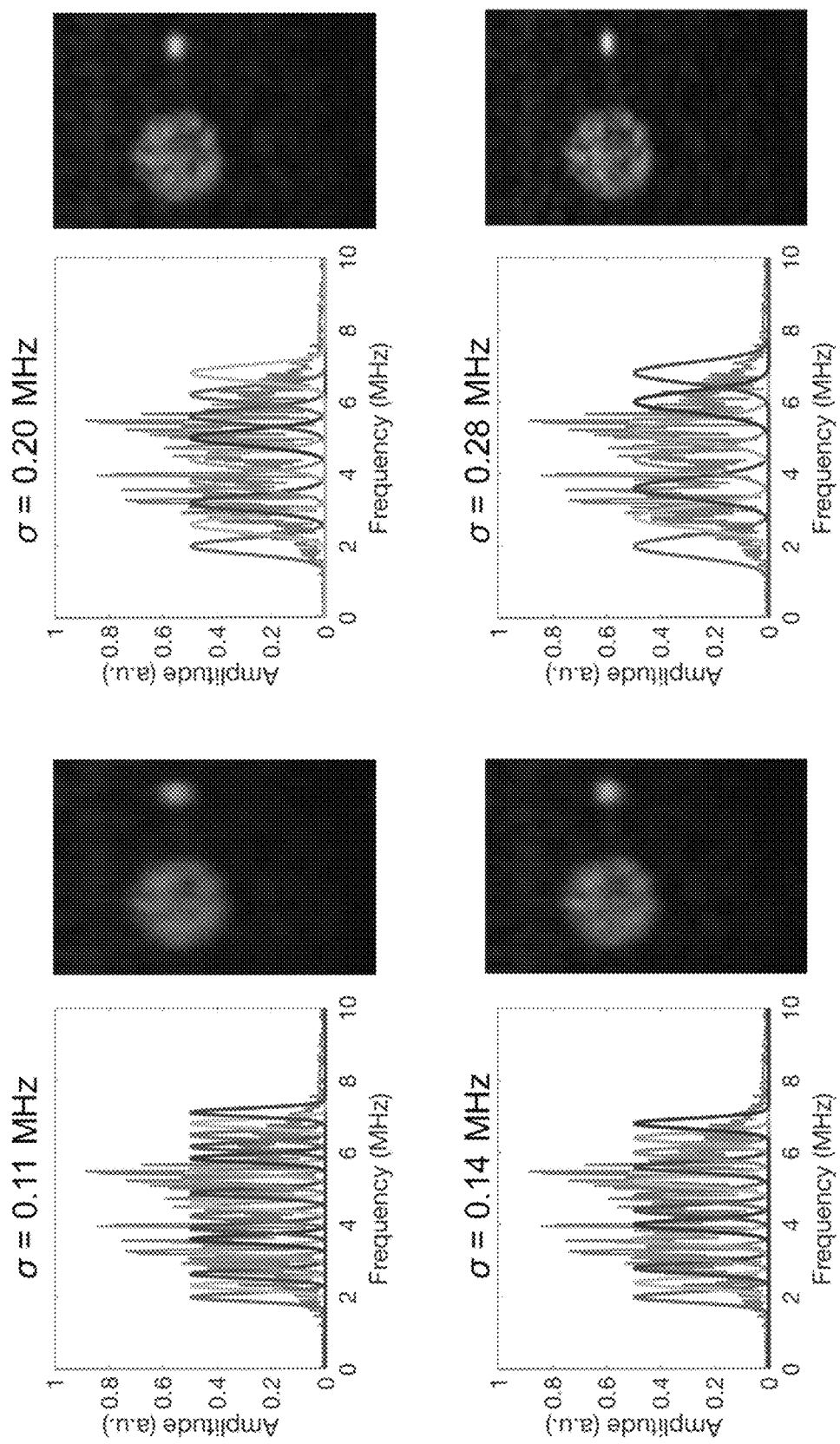
FIG. 9 illustrates frequency-compounded ultrasonic images obtained using varying numbers of Gaussian filters having various bandwidths and also illustrates the associated spectra of the ultrasound return signals overlaid with the associated Gaussian filters according to an embodiment of the disclosed technology.

In addition to the total bandwidth, the bandwidth of individual Gaussian filters can be significant (even while keeping the total bandwidth constant). As shown in FIG. 9, with increasing filter width, the axial resolution is improved. Consistent structures in the hyperechoic region for the different compound images shows that the structures correspond to actual inhomogeneity. Speckle would eventually appear when the bandwidth of individual Gaussian filter is increased to be comparable to the full bandwidth of the transducer as the number of independent speckle images would reduce to 1.

In at least some embodiments, the Gaussian bands may have different bandwidths, such that each Fourier-filter signal has an axial resolution that substantially matches the transverse resolution at its associated frequency. As previously noted, the transverse resolution is proportional to the wavelength of the sound wave and thus inversely proportional to the frequency (e.g., the transverse resolution decreases with increasing frequency). Thus, the transverse resolution may be finer at the higher frequencies. In embodiments in which the Gaussian bands have different bandwidths, the bandwidths of the Gaussian bands may increase with increasing frequency such that the axial resolution also improves (e.g., becomes finer) at the higher frequencies (and thus keeps pace with the improving transverse resolution at the higher frequencies). In some embodiments, the bandwidth of each Gaussian band may be selected such that the axial resolution for that particular frequency band matches the transverse resolution at that particular frequency band. In other words, the bandwidths may also be selected such that the common axial resolution is substantially the same as the transverse resolution of the imaging system.

We can quantify speckle using $\mu/\sigma$, where $\mu$ and $\sigma$ are the mean and standard deviation of the speckle amplitude. We denote $\mu/\sigma$ as the signal to noise ratio (SNR). Speckle reduction is then represented by an increase in $\mu/\sigma$. The SNR can be measured from the speckle image of the hyperechoic region of the phantom, as one example. Using a Gaussian bandwidth of $\sigma=0.14$ MHz, a reduction of speckle of approximately 3.8× is obtained. A typical range of speckle reduction is from 2× to 4×.

Figure 10:
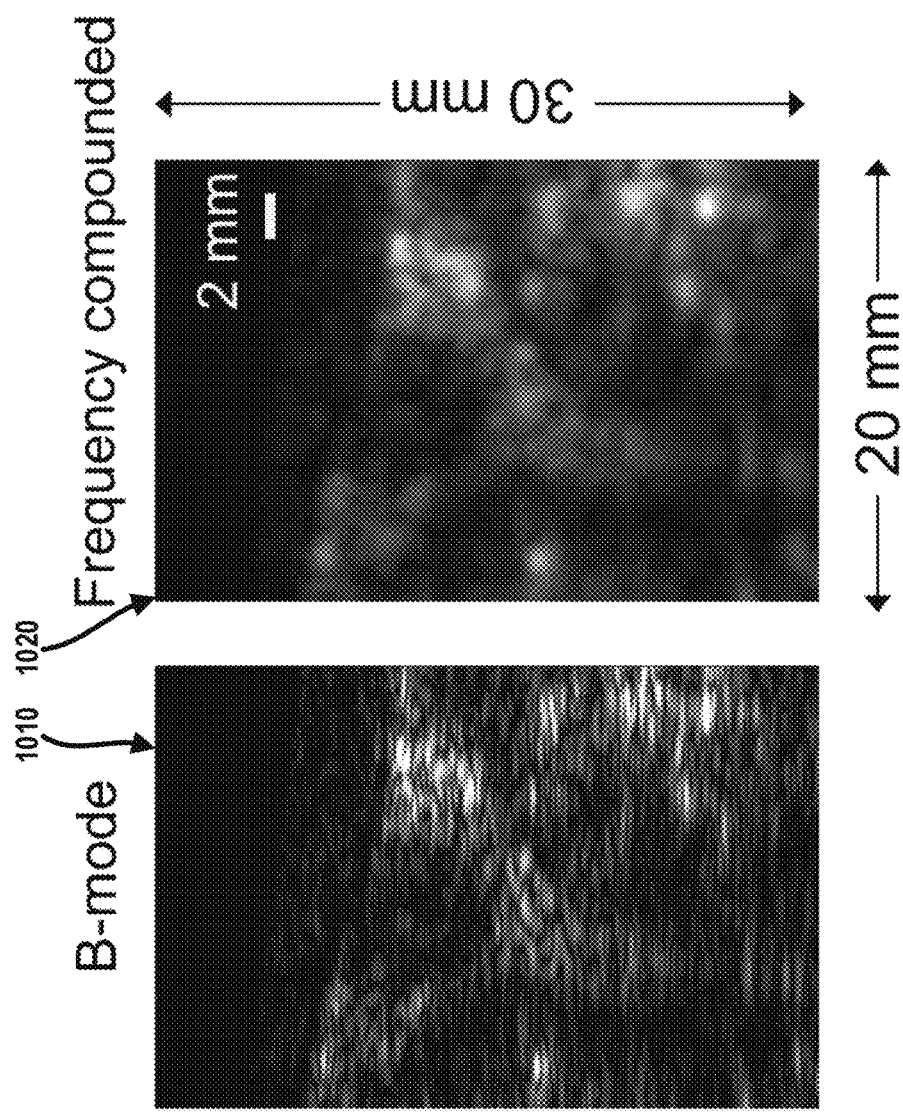
FIG. 10 illustrates an optical image of a pig kidney, an ultrasonic image of the same, and a frequency-compounded ultrasonic image of the same according to an embodiment of the disclosed technology.
Figure 10:
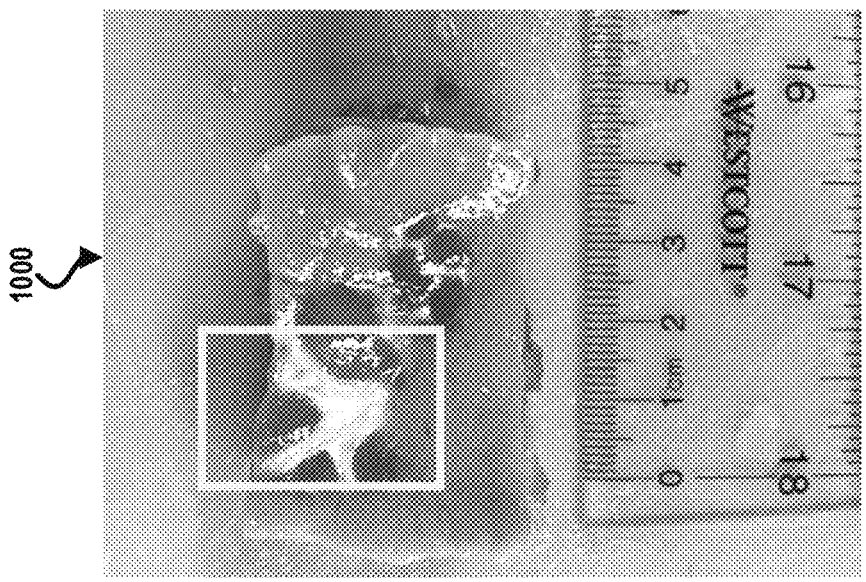

FIG. 10 illustrates example results of the Fourier-filter speckle reduction method and system disclosed herein, when used to image a piece of pig kidney. FIG. 10 illustrates an optical image 1000 of a portion of kidney tissue that was imaged by ultrasound. The minor and major calyces appear white in the optical image. The same features can be identified in a B-mode image 1010 captured without frequency compounding. The frequency compounded image 1020 shows reduced speckle compared to the B-mode image 1010 while maintaining good resolution.

Figure 11:
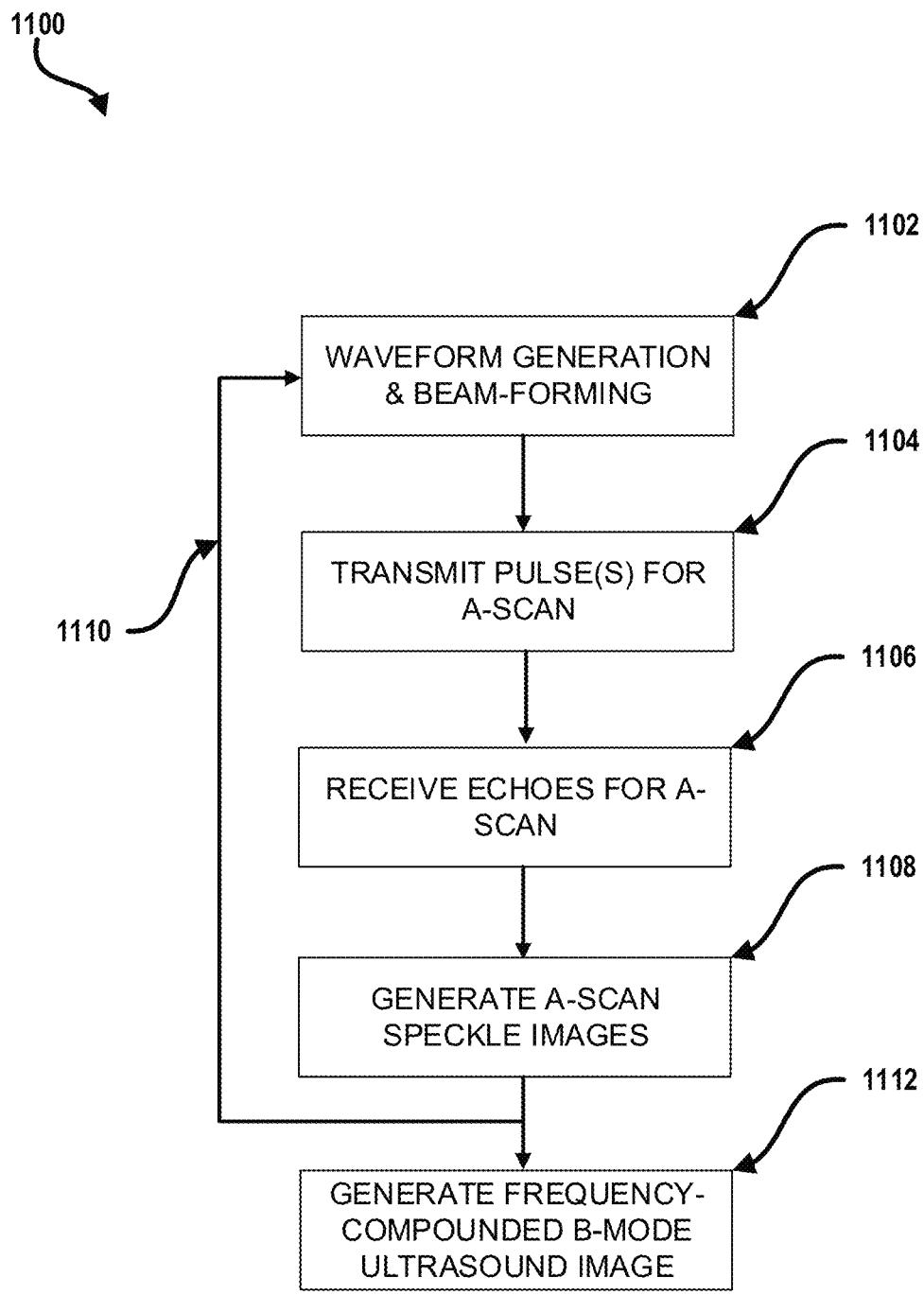
FIG. 11 is a flowchart of a method of ultrasound imaging with speckle suppression by frequency compounding according to an embodiment of the disclosed technology.

IV. A Method of Ultrasound Imaging with Speckle Suppression by Frequency Compounding FIG. 11 is a flowchart of a method 1100 of ultrasound imaging with speckle suppression by frequency compounding according to an embodiment of the disclosed technology.

In block 1102, ultrasound pulses are generated for transmission by an ultrasonic transducer array, such as transducer array 100 of FIG. 1A. Block 1102 may include applying phase delays to the ultrasound pulses such that different elements in a phased transducer array focus the ultrasound pulses in a desired direction. Block 1102 may involve generating broadband ultrasound pulses or generating optimized (or semi-optimized) time-bandwidth produce ultrasound pulses at one or more frequencies, as examples.

In block 1104, ultrasound pulse(s) are transmitted for an A-scan along a scan line. In certain embodiments, block 1104 may involve sending multiple ultrasound pulses at different frequencies during the time of a single A-scan (e.g., during the round-trip time of a single pulse). In some other embodiments, block 1104 may involve sending a single broadband pulse per A-scan. If desired, multiple broadband pulses may be transmitted for a single A-scan, and such pulses may be transmitted during the time of a single A-scan. Block 1104 may involve transmitting ultrasound pulse(s) with a phased array in a focused manner (e.g., a transmitting phased array may focus the ultrasound pulses along a desired scan line or to a desired voxel within the object being imaged). An input signal driving transducers of the transducer array can compensate for a frequency response of the transducer array to generate more constant frequency response for the transducer array. The transmitted ultrasound pulses in the method can correspond to any of the pulses shown in FIGS. 2 to 4B.

In block 1106, echoes are received along the scan line from the object being imaged. The frequency of the echoes together with their time delay from transmission may be used in determining the depth within the object being imaged from which the echoes originated.

In block 1108, a plurality of A-scan speckle images are generated. Each speckle image may have speckle that is generally independent of the speckle of the other speckle images, as each speckle image may be associated with a different imaging frequency. In some embodiments, block 1108 may involve analog and/or digital filtering of received echoes (such as echoes from a broadband pulse or echoes from multiple pulses at different frequencies) to generate multiple speckle images.

As indicated by line 1110, blocks 1102-1108 may be repeated for multiple A-scans (e.g., as the A-scan line is swept in direction in order to obtain a B-mode image).

In block 1112, A-scans are combined to generate a B-mode ultrasound image. The B-mode image may be stored in memory or storage and may be displayed or otherwise provided to a user. The B-mode image provided at block 1112 is a frequency-compounded image with reduced speckle. As an example, the B-mode image may be generated by compounding the A-scan speckle images and then merging the compounded A-scans and/or may be generated by merging the A-scan speckle images in a series of B-mode speckle images and then compounding the B-mode speckle images.

In at least some embodiments, the blocks of method 1100 may be performed at least partially in parallel. As an example, blocks 1104 and 1106 may be performed substantially in parallel to account for the round-trip time of the ultrasound pulses to and from the voxels being imaged.

V. An Ultrasound System with Frequency-Compounding

Figure 12:
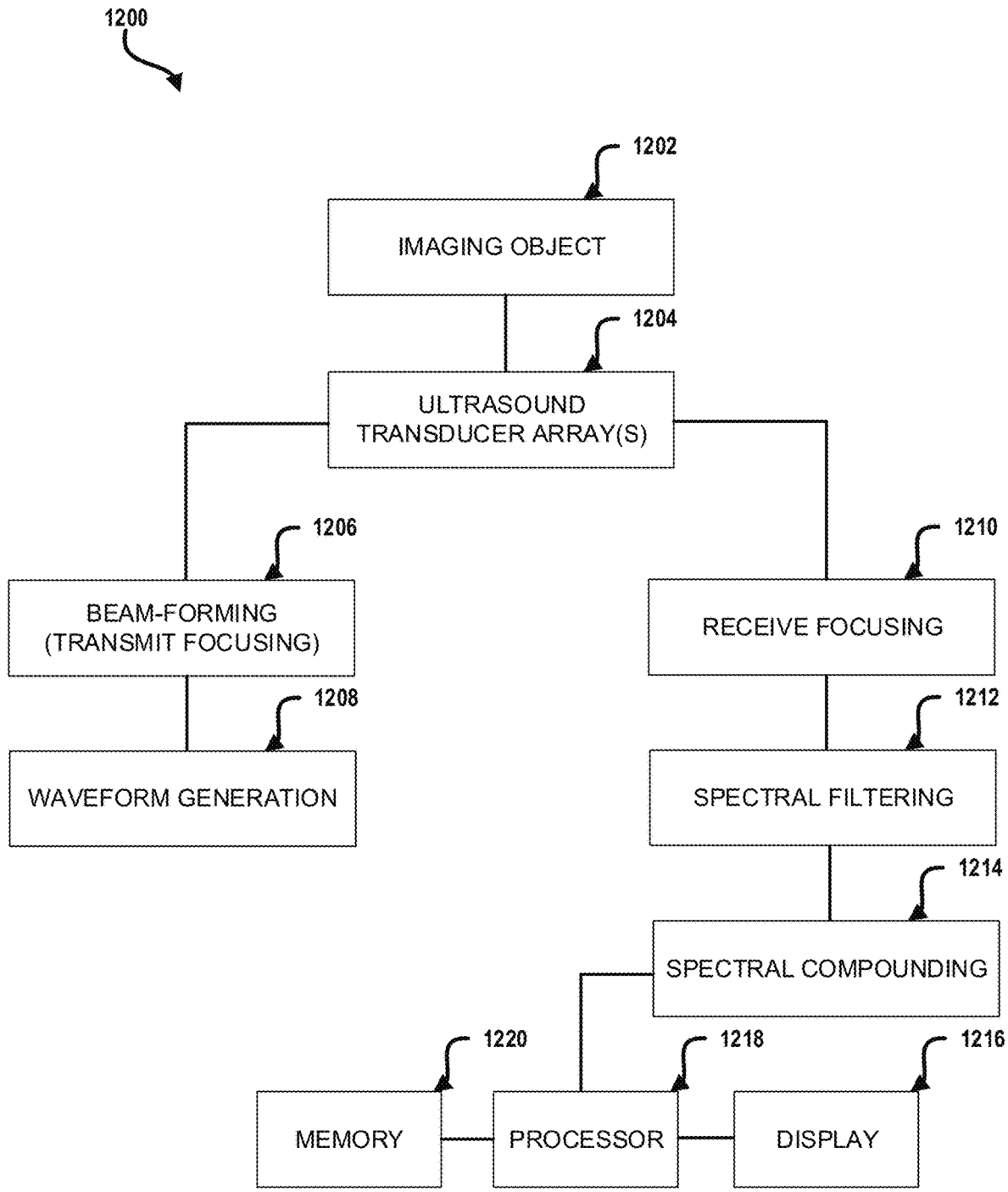
FIG. 12 is a block diagram of a system for ultrasonic imaging with frequency-compounding according to an embodiment of the disclosed technology.

FIG. 12 is a schematic block diagram of ultrasound imaging system 1200. The ultrasound imaging system 1200 can generate ultrasound images with reduced speckle via frequency-compounding. The system 1200 includes transducers 1204, which may include one or more transducer arrays such as a transmit array (which may be formed from elements 110 of FIG. 1A) and a receive array (which may be formed from elements 120 of FIG. 1A). The system also includes a processing circuit, such as processor 1218, arranged to generate an ultrasound image based on echoes received at the receive array.

The processing circuit, which may be a processor, can generate ultrasound images in accordance with any suitable principles and advantages disclosed herein. The processing circuit can perform a variety of signal processing functions such as frequency compounding, spatial compounding, voxel differentiation, filtering, or any other suitable processing functions for generating an ultrasound signal from received echoes. The processing circuit can include any suitable circuitry arranged to perform such signal processing. As illustrated, the processing circuit may include a receive focusing component 1210, a spectral filtering component 1212, a spectral compounding component 1214, and a processor 1218. The processing circuitry may also include waveform generation component 1208 and beam-forming component 1206.

The system 1200 can include one or more waveform generation components, such as wave form generation component 1208. The waveform generation component 1208 can generate the excitation signals used in exciting emissions from voxels of an object 1202 being imaged by the system 1200. The waveform generator 1208 can be used to generate a frequency modulated ultrasound signal (e.g., to facilitate distinguishing adjacent voxels, to facilitate frequency compounding, etc.) and can be used to generated a broadband ultrasound pulse.

Beam-forming component 1206 can apply beam-forming to the waveforms generated by component 1208. As an example, beam-forming component 1206 can cause the resulting ultrasound pulses to be properly steered such that the pulses excite the desired voxels at each stage of an imaging process.

Beam-forming is a technique used with antenna arrays for transmitting or receiving signals with a controllable directionality. The direction of signals transmitted by an array (or the sensitivity of the array to signals from a particular direction) is altered by adjusting signal delays for the various antenna elements that form the array, such that signals transmitted at or receive from desired angles experience constructive interference and signals outside those desired angles experience destructive interference. Beam-forming may be accomplished via hardware or software (e.g., by adjusting hardware delay elements or by delaying signals for particular antenna elements via software).

A transmitting array in ultrasound transducer array(s) 1204 can receive the beam-formed waveforms and transmit the excitation pulses into a medium being imaged by the system 1100. For example, the ultrasound transducer array(s) 1204 can send ultrasound pulses corresponding to any of the graphs of FIGS. 2 to 4B. A receiving array in ultrasound transducer array(s) 1204 can receive echoes from the excited voxels. In some embodiments, the transmitting and receiving arrays may be a single array whose duties are time-multiplexed between transmission and receiving functions. In other embodiments, the transmitting and receiving arrays may be distinct arrays. As described in connection with FIG. 1A, the transmitting and receiving arrays may have interleaved elements.

Receive focusing component 1210 can apply beam-forming to the echoes received by the various phased array elements of the receiving array, in order to implement receive focusing and focus on a particular voxel or region of the object being imaged by the system 1200. In at least some embodiments, receive beam-forming can be performed digitally (e.g., after digitization of the incoming signals, but before image formation). In at least some other embodiments, receive beam-forming may be performed on incoming analog signals prior to digitization.

Spectral filtering component 1212 can filter received echoes based on their frequencies, as part of generating a plurality of speckle images (e.g., images captured with different ultrasound frequencies. Component 1212 may, in some embodiments, generate speckle images.

Spectral compounding component 1214 may compound speckle images into a frequency-compounded ultrasound image. As an example, component 1214 may average together N speckle images, in order to reduce speckle by a factor of approximately $\sqrt{N}$. Spectral compounding component 1214 and/or spectral filtering component 1212 may digitize the incoming signals from the receive array and can integrate or combine signals received over time into an ultrasound image. The ultrasound image created by component 1214 may be a B-mode ultrasound image generated from the signals of individual voxels. In at least some embodiments, component 1214 may be a processor configured with software to digitize incoming signals and combine those signals into an ultrasound image. Components such as component 1214 may be coupled to memory 1220.

Display 1216 can visually present or otherwise provide the ultrasound image formed by component 1214 to a user. The display 1216 can be any suitable display arranged to visually present an ultrasound image, such as any of the ultrasound images shown in the drawings.

The ultrasound imaging system 1200 may include memory 1220. Memory 1220 may store constructed images, processing results, transmit and receive control instructions, beamforming parameters, and software instructions, as examples.

In embodiments discussed herein, frequency compounding can be applied to nonlinear ultrasound based on either frequency sum or frequency difference mixing. Instead of averaging of different harmonic orders, the averaging could also include averaging within the spectral window of each harmonic order.

Embodiments discussed herein can benefit from using parallel computation. The data recorded from each individual channel can be processed in parallel. The processing operations can include fast Fourier transform, spectral filtering, and envelope detection.

Embodiments described herein allow for real-time adjustment of the trade-off between speckle reduction and axial resolution. A user may choose to acquire a high resolution image with moderate speckle reduction, or a moderate resolution image with high speckle reduction.

VI. Nonlinear Ultrasonic Imaging Systems and Methods

Any of the principles and advantages of the frequency compounding disclosed herein can be applied to non-linear ultrasound imaging. Technology disclosed herein relates to acoustic frequency mixing, where sound at two frequencies interacts in a nonlinear medium to generate a third frequency. In certain embodiments, difference-frequency generation is used. Sum-frequency and/or higher-order nonlinear mixing can alternatively or additionally be used. For pulses with frequencies centered at $f_1$ and $f_2$, corresponding to wavelengths of $\lambda_1$ and $\lambda_2$, the nonlinear sound at the difference frequency has a central frequency $f_{NL}=|f_1-f_2|$ and a central wavelength $\lambda_{NL}$ satisfying $1/\lambda_{NL}=|1/\lambda_1-1/\lambda_2|$. The two pulses propagate non-collinearly, so that the nonlinear signal is only generated when the two pulses intersect in space and time, hence interrogating nonlinear acoustic response of the intersection voxel. The optimized resolution may be achieved when the two pulses intersect with an angle of approximately 90 degrees. Additionally, $\lambda_{NL}$ can be tuned by adjusting $\lambda_1$ and/or $\lambda_2$, allowing for further reduction in speckle by frequency compounding.

In at least some embodiments, the excitation frequencies are associated with ultrasound pulses that propagate non-collinearly, so that the nonlinear signal is only generated when the two pulses intersect. A coordinated sweep of the interacting pulses of the excitation frequencies allows for rapid imaging. Moreover, the nonlinear signal $\lambda_{NL}$ can be tuned by adjusting the excitation signals at wavelengths of $\lambda_1$ and/or $\lambda_2$, allowing for further reducing in speckle by frequency or spectral compounding.

One ultrasound imaging mode is the B-mode, where the brightness of a pixel represents the echogenicity, or the echo strength, of the corresponding voxel inside the tissue. The B-mode sound echo is created by changes in the acoustic impedance, given by the product of the density and velocity of sound. Tissue harmonic imaging can be used to improve the quality of B-mode images, making use of the harmonics generated as the fundamental wave propagates into the tissue. Since the harmonics are produced away from the surface, the reverberation effect is significantly reduced. Another advantage of tissue harmonic image is that the shorter wavelength of the harmonics results in better resolution than the fundamental (e.g., excitation) wavelength. While harmonic generation originates from the nonlinearity of the medium, the brightness of a pixel in the harmonic image is produced by the linearly back-scattered sound. As a result, the contrast of the harmonic images still represents the linear contrast.

The nonlinear frequency mixing is caused by a second-order change in density with respect to pressure. Hence, the nonlinear image is expected to have a different contrast than the linear image. Further, the contrast for certain anatomic features can be drastically enhanced.

As discussed above, ultrasound imaging is becoming an increasingly important tool for diagnostic imaging. Ultrasound imaging has many desirable characteristics, such as relatively fast, real-time imaging, low cost, and no exposure to ionizing radiation such as would be the case with x-ray diagnostics. However, ultrasound imaging can suffer from the presence of significant speckle noise (e.g., significant and widespread background noise in ultrasound images due to back-scattering of sound by the tissue being imaged). In clinical and other settings, the useful resolution of such ultrasound images can be degraded by the speckle noise.

Speckle noise can be the result of coherent back-scattering of sound by the distribution of scatterers within each scattering voxel. A voxel is the individual unit of spatial volume being imaged. In each voxel, suppose we have scattering amplitudes $A_1(\vec{x}_1)$, $A_2(\vec{x}_2)$, $A_3(\vec{x}_3)$, .... If these amplitudes interfere constructively or destructively, the scattered signal $|A_1(\vec{x}_1)+A_2(\vec{x}_2)+A_3(\vec{x}_3)+\ldots|^2$ can be either more or less than the sum of the scattering intensities of each of the scatterers, $|A_1(\vec{x}_1)|^2+|A_2(\vec{x}_2)|^2+|A_3(\vec{x}_3)|^2+\ldots$, thus producing speckle.

There are several approaches for speckle reduction. One method is to average over N independent speckle images, which can reduce the speckle by $\sqrt{N}$. The multiple images can be obtained by using different portions of an ultrasound array. In a linear array of total aperture length L, the resolution at any given depth z is approximately proportional to L/z. If the aperture is broken up into N sub-segments for the purposes of speckle reduction, the spatial aperture of each view is decreased by N and the resolution becomes (L/N)/z. Thus, this method of speckle reduction sacrifices both image acquisition time and spatial resolution. There are also post data-collection image processing algorithms. However, due to the randomness and high density of the speckle pattern, post data-collection algorithms in general have not been able to recover all the lost information hidden in the speckle image.

A system and a method for generating ultrasound images and contrast ultrasound images with reduced speckle is provided. The reduction of speckle can be achieved by detecting nonlinear ultrasound radiation generated from a localized spatial volume, such as a voxel, defined by the intersection of multiple excitation ultrasound pulses. The nonlinear ultrasound radiation can be generated at a difference frequency equal to a difference between the excitation ultrasound pulses. While various embodiments disclosed herein are described in connection with difference frequency signals, sum-frequency and/or higher-order nonlinear signals could be used instead of or in addition to difference frequency signals. The localized spatial volume is scanned by spatial scanning of the excitation ultrasound pulses to form the full image. In other words, the excitation ultrasound pulses are scanned over a desired area or volume to image a series of voxels and build up a full image of the area or volume. In at least some embodiments, increased wavelengths of the difference frequency ultrasound radiation reduce speckle.

This approach reduces speckle while preserving spatial resolution. Applications of the disclosed technology include, but are not limited to, medical diagnostic ultrasound imaging.

New methods and devices for ultrasound imaging with significantly reduced speckle level are disclosed herein. The methods and devices utilize acoustic difference-frequency generation in which sound at two excitation frequencies interacts in a nonlinear medium to generate an ultrasound return signal at a third frequency, which is equal to the difference of those two frequencies. Consider the case of two excitation frequencies centered at $f_1$ and $f_2$, corresponding to wavelengths of $\lambda_1$ and $\lambda_2$, respectively. The nonlinear difference-frequency return signal has a central wavelength $\lambda_{NL}$ satisfying $1/\lambda_{NL}=1/\lambda_1-1/\lambda_2$. From this relation, one can see that $\lambda_{NL}$ is longer than the wavelengths $\lambda_1$ and $\lambda_2$. Advantageously, one can choose $\lambda_1$ and $\lambda_2$ and the imaging configuration, such that the wavelength of the nonlinear signal $\lambda_{NL}$ is significantly greater than the image voxel's dimension. As a result, one may expect that the generated nonlinear amplitudes in each voxel have essentially the same phase and constructively interfere. However, due to the interference fringes within the voxel, speckle is not completely eliminated, but there can be a finite suppression in speckle. Speckle suppression can be further improved by compounding images corresponding to a number of difference-frequencies.

VII. An Example Embodiment of Nonlinear Ultrasound Imaging

Figure 13A:
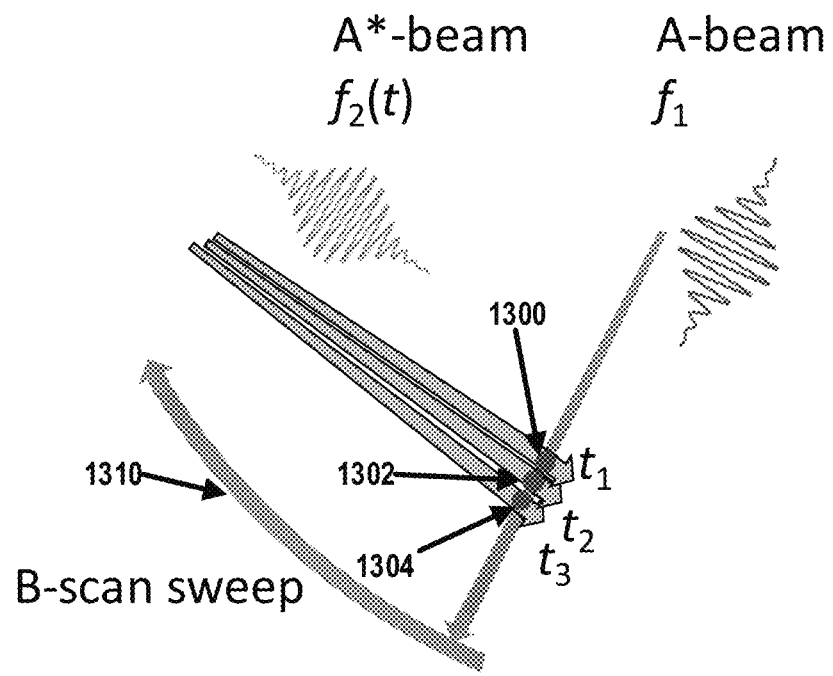
FIG. 13A illustrates intersecting ultrasonic pulses for an A-scan utilizing intersecting beams and also illustrates how a B-scan image can be formed with a sweep of the intersecting beams according to an embodiment of the disclosed technology.

In an example embodiment, an imaging voxel is defined by two excitation beams, such as the A and A* beams of FIG. 13A generated by first and second transducers such as transducer arrays 1502 and 1504 of FIG. 3A, intersecting in both space and time. The A-beam can have a frequency $f_1$ and the A*-beam can have a frequency $f_2(t)$. In each line scan, the A-scan transmitter emits an acoustic Fourier-transform limited Gaussian pulse of duration $\Delta t$ $$g(t) = \frac{1}{(2\pi\sigma^2)^{\frac{1}{2}}}\exp\left[-\frac{t^2}{2\sigma^2}\right], \quad (1)$$

$$\Delta t \Delta \omega = 1,$$

where $\Delta\omega=2\pi\Delta f$ and $\Delta t$ are the 1 σ widths of the Gaussian Fourier transforms, respectively. The full-width at half maximum of the pulse $\Delta t_{FWHM}=2.35\Delta t$. The A*-beam can be swept in direction using a phased array, so that its focus continually intersects the A-beam as the A-beam penetrates into tissue.

FIG. 13A illustrates an A-beam intersecting a sweeping A*-beam at different points in time and space. An angle between the A-beam and the A*-beam can be approximately 90 degrees. The angle between the A-beam and the A*-beam can be in a range from about 40 degrees to 140 degrees in certain applications. As illustrated in FIG. 13A, the A*-beam can be swept in direction such that it intersects the A-beam at voxels 1300, 1302, and 1304. Detection of an echo at a difference frequency at different time delays corresponds to different z-positions along a scan line of the A-scan. A B-scan image can be formed by the coordinated sweep of the A- and A*-beams. A processing circuit of the ultrasound imaging system can image the nonlinear response from the voxels 1300, 1302, and 1304. After the A* beam has scanned along the length of the A-beam (within the desired depths of the object being imaged), the A beam can be stepped to another direction such as along the B-scan sweep 1310 such that additional voxels (e.g., voxels adjacent to voxels 1300, 1302, and 1304) can be imaged. In this manner, the system can obtain a B-scan of the object being imaged.

In some other embodiments, the A-beam may be scanned along the A* beam, and the A*-beam may be sweep across the B-scan sweep 1310. In still other embodiments, the A-beam and the A*-beam may be swept independently, in unison, or in any other manner in order to move the actively imaged voxel around within the object being imaged in any desired manner.

Figure 13B:
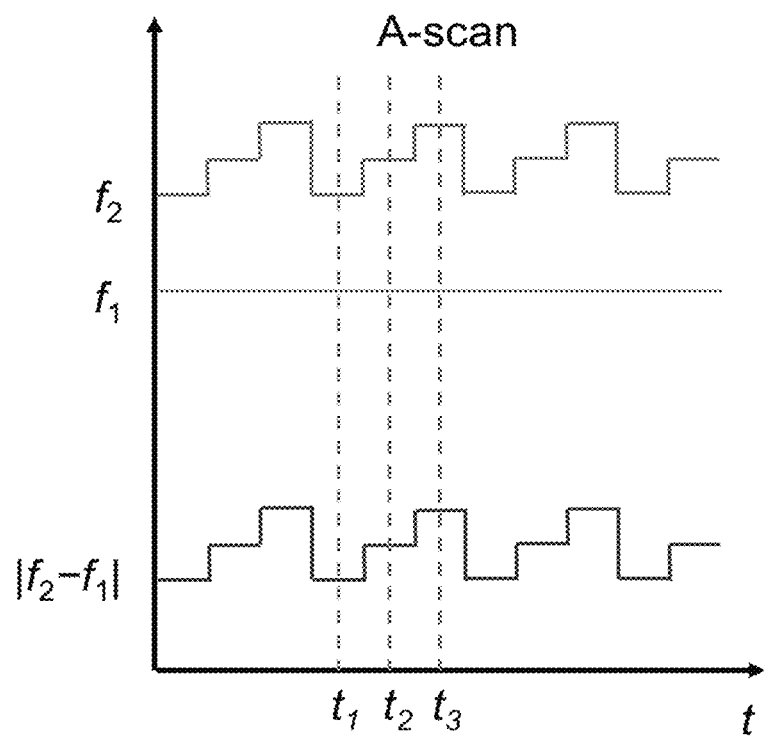
FIG. 13B illustrates frequencies of the ultrasonic pulses of the intersecting beams of FIG. 13A and of echoes as a function of time according to an embodiment of the disclosed technology.

To avoid coherent interference of the nonlinear signal generated in adjacent voxels, the frequency $f_2(t)$ of the A*-beam may vary over time. In particular, the frequency $f_2(t)$ of the A*-beam may be switched between two or more discrete frequencies as it is swept in direction. FIG. 13B illustrates one example of how the frequency $f_2(t)$ of the A*-beam may be switched between three center frequencies. Shifting the frequency of the A*-beam in this manner can allow digital filtering of the different difference-frequencies, such that adjacent voxels can be easily distinguished. As an example, voxel 1300 may be excited with the A-beam at a first sub-frequency of $f_2$ and the A-beam at frequency $f_1$, while voxels 1302 and 1304 may excited with the A*-beam modulated to a second sub-frequency of $f_2$. The A*-beam may excite voxels 1300, 1302, and 1304 in this manner by emitting a series of pulses at different center frequencies, as illustrated in FIG. 13B, each of which is timed to intersect with a corresponding pulse from the A-beam at a desired depth (e.g., at a desired voxel) within the object being imaged. With this arrangement, voxels 1300, 1302, and 1304 respectively generate nonlinear return signals having frequencies at the difference between $f_1$ and either the first, second, or third sub-frequency of $f_2$. These return signals can be distinguished by any desired filtering techniques. The switching of the center frequencies of the A*-beam may be achieved by programming the output of an arbitrary waveform generator.

FIG. 13B shows center frequencies of the A-beam, A*-beam, and their difference-frequency as a function of time at the location of their intersection. As shown in FIG. 13B, the A-beam can be constant and centered at $f_1$. The A*-beam can switch its center frequency among three frequencies as shown in FIG. 13B. The A*-beam can be modulated to have two or more frequencies. Alternatively, the A-beam can be modulated in frequency and the A*-beam can be modulated in frequency to generate a different difference-frequencies in adjacent voxels along a scan line.

The technique of FIGS. 13A and 13B may enable nonlinear ultrasound systems to obtain ultrasound images in real-time at rates comparable to linear ultrasound systems. In particular, the nonlinear ultrasound systems disclosed herein may be able to obtain ultrasound images at a frame rate of at least 1 Hz, at least 5 Hz, at least 10 Hz, at least 20 Hz, or at least 30 Hz. Additionally, the systems may capture nonlinear ultrasound images of at least 100 by 100 pixels, at least 200 by 200 pixels, or at least 400 by 400 pixels and may capture such images at a real-time frame rates such as at least 1 Hz, at least 5 Hz, at least 10 Hz, at least 20 Hz, or at least 30 Hz. The relatively high rate of imaging may be enabled by the rapid sweep of the A* beam along the scan line. In particular, the imaging rate of linear ultrasound systems may be limited by the round-trip propagation time of ultrasound pulses along a given scan line of the A-beam. To build an entire image, the A-beam may have to sweep along the B-scan sweep line (such as line 1310 of FIG. 13A) and the A-beam may have to linger at each scan line for the round-trip propagation time. With the present nonlinear system, the A*-beam may sweep along the A-beam over approximately the round-trip propagation time. Thus, the A-beam may be able to sweep along the B-scan sweep line 1310 at approximately the same rate in linear and nonlinear imaging modes and the nonlinear ultrasound imaging systems disclosed herein can provide a relatively high frame rate B-mode imaging.

The difference frequency sound can be detected by a third transducer, such as elements 1506 of transducer probe 1500 of FIG. 3A, which is sensitive to the difference frequencies. An analog filter can be used to attenuate background away from the difference frequency bands. After amplification of the nonlinear signal, the voltage signal can be digitized. To determine the signal from a voxel at depth z along the line scan, the digitized signal can be analyzed in a time window centered at the corresponding time delay, which can be expressed as $t=(z+z')/c$, where $z'$ is the distance from the imaging voxel to the detector and c is the speed of sound. The time window has a duration given approximately by the voxel depth divided by the speed of sound.

Further filtering in the frequency domain can be performed by digital Fourier transformation of the time domain signal and then selecting the frequency band in the frequency domain as discussed above. The nonlinear signal can be obtained by integrating the resulting difference frequency intensity.

With the methods corresponding to FIGS. 13A and 13B, the speed of data acquisition is not compromised compared to a conventional scan since the A-scan time is still determined by the traveling time of the acoustic pulse through the depth of the scan range. The A* transducer can emitting a continuous stream of ultrasound pulses during the transit time of the A-scan.

Figure 13C:
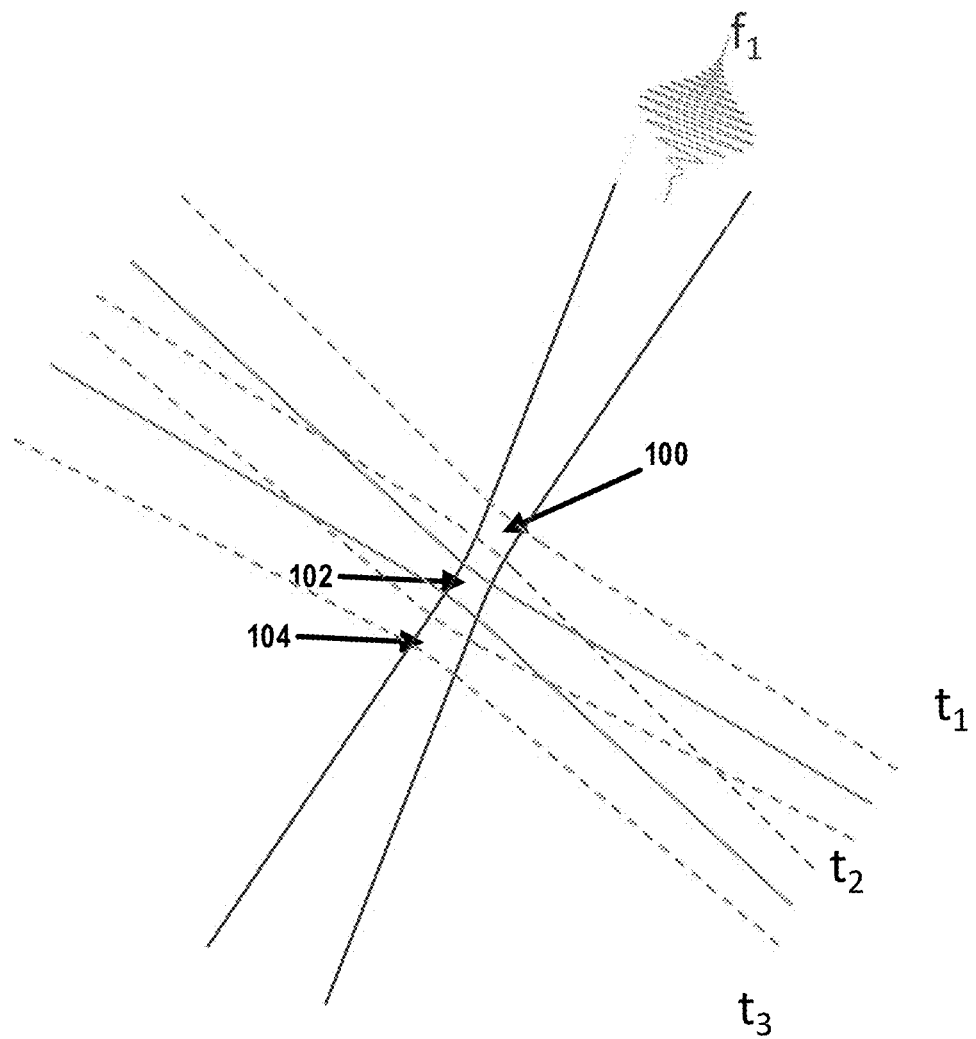
FIG. 13C illustrates ultrasonic pulses intersection at a plurality of voxels according to an embodiment of the disclosed technology.

FIG. 13C illustrates ultrasonic pulses intersection at a plurality of voxels according to an embodiment of the disclosed technology. During a single pulse of a first transducer transmitting an ultrasound signal at frequency $f_1$, a second transducer transmitting an ultrasound signal at frequency $f_2$ can be swept in position so that it intersects with the first ultrasound signal at time resolved points $t_1$, $t_2$, $t_3$, etc. As shown in FIG. 13C, to optimize the nonlinear signal and minimize voxel size, focused phased arrays can be used to change the focal spots at $f_1$ and $f_2$ for each successive pulse of the second ultrasound signal. FIG. 13C also illustrates voxels 1300, 1302, and 1304, which may be various localized spatial volumes within a larger object that is being imaged by the system.

Figure 13D:
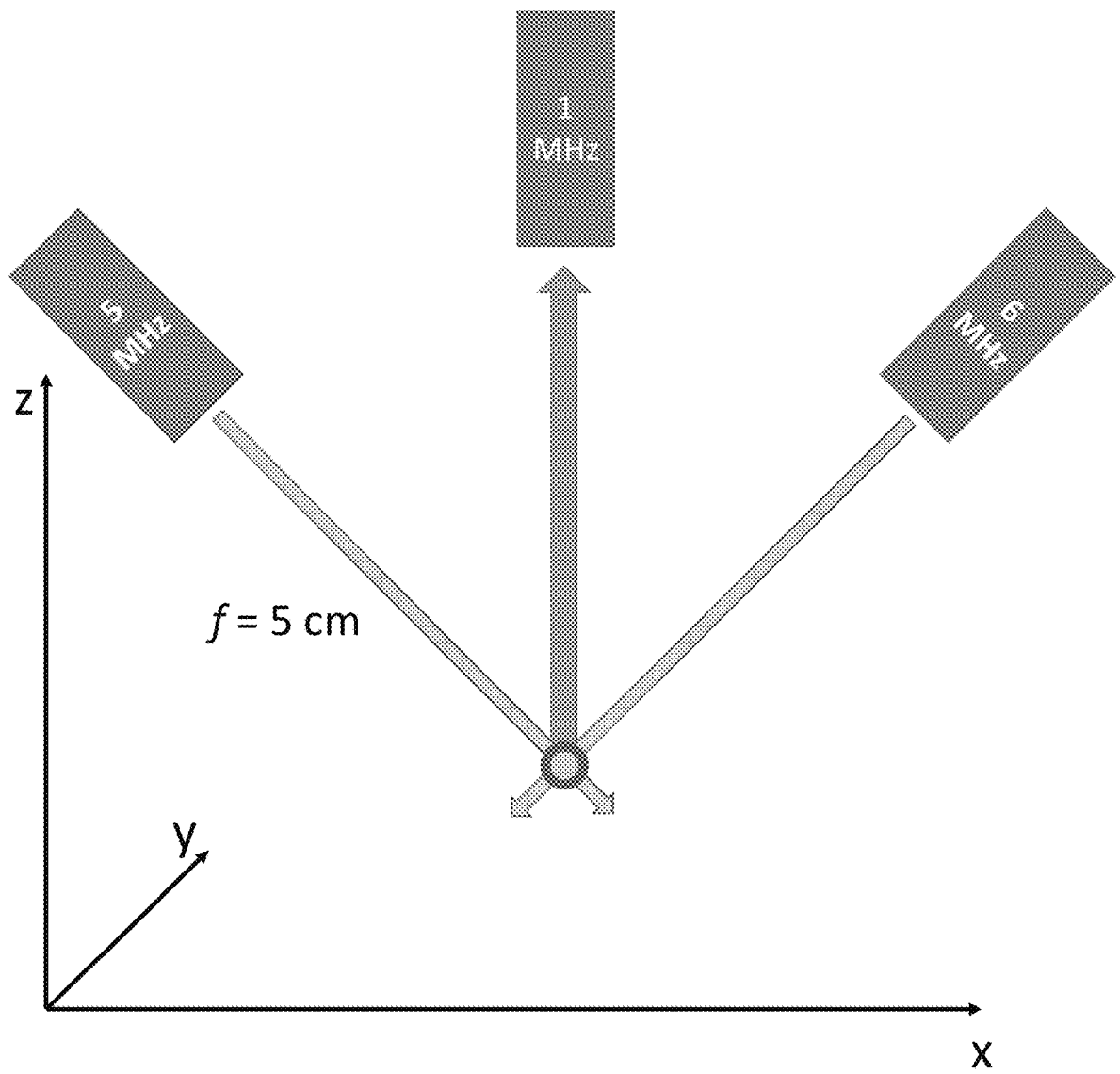
FIG. 13D illustrates transducers arranged to transmit ultrasound signals having different frequencies and another transducer arranged to receive echoes associated with interaction of the ultrasound signals from the transducers according to an embodiment of the disclosed technology.

FIG. 13D illustrates transducers arranged to transmit ultrasound signals having different frequencies and another transducer arranged to receive echoes associated with interaction of the ultrasound signals from the transducers according to an embodiment of the disclosed technology. As shown in FIG. 13D, a first transducer is arranged to transmit an ultrasound signal having a frequency 5 MHz and a second transducer is configured to transmit an ultrasound signal having a frequency of 6 MHz. A third transducer is arranged to detect a difference-frequency signal having a frequency of 1 MHz associating with interaction of the ultrasound signals from the first and second transducers in a voxel at which they intersect in space and time.

VIII. Frequency Compounding in Nonlinear Ultrasound Imaging

Frequency compounding can be applied to nonlinear contrast imaging to reduce speckle. A refined speckle reduction scheme that involves frequency compounding that may not reduce the frame rate can be applied to nonlinear contrast imaging. As an example, N A-pulses are sent out sequentially during one A-scan for an N-fold frequency compounding. The A-pulses are delayed by one imaging voxel. N trains of A*-pulses are transmitted to intersect with the N A-pulses to generate the difference frequency signal. For the purpose of illustration, let us consider the case for N=3. The three A-pulses are centered at $f_1$. The three A*-pulse trains have center frequencies $f_2$, $f_2'$, and $f_2''$, respectively. Each A* pulse train traces one of the A-pulses, generating difference frequencies centered at $|f_2-f_1|$, $|f_2'-f_1|$, and $|f_2''-f_1|$, respectively.

Table 1 summarizes the nonlinear frequency generation at different imaging depth and time delays. At the receiving end, multiple frequencies are detected as a function of time delay. Digital frequency filtering and receive focusing allows for the separation of the frequencies (and thus different depths). For example, at time $t_0$, the signal detected will be from depth $t_0c$ at frequency $|f_2-f_1|$, from depth $(t_0-\Delta t)c$ at frequency $|f_2'-f_1|$, and from depth $(t_0-2\Delta t)c$ at frequency $|f_2''-f_1|$. At time $t_0+\Delta t$, signal at $|f_2'-f_1|$ from depth $t_0c$ is detected. With this scheme, each voxel is imaged at N difference frequencies in one A scan, and hence the frame rate is maintained. Compounding N nonlinear frequency bands reduces speckle by a factor of $\sqrt{N}$.

the table may be the nonlinear frequencies emitted from the corresponding imaging voxels and the time delays.

Figure 14:
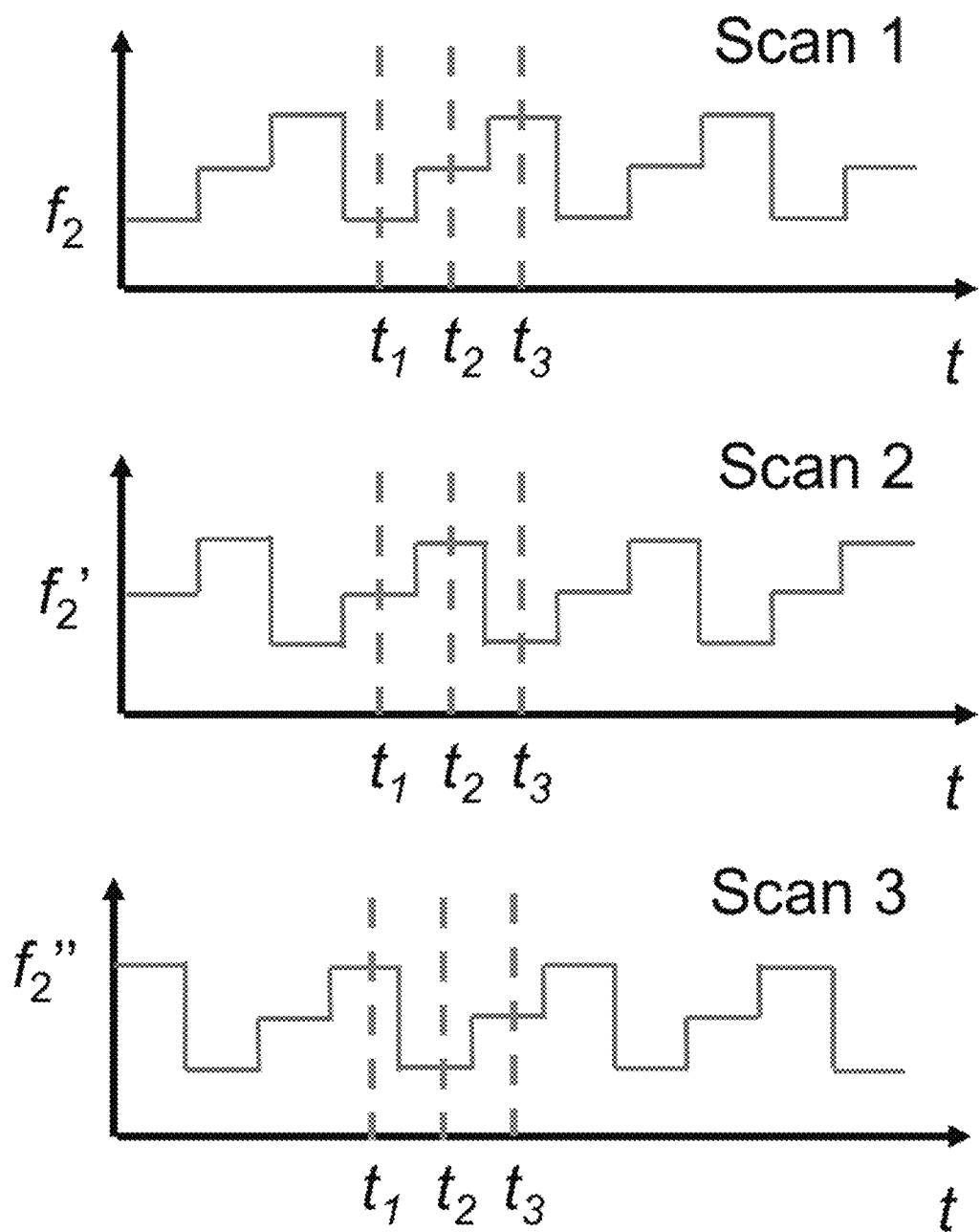
FIG. 14 illustrates graphs of ultrasonic pulses of the one of the beams of FIG. 13A for three scans that can form a basis for frequency compounding according to an embodiment of the disclosed technology.

Graphs illustrating an example of the frequency compounding scheme for N=3 are shown in FIG. 14. To further improve speckle suppression, additional A-scans can be made where the frequency is shifted step-wise in time so that at each depth $z(t_1, f_2)$ along a scan line the frequency $f_2$ is shifted to $f_2'$ and then to $f_2''$ for 3 successive A-scans. Multiple nonlinear bands are then produced at $f_{NL}=|f_2-f_1|$, $|f_2'-f_1|$, $|f_2''-f_1|$, . . . . The frequency bands in the A*-beam can be separated to allow the nonlinear bands to be distinguished with digital filtering. In other words, each of the frequencies $f_2(t)$, $f_2'(t)$, and $f_2''(t)$ of the A*-beam may be switched between two or more frequencies to facilitate distinguishing echoes from adjacent voxels, for example, as described in connection with FIGS. 13A and 13B. Compounding of these nonlinear frequency bands may further reduce speckle by a factor of $\sqrt{N}$, where N is the number of nonlinear bands.

Figure 20:
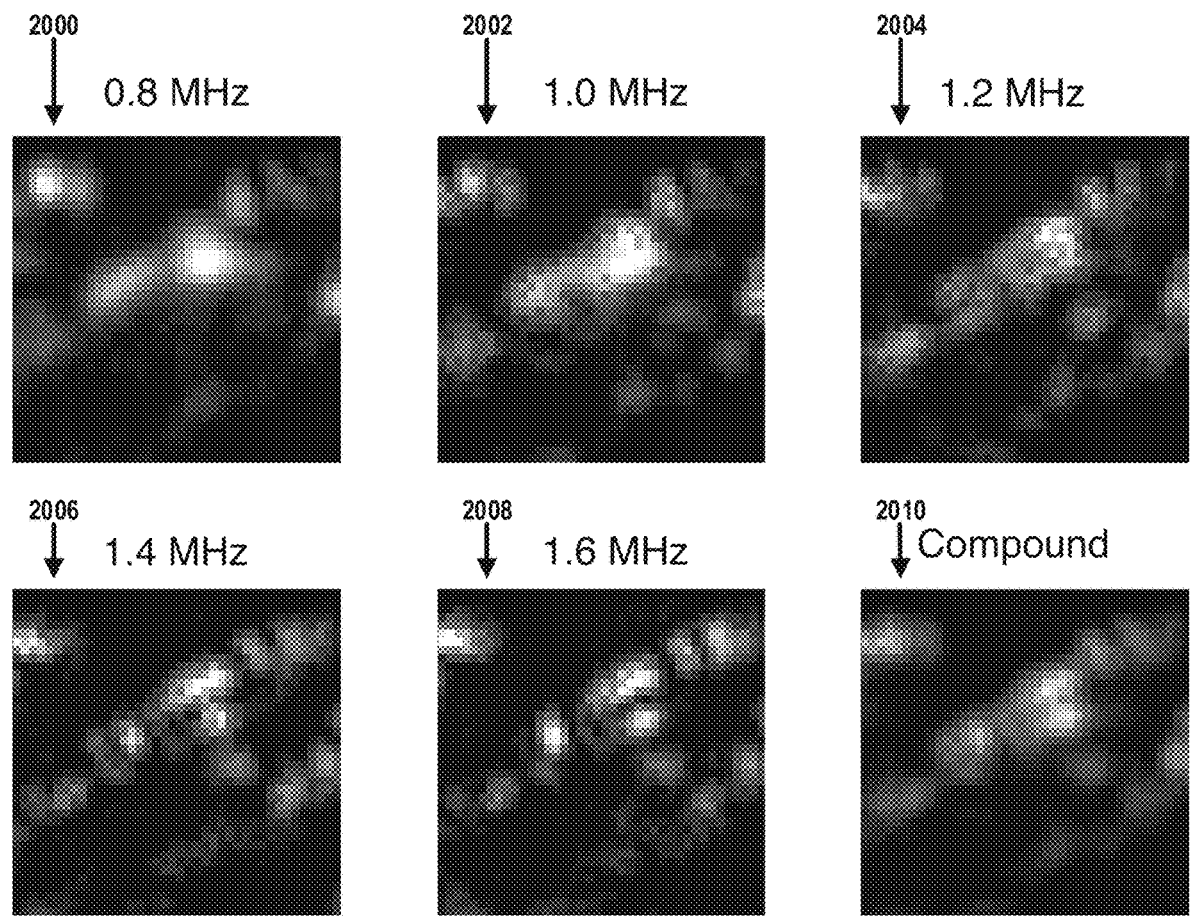
FIG. 20 illustrates nonlinear ultrasonic images obtained at varying difference-frequencies and a compound image obtained from the nonlinear ultrasonic images according to an embodiment of the disclosed technology.

As shown in FIG. 20, the system can obtain difference-frequency images such as images 2000, 2002, 2004, 2006, and 2008 at multiple difference-frequencies and can then compound the different images into compound image 2010 to further suppress residual speckle and noise. The system can tune or vary the difference-frequency for each of the difference-frequency images (e.g., nonlinear ultrasonic images) by varying one or both of the excitation frequencies. Image 2002 of FIG. 20 corresponds to the nonlinear image 1704 of the 1 cm by 1 cm section of the salmon tissue sample from FIG. 17A. As shown in FIG. 20, compound image 2010 exhibits a lower degree of speckle, especially compared to the images 2006 and 2008 at 1.4 MHz and 1.6 MHz, respectively. The improvement demonstrates the usefulness of frequency compounding to further suppress residual speckle.

Figure 25:
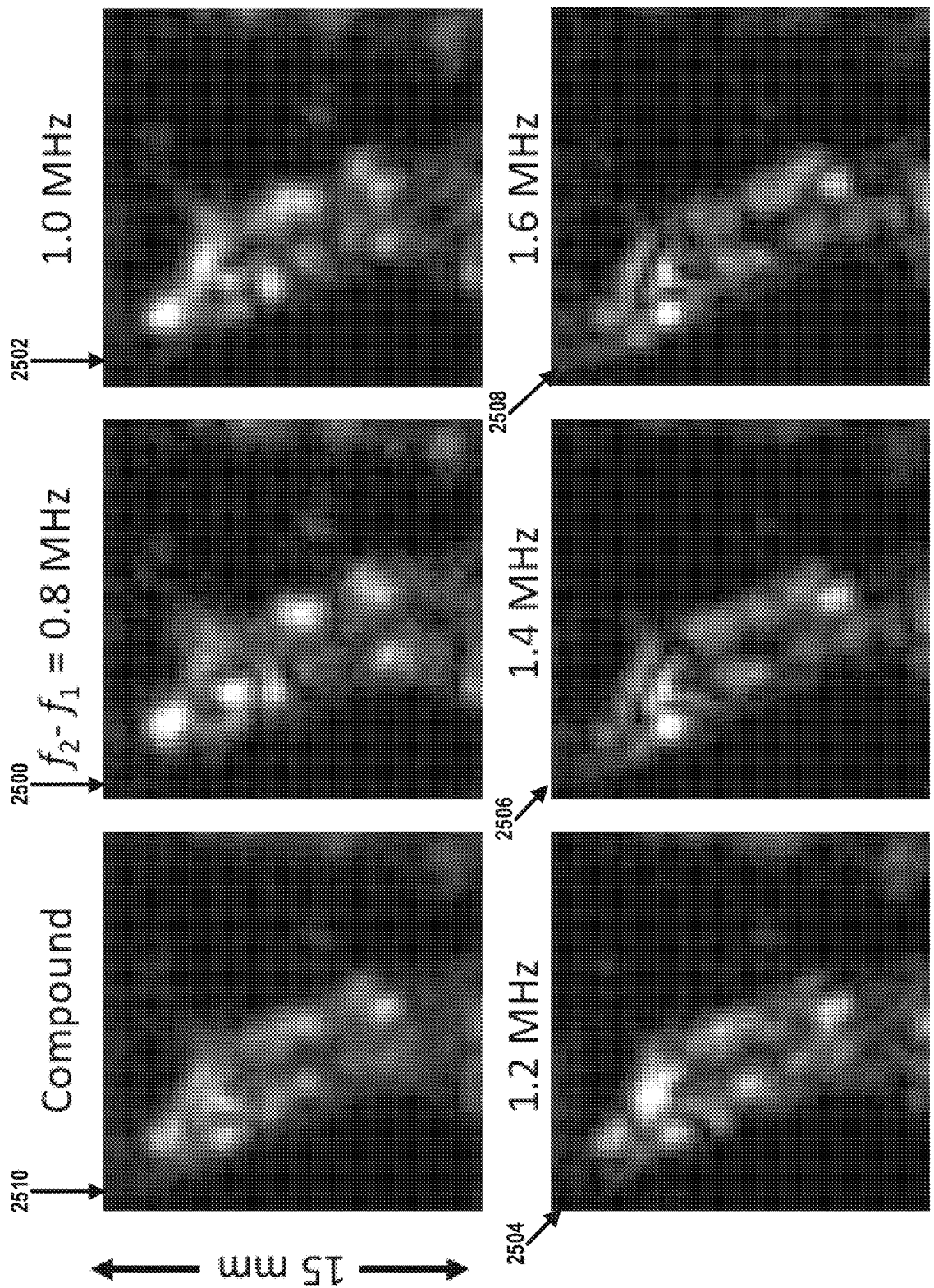
FIG. 25 illustrates nonlinear ultrasonic images of the pig kidney tissue of FIG. 24 obtained at varying difference-frequencies and a compound image obtained from the nonlinear ultrasonic images according to an embodiment of the disclosed technology.

Another example of how the nonlinear ultrasound imaging systems can benefit from frequency or spectral compounding is shown in FIG. 25. As shown in FIG. 25, the system can obtain difference-frequency images such as images 2500, 2502, 2504, 2506, and 2508 at multiple difference-frequencies (e.g., by tuning one or both of the excitation frequencies) and can then compound the different images into compound image 2510 to further suppress residual speckle and noise. As shown in FIG. 25, compound image 2510 exhibits a lower degree of speckle, especially

TABLE 1

Frequency compounding scheme that may not reduce the frame rate. The rows may correspond to imaging voxels (Δtc is the voxel size) at different depths and the columns correspond to different time delays. The entries in the table may be the nonlinear frequencies emitted from the corresponding imaging voxels and the time delays.

|  | . . . $t_0$ | $t_0 + \Delta t$ | $t_0 + 2\Delta t$ | $t_0 + 3\Delta t$ | $t_0 + 4\Delta t$ | . . . |
|---|---|---|---|---|---|---|
| $(t_0 - 2\Delta t)c$ | . . . $|f_2'' - f_1|$ | | | | | |
| $(t_0 - \Delta t)c$ | . . . $|f_2' - f_1|$ | $|f_2'' - f_1|$ | | | | |
| $t_0c$ | $|f_2 - f_1|$ | $|f_2' - f_1|$ | $|f_2'' - f_1|$ | | | |
| $(t_0 + \Delta t)c$ | | $|f_2 - f_1|$ | $|f_2' - f_1|$ | $|f_2'' - f_1|$ | | |
| $(t_0 + 2\Delta t)c$ | | | $|f_2 - f_1|$ | $|f_2' - f_1|$ | $|f_2'' - f_1|$ | |
| $(t_0 + 3\Delta t)c$ | | | | $|f_2 - f_1|$ | $|f_2' - f_1|$ | . . . |
| $(t_0 + 4\Delta t)c$ | | | | | $|f_2 - f_1|$ | . . . |

Table 1: Frequency compounding scheme that may not reduce the frame rate. The rows may correspond to imaging voxels (Δtc is the voxel size) at different depths and the columns correspond to different time delays. The entries in compared to the images 2506 and 2508 at 1.4 MHz and 1.6 MHz, respectively. The image 2502 obtained with a difference frequency of 1.0 MHz corresponds to image 2404 of FIG. 24.

IX. Spatial Compounding in Nonlinear Ultrasound Imaging

Spatial compounding of the nonlinear signal can be performed by averaging the images of a region from a number of different angles. An M-fold spatial compounding reduces speckle by up to a factor of $\sqrt{M}$. Frequency and spatial compounding can be combined to achieve a speckle reduction of up to a factor of $\sqrt{MN}$, where N denotes the number of different frequencies compounded together.

In at least some embodiments, spatial or angular compounding can include determining the positions and/or orientations of the nonlinear ultrasound detectors (and even the emitters of the A and A* beams) relative to the subject being imaged for each of the nonlinear images compounded together. The position and/or orientation information may be used by the system in the process of compounding individual ultrasound images (e.g., by registering two or more ultrasound images to each other). When spatially compounding M nonlinear ultrasound images taken by the system from up to M different positions, the system may track the positions of the detectors (and/or emitters) relative to the subject being imaged. Alternatively or in additionally, the system may be able to determine relative positions of a detector (and/or emitter) and the subject being imaged after capturing two or more ultrasound images (e.g., by correlating the images with each other to determine the angular and spatial changes of the detectors between each of the ultrasound images). If desired, the ultrasound system may include inertial sensors, or any other desired position sensors, that provide positional and angular tracking data such that ultrasound images can be compounded together.

Figure 15A:
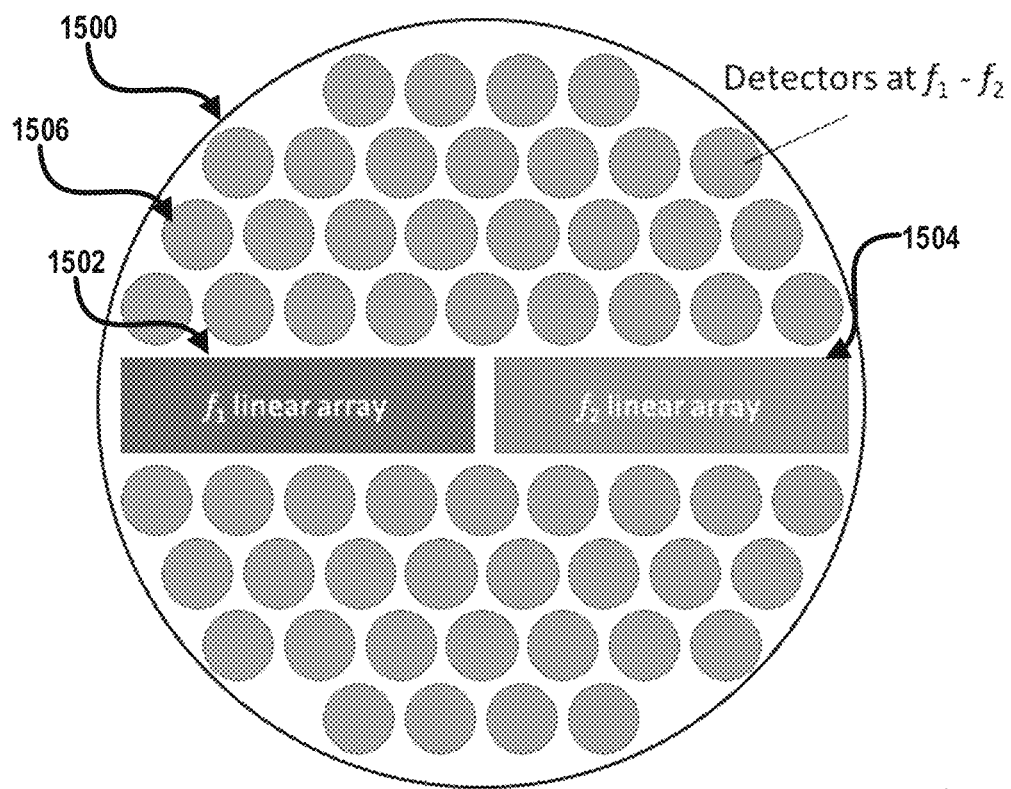
FIG. 15A illustrates an ultrasonic transducer probe that includes two linear arrays that can transmit the intersecting beams of FIG. 13A and an array of transducer elements that can receive ultrasonic return signals according to an embodiment of the disclosed technology.

X. Example Embodiments of an Integrated Transducer Probe for Nonlinear Ultrasound Imaging FIG. 15A illustrates an embodiment of an integrated transducer probe 1500 that can generate the excitation beams, such as the A and A* beams of FIGS. 13A, 13B, 13C, and/or 14 and that can also receive a nonlinear ultrasound return signal. The transducer probe 1500 can include two or more linear phased arrays, such as arrays 1502 and 1504, which may be used for transmitting the A- and A* excitation beams. The array 1502 is a first transducer arranged to transmit an ultrasound signal, such as an A-beam of FIG. 13A. The array 1504 is a second transducer arranged to transmit a second ultrasound signal, such as the A*-beam, having a different frequency than the first ultrasound signal. Each phased array 1502 and 1504 can include multiple individually addressable piezoelectric transducer elements. In various embodiments, the spacing between phased arrays 1502 and 1504 may be varied in order to vary the intersection angle of the excitation beams. In general, wider spacing of the phased arrays 1502 and 1504 can enable the excitation beams to intersect over a smaller volume, decreasing the size of the voxel and increasing resolution of the system. If desired, a non-integrated transducer probe may be provided to facilitate wide separation of the arrays generating the excitation beams. In at least some embodiments, the axial and lateral resolution of the system may be optimized when the excitation beams intersect at approximately a 90 degree angle.

As shown in FIG. 15A, the integrated transducer probe 1500 can include transducer elements 1506, which are configured to detect the difference-frequency signals (e.g., the nonlinear ultrasound return signals). FIG. 15A illustrates transducer elements 1506 as round. However, in general, transducer elements such as the elements forming 1502, 1504, and 1506 may be any desired shape. In some embodiments, the element size for detecting the difference-frequency signal, such as the size of elements 1506, may be larger than the element size for transmitting the excitation beams, such as the size of elements 1502 and 1504, which may allow for efficient detection of the longer wavelength at the difference-frequencies. The distribution of the detected signal over the circular elements can be used to further acquire the angular distribution of the nonlinear radiation from each voxel, which in turn gives information about the anisotropy of linear and nonlinear elasticity. The receive aperture may be divided into several sub-apertures, and the signals of the sub-apertures may be obtained separately and averaged to reduce speckle. In an alternative embodiment, the hexagonal receive array 1506 of FIG. 15A may be replaced by a linear detector array that is placed in between the two transmission arrays 1502 and 1504.

The difference frequency sound is detected by a third transducer, such as elements 1506 of transducer probe 1500, which is sensitive to the difference frequencies. Analog filters can be used to attenuate background away from the difference frequency bands. After amplification of the nonlinear signal, the voltage signal can be digitized. To determine the signal from a voxel at depth z along the line scan, the digitized signal can be analyzed in a time window centered at the corresponding time delay, which can be expressed as $t=(z+z')/c$, where $z'$ is the distance from the imaging voxel to the detector and c is the speed of sound. The time window has a duration given approximately by the voxel depth divided by the speed of sound.

Further filtering in the frequency domain can be performed by digital Fourier transformation of the time domain signal and then selecting the frequency band in the frequency domain as discussed above. The nonlinear signal can be obtained by integrating the resulting difference frequency intensity. The speed of data acquisition is not compromised compared to conventional scan since the A-scan time is still determined by the traveling time of the acoustic pulse through the depth of the scan range. Note that the A* transducer may be emitting a continuous stream of ultrasound pulses during the transit time of the A-scan.

Figure 15B:
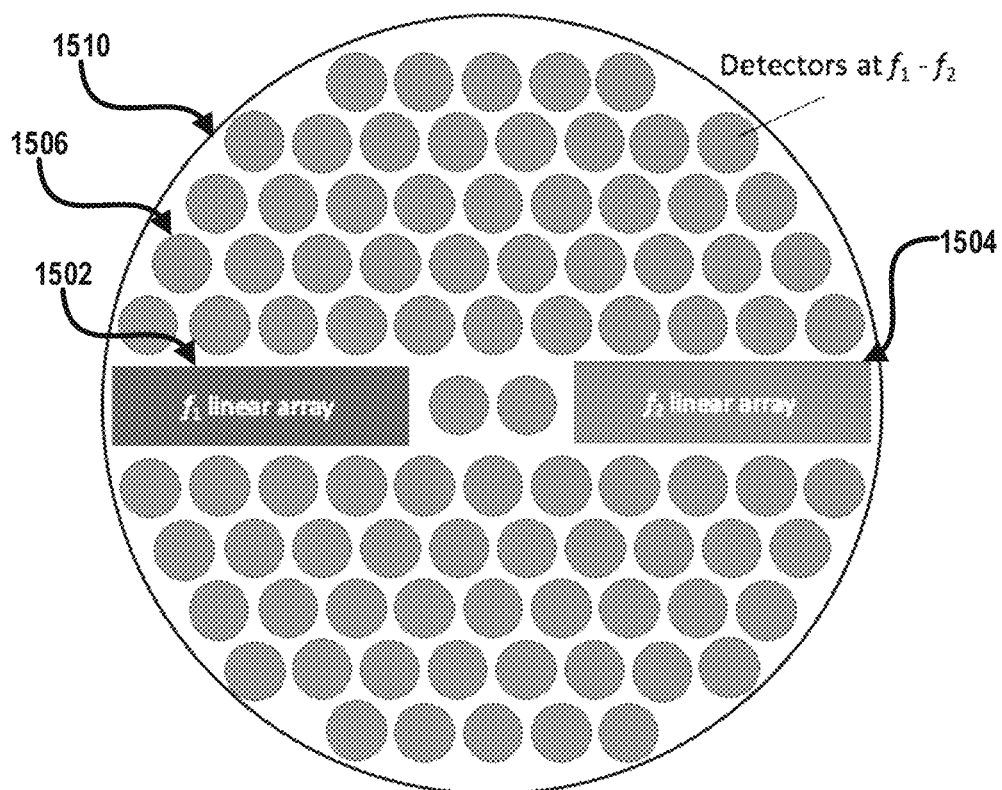
FIG. 15B illustrates another ultrasonic transducer probe that includes two linear arrays that can transmit the intersecting beams of FIG. 13A and an array of transducer elements that can receive ultrasonic return signals according to an embodiment of the disclosed technology.

FIG. 15B illustrates another embodiment of an integrated transducer probe 1510, in which the two linear phased arrays 1502 and 1504 are separated. The integrated transducer probe 1510 is similar to the integrated transducer probe 1500 of FIG. 15A, except that the angle between the intersecting beam is increased, which can improve axial resolution when imaging at greater depths. Transducer elements 1506 are also included between the linear phased arrays 1502 and 1504 in the integrated transducer probe 1510.

In other embodiments, the excitation beams A and A* may be generated by a single integrated array of ultrasound transducers, which may or may not be a phased array. In other words, the linear phased arrays 1502 and 1504 may be integrated together. In such embodiments, the integrated array may be able to generate the excitation beams A and A* not only with different angles but from different regions of the integrated array, such that the beams intersect each other at some point within the volume being imaged by the system. If desired, one or both of the linear phased arrays 1502 and 1504 of an integrated array may be provided in a non-linear shape, such as a planar or circular array, which enables the origin points of the beams to be rotated (alternative, transducer probes such as head 1500 and 1510 can be rotated in place to achieve a similar effect). In at least some embodiments, the system may receive nonlinear ultrasound signals using receive transducers that are also used in generating one or both of the excitation beams.

XI. Prototype Nonlinear Ultrasound Imaging System and Results

Figure 16:
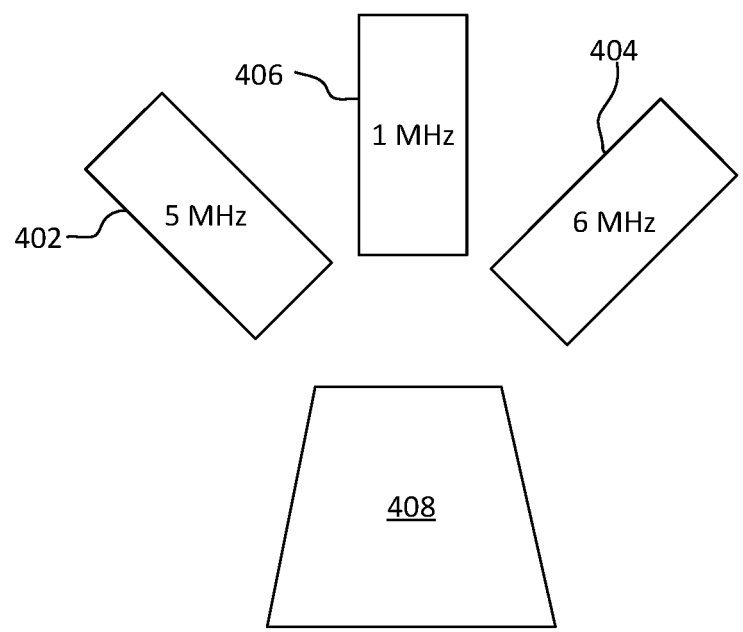
FIG. 16 illustrates a system including multiple ultrasonic transducers for transmitting the intersecting beams of FIG. 13A and receiving ultrasonic return signals according to an embodiment of the disclosed technology.

FIG. 16 illustrates a prototype system 1600 for nonlinear ultrasonic imaging using disclosed methods, such as the techniques described in connection with FIGS. 13A-15B. As shown in FIG. 16, ultrasound radiation at 5 MHz and 6 MHz (e.g., $f_1$ and $f_2$) is produced by two piezoelectric transducers 402 and 404, respectively. The center frequencies of the pulses can be controlled by the electrical pulses produced by two arbitrary waveform generators. The electrical pulses at the designated center frequencies can be amplified and can drive the transducers. The acoustic pulses emitted by the two transducers 402 and 404 intersect in both space and time. The intersection of the two excitation beams from transducers 402 and 404 defines an imaging voxel. A difference-frequency signal at $f_{NL}=f_1-f_2=1$ MHz is created in this voxel by the mixing of the two beams from transducers 402 and 404. The difference-frequency signal can be detected with the third piezoelectric transducer 406.

After electrical filtering to remove the echo at the excitation frequency, the difference-frequency echo can be captured by an oscilloscope. Intensity of the difference-frequency signal is extracted in the time window that corresponds to the depth of the intersection of the two excitation beams. By scanning the position of the sample using a motorized stage 408, the excitation voxel is scanned within the sample.

In other arrangements, the positions and/or directions of the excitation beams are scanned in order to scan the excitation voxel within the sample. The positions and/or directions of the excitation beams may be scanned by scanning one or both of the transducers 402 and 404, by beam steering, or by combinations of these and other methods, as examples. If desired, the return signal transducer 406 can be scanned, by moving the transducer 406 and/or through beam steering, to focus the return signal transducer 406 on the excitation voxels as the sample is scanned. By analyzing the detected signal as a function of the sample position, an image can be formed.

Figure 17A:
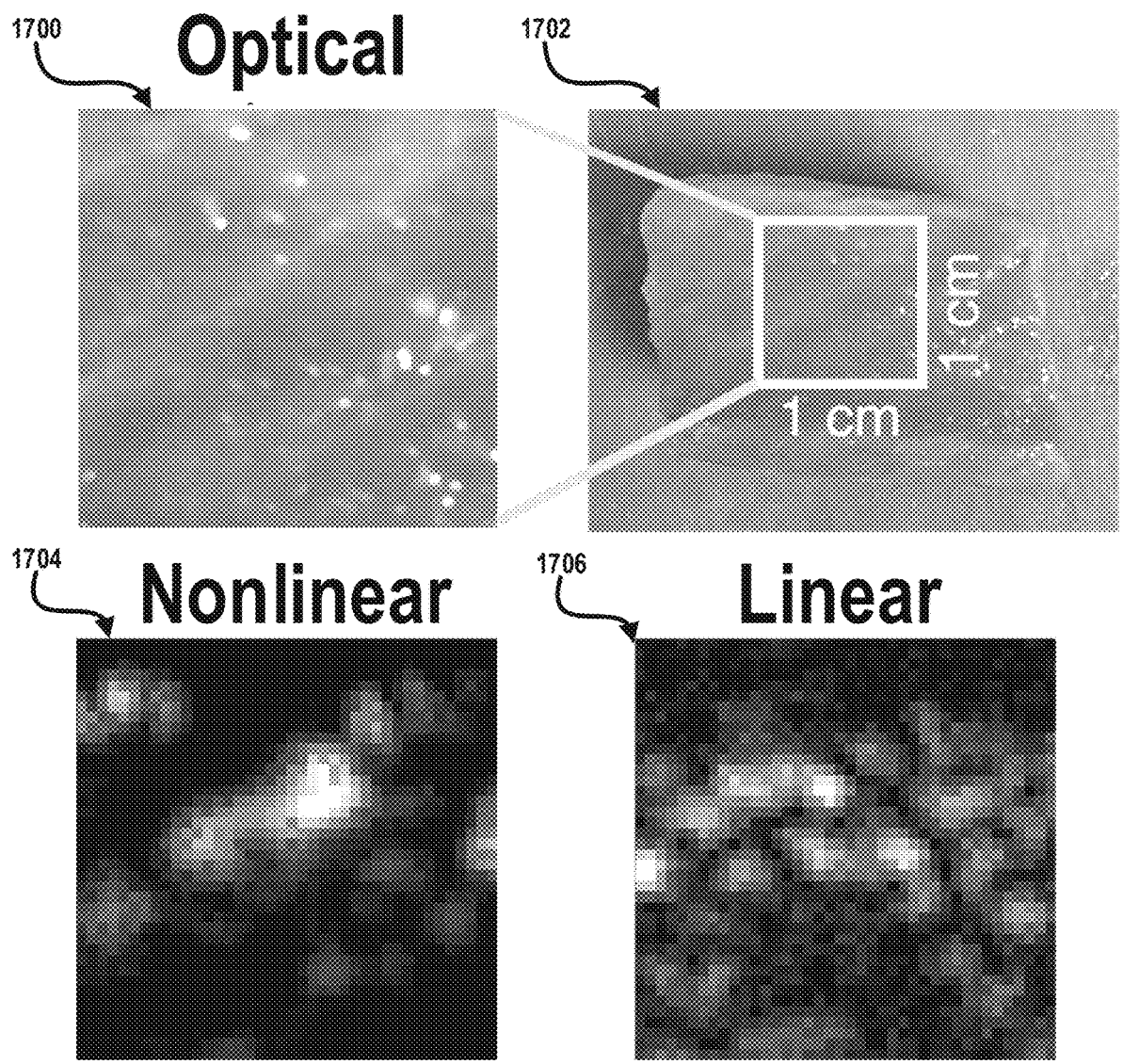
FIG. 17A illustrates optical images of a piece of salmon tissue, a linear ultrasonic image of the salmon tissue, and a nonlinear ultrasonic image of the salmon tissue according to an embodiment of the disclosed technology.

FIG. 17A illustrates the performance of the prototype system 1600 of FIG. 16 using salmon tissue as a sample target. FIG. 17A includes an optical image 1700 of the salmon tissue used as a sample target, an optical image 1702 zoomed in on a 1 cm by 1 cm portion of the sample, a nonlinear image 1704 of the 1 cm by 1 cm portion obtained using the techniques described herein (e.g., using the prototype system 1600 of FIG. 16 and the techniques described with reference to FIGS. 13A and 13B), and a linear image 1706 of the 1 cm by 1 cm portion obtained using conventional B mode ultrasonic imaging techniques. As shown in FIG. 17A, the nonlinear acoustic imaging method is both effective in suppressing speckle and in improving the image contrast of the fat layers in the salmon tissue (see, e.g., the improvement in nonlinear image 1704 relative to linear image 1706).

Figure 17B:
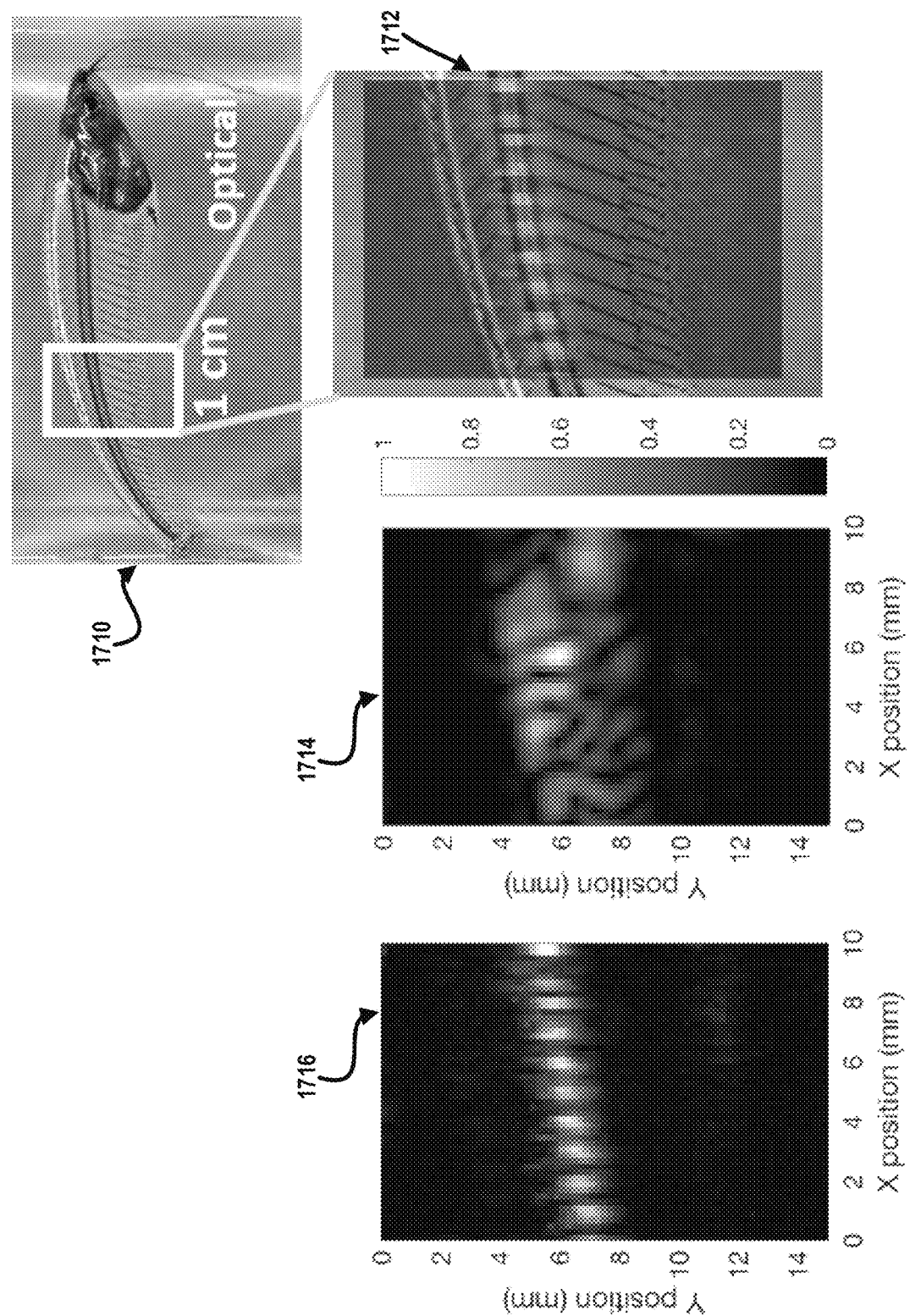
FIG. 17B illustrates optical, linear ultrasound, and nonlinear ultrasound images of a fish with bones.

FIG. 17B illustrates the performance of the prototype system 1600 of FIG. 16 using a fish as a sample target. FIG. 17B includes an optical image 1710 of the fish used as a sample target, an optical image 1712 zoomed in on a 1 cm×1 cm portion of the sample, a linear image 1714 of the 1 cm×1 cm portion, and a nonlinear image 1716 of the 1 cm×1 cm portion obtained using the techniques described herein (e.g., using the prototype system 1600 of FIG. 16 and the techniques of FIGS. 13A and 13B). As shown in FIG. 17A, the nonlinear acoustic imaging method is both effective in suppressing speckle and in improving the image contrast of the bones of the fish (see, e.g., the improvement in nonlinear image 1716 relative to linear image 1714).

In addition to dramatically improving the image clarity by reducing the speckle noise, the resolution remains defined by the shorter wavelength of the excitation frequencies. The new method can also improve the diffraction limit.

Figure 18:
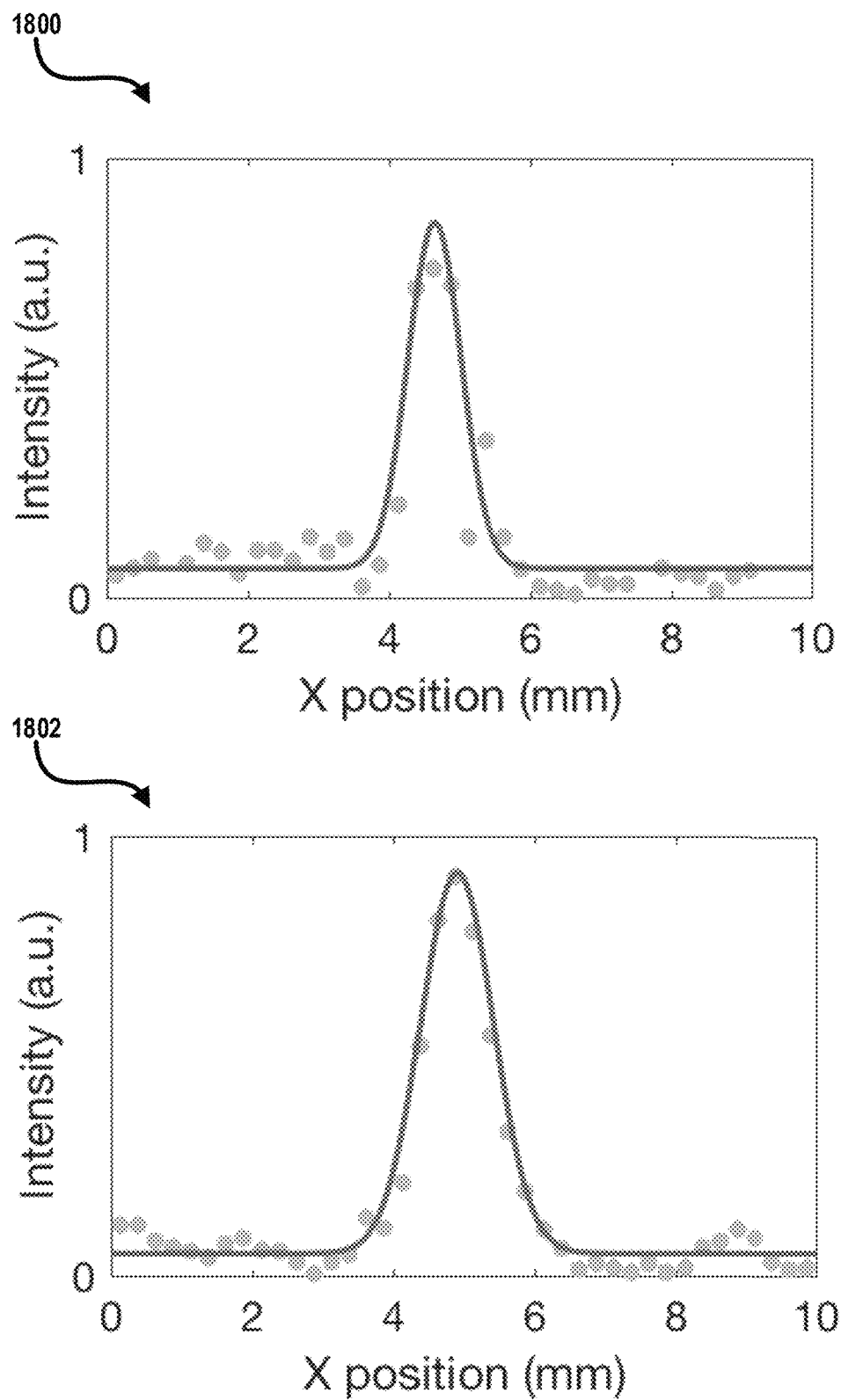
FIG. 18 illustrates graphs of a first line scan obtained using a nonlinear ultrasonic scan and a second line scan obtained using a linear ultrasonic scan according to an embodiment of the disclosed technology.

FIG. 18 illustrates two line scans 1800 and 1802 obtained using a nonlinear method in accordance with an embodiment and a conventional linear method, respectively. The line scans 1800 and 1802 are of a fish bone tip with a lateral dimension of ~0.2 mm, which may be significantly smaller than the imaging resolution. As a result, the widths of the line scans 1800 and 1802 correspond to the diffraction limited resolution of the two methods. The full-width at half maximum of the nonlinear method shown in scan 1800 is measured to be 0.89 mm and the full-width at half maximum of the linear method shown in scan 1800 is measured to be 1.22 mm. A resolution enhancement of a factor of 1.4 times is demonstrated from the ratio of the two values.

Figure 19:
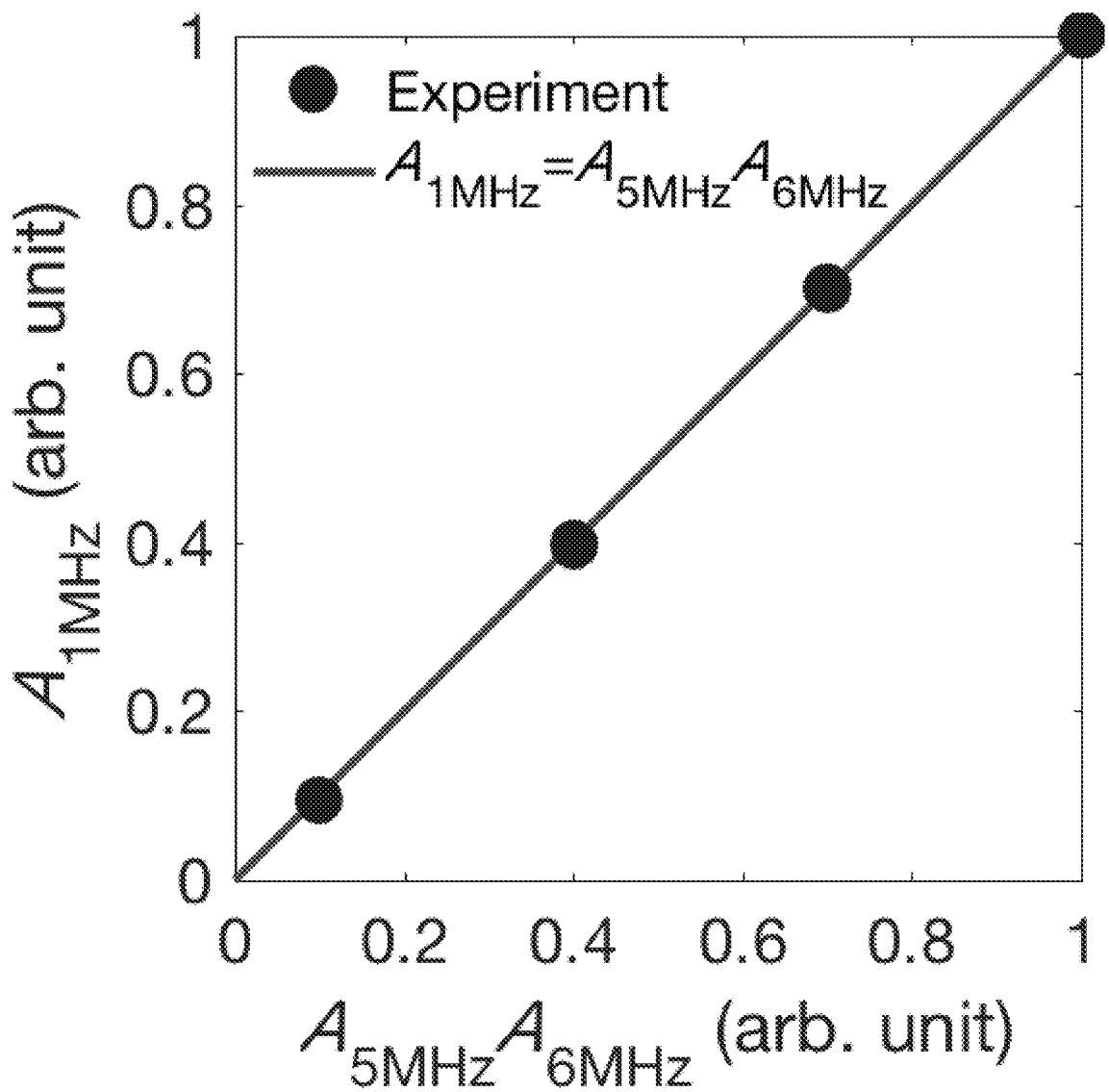
FIG. 19 illustrates a graph of the amplitude of a difference frequency signal as a function of the product of the amplitudes of two intersecting ultrasonic beams according to an embodiment of the disclosed technology.

The resolution enhancement results in part from the amplitude of the difference-frequency signal being proportional to the product of the linear amplitudes of the two excitation pulses. In particular, this relationship is shown in the graph of FIG. 19, which illustrates the amplitude of the difference frequency signal as a function of the product of the amplitudes of the two intersecting excitation beams. Because of this relationship, the amplitude of the difference-frequency signal decays faster away from the focal point as compared to the individual excitations (e.g., as compared to ultrasound utilizing a single excitation beam). In other words, the difference frequency signal is highly concentrated at the region of intersection of the individual excitation beams and falls off sharply away from the region of intersection. This effect increases the effective resolution of the system. The same mechanism also accounts for the improved resolution in harmonic imaging modes.

In addition to the improvement factors discussed above, the nonlinear ultrasound imaging system can utilize shorter wavelength (i.e., higher frequency) excitation beams than comparable linear ultrasound imaging systems. As a result, the nonlinear ultrasound imaging systems disclosed herein may have improved resolution. In particular, the attenuation rate (e.g., dB per centimeter of depth) of typical ultrasound targets, such as various body parts in medical ultrasounds, generally increases with higher frequencies. Thus, a typical linear ultrasound imaging system imaging a patient's liver needs to image to an approximately 20 cm depth. At a typical ultrasound frequency of 2.5 MHz, a patient's abdomen absorbs ultrasound at a rate of 2.2 dB per centimeter for a total one-way reduction of 44 dB reduction (e.g., an efficiency of 0.63%) at 20 centimeters of depth. Since the return signal in linear ultrasound systems is at the excitation frequency, the return signal also experiences a one-way reduction of 44 dB. As a result, the total loss is about 88 dB (e.g., an efficiency of $4\times10^{-5}$)

With the nonlinear ultrasound systems disclosed herein, the return signal may be at a significantly lower frequency. If, as an example, the return signal is at 0.8 MHz, the absorption rate for the abdomen drops to 0.6 dB per cm or 12 dB total (e.g., an efficiency in transmission of 0.25%). Assuming that the total loss remains at 88 dB, the significantly lower absorption rate for the return signal means that the system can tolerate a significantly higher absorption rate for the excitation signals. Continuing the previous example, the system could tolerate a 76 dB loss in the excitation signals (e.g., 88 dB total loss less the 12 dB return loss). Because of this higher tolerance, the system can utilize even higher excitation frequencies (than the linear systems at 2.5 MHz), such as 4 MHz. In general, resolution and penetration depth scale with the input frequencies. Thus, the nonlinear systems, utilizing higher excitation frequencies enabled by the lower absorption rate of the relatively low frequency return signal, may have a resolution improvement of about a factor of 1.6 over linear systems. In at least some embodiments, the nonlinear systems may have an expected resolution of about 440 micrometers when the lower frequency excitation beam is at 4 MHz.

XII. Simulated Acoustic Fields for a Nonlinear Ultrasound System

Figure 21:
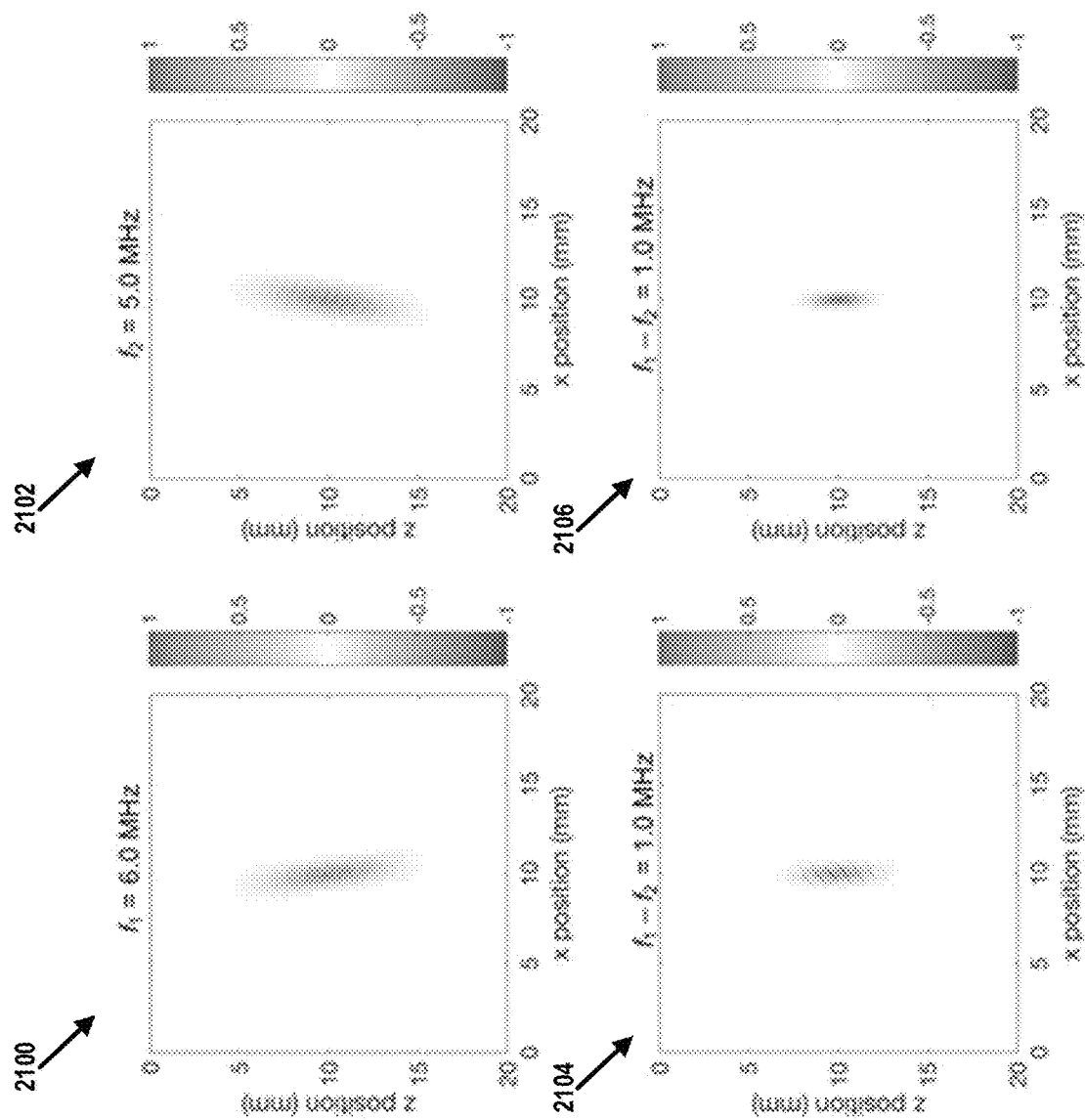
FIG. 21 illustrates graphs of simulated acoustic fields for a first of the intersecting beams of FIG. 13A, a second of the intersecting beams of FIG. 13A, nonlinear emission from an intersection voxel, and the spatial distribution of the intensity of the nonlinear emission according to an embodiment of the disclosed technology.

FIG. 21 shows the computer simulated acoustic fields for the two excitation pulses (plots 2100 and 2102), and the nonlinear emission from the intersection voxel (plot 2104). The simulation uses $f_1=6.0$ MHz and $f_2=5.0$ MHz for the two excitation pulses and the angle between their directions of propagation is 15°. $\Delta f=0.1$ MHz is used. The transverse dimension of the nonlinear voxel is smaller than the excitation pulses by a factor of about 1.4. The longitudinal dimension of the nonlinear voxel is larger than the transverse dimension by about 4 times. Increasing the angle between the two pulses can improve the longitudinal resolution. Plot 2106 shows the spatial distribution of the intensity of the nonlinear emission.

XIII. A Nonlinear Ultrasound System

Figure 22:
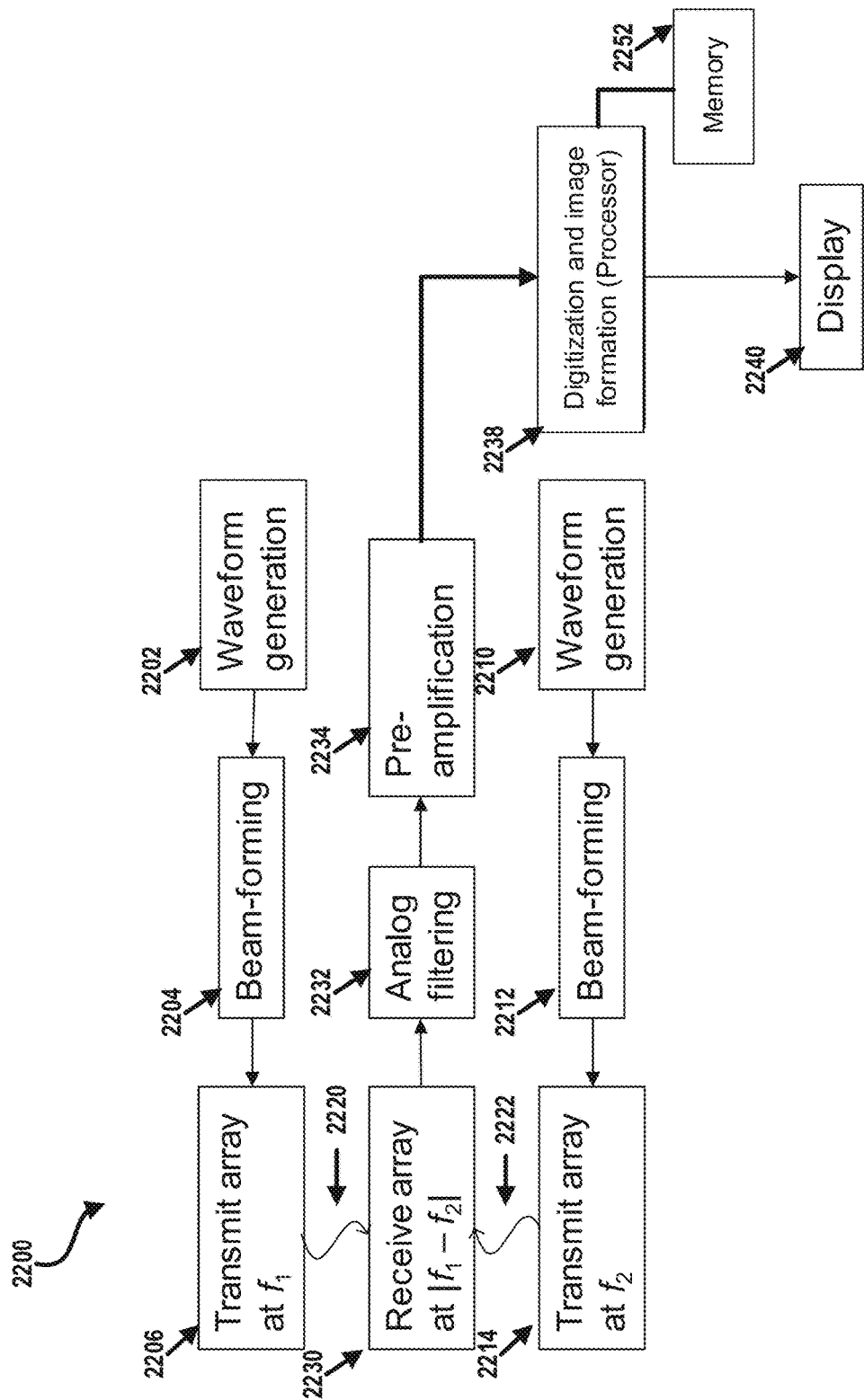
FIG. 22 is a block diagram of a system for nonlinear ultrasonic imaging according to an embodiment of the disclosed technology.

FIG. 22 is a schematic block diagram of ultrasound imaging system 2200. The ultrasound imaging system 2200 can generate ultrasound images with nonlinear contrast and reduced speckle. The system 2200 includes transducers including transmit arrays 2206 and 2214 and receive array 2230. The system also includes a processing circuit, such as processor 2238, arranged to generate an ultrasound image based on echoes received at the receive array 2230.

The processing circuit, which may be a processor, can generate ultrasound images in accordance with any suitable principles and advantages discussed herein. The processing circuit can perform a variety of signal processing functions such as frequency compounding, spatial compounding, voxel differentiation, filtering, or any other suitable processing functions for generating an ultrasound signal from received echoes. The processing circuit can include any suitable circuitry arranged to perform such signal processing. As illustrated, the processing circuit may include an analog filtering circuit 2232, a pre-amplification component 2234, and a digitization and image formation component 2238. The processing circuitry may also include waveform generation components 2202 and 2210 and beam-forming components 2204 and 2212.

The system 2200 can include one or more waveform generation components, such as wave form generation components 2202 and 2210. The waveform generation components 2202 and 2210 can generate the excitation signals used in exciting nonlinear emissions from voxels of an object being imaged by the system 2200. The excitation signals used to generate the A and A* beams are shown in FIG. 13A as an example. The waveform generators 2202 and/or 2210 can be used to generate a frequency modulated ultrasound signal (e.g., to facilitate distinguishing adjacent voxels, to facilitate frequency compounding, etc.). As one example, waveform generation component 2202 may generate excitation waveforms for the A beam of FIG. 13A, while waveform generation component 2210 may generate excitation waveforms for the A* beam of FIG. 13A.

Beam-forming components 2204 and 2212 can apply beam-forming to the waveforms generated by components 2202 and 2210, respectively. As an example, beam-forming components 2204 and 2212 can cause the resulting A and A* beams to be properly steered such that the beams intersect and excite the desired voxels as a function of time.

Beam-forming is a technique used with antenna arrays for transmitting or receiving signals with a controllable directionality. The direction of signals transmitted by an array (or the sensitivity of the array to signals from a particular direction) is altered by adjusting signal delays for the various antenna elements that form the array, such that signals transmitted at or receive from desired angles experience constructive interference and signals outside those desired angles experience destructive interference. Beam-forming may be accomplished via hardware or software (e.g., by adjusting hardware delay elements or by delaying signals for particular antenna elements via software).

Transmit arrays 2206 and 2214 can receive the beam-formed waveforms and transmit the excitation pulses into a medium being imaged by the system 2200, as shown schematically by pulses 1020 and 1022. Transmit array 2206 may transmit pulses at frequencies $f_1$ corresponding to the A beam of FIG. 13A, while transmit array 2214 may transmit pulses at frequencies $f_2$ corresponding to the A* beam of FIG. 13A.

Receive array 2230 can receive the nonlinear difference signal from the excited voxels. In particular, receive array 2230 may receive return signals at the difference frequency of the difference between $f_1$ and $f_1$.

Analog filtering circuit 2232 can filter the incoming signals from the receive array 2230. As examples, the analog filtering circuit 2232 may include low-pass, high-pass, and/or band-pass filters configured to reject or block linear echoes at the excitation frequencies $f_2$ and $f_2$, to reject or block harmonics of the excitation frequencies, to pass or accept signals at the difference frequency and to apply any other desired filtering.

Pre-amplification component 2234 may amplify the incoming signals from the analog filtering circuit 2232.

Digitization and image formation component 2238 may digitize the incoming signals from the receive array 2230 and can integrate or combine signals received over time into an ultrasound image. The digitization and image formation component 2238 may include a receive beam-forming component that uses beam-forming techniques to focus on a particular voxel or region of the object being imaged by the system 2200. In at least some embodiments, receive beam-forming can be performed digitally (e.g., after digitization of the incoming signals, but before image formation). In at least some other embodiments, receive beam-forming may be performed on incoming analog signals prior to digitization. The ultrasound image created by component 2238 may be a B-mode ultrasound image generated from the nonlinear signals of individual voxels. In at least some embodiments, component 2238 may be a processor configured with software to digitize incoming signals and combine those signals into an ultrasound image. Component 2238 may be coupled to memory 2252.

Display 2240 can visually present or otherwise provide the ultrasound image formed by component 2238 to a user. The display 2240 can be any suitable display arranged to visually present an ultrasound image, such as any of the ultrasound images shown in the drawings.

The nonlinear ultrasound imaging system 2200 may include memory 2252. Memory 2252 may store constructed images, processing results, transmit and receive control instructions, beamforming parameters, and software instructions, as examples.

XIV. Example Results for Nonlinear Contrast Ultrasound System

Figure 23:
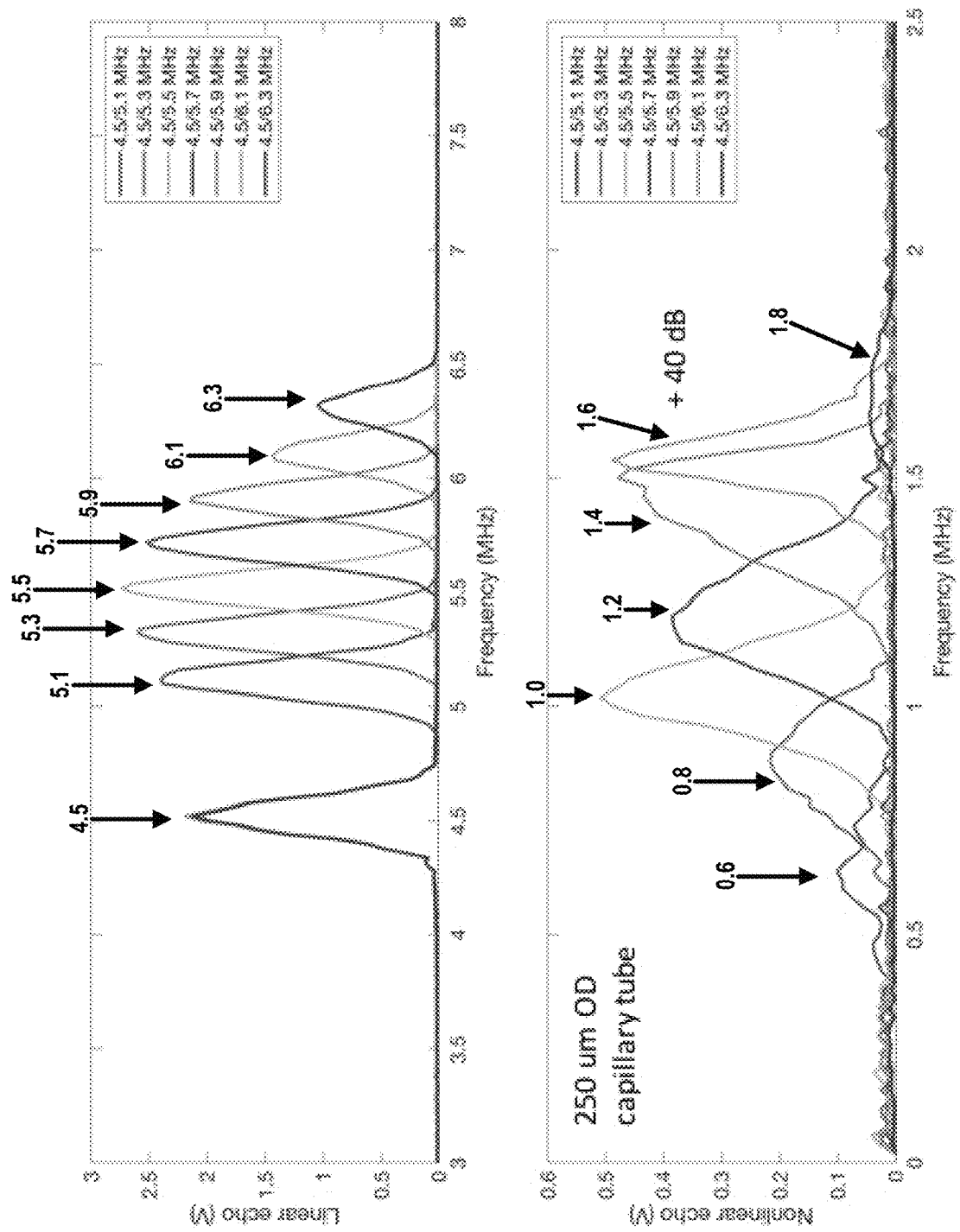
FIG. 23 shows the spectra of the excitation Gaussian pulses (linear echo) and the spectra of the nonlinear signal (nonlinear echo) according to an embodiment of the disclosed technology.

FIG. 23 illustrates the spectrum of the excitation Gaussian pulses and of the nonlinear return signals or echoes obtained using the prototype system 1600 of FIG. 16, for combinations of various excitation pulse frequencies, on a capillary tube having a 250 micrometer outer diameter. The center frequency of the nonlinear echo is shown to be centered around the difference of the center frequencies of the excitation pulses. The spectral line shape of the difference frequency echo is affected by the response function of the receiving transducer. The modifications are primarily modulations of the overall amplitudes, as the bandwidth of the nonlinear signal is about 5 times smaller than the bandwidth of the transducer. More subtle modifications of the line shape can be seen due to the variation of the receiving transducer response within the bandwidth of the nonlinear pulse.

FIG. 23 illustrates excitation pulses and nonlinear return signals with a first excitation beam at 4.5 MHz intersecting with a second excitation beam at 0.2 MHz steps from 5.1 MHz to 6.3 MHz. Thus, FIG. 23 illustrates the excitation pulses at the first excitation frequency of 4.5 MHz (see, e.g., the overlapping peaks at 4.5 MHz) and at each of the variations of the second excitation frequency (e.g., 5.1 MHz to 6.3 MHz in 0.2 MHz steps) and also illustrates the nonlinear return signals at the difference frequencies of 0.6 MHz, 0.8 MHz, 1.0 MHz, 1.2 MHz, 1.4 MHz, 1.6 MHz, and 1.8 MHz. The nonlinear return signals are labeled according to the difference frequencies, namely 0.6, 0.8, 1.0, 1.2, 1.4, 1.6, and 1.8, while the excitation pulses are labeled according to their respective frequencies.

Figure 24:
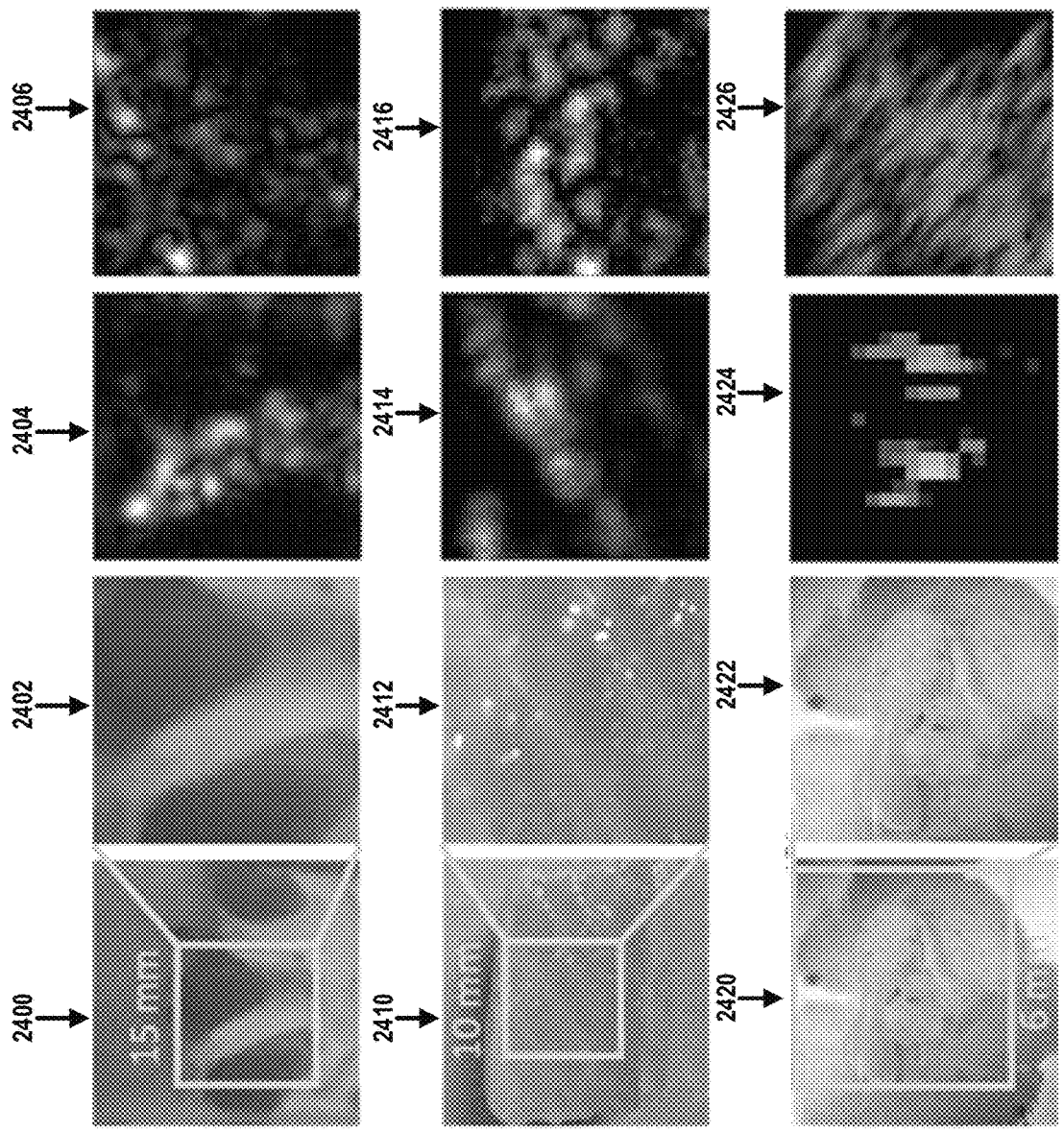
FIG. 24 illustrates optical images of a pig kidney, salmon tissue, and a mouse brain, linear contrast ultrasonic images of the same, and nonlinear contrast ultrasonic images of the same according to an embodiment of the disclosed technology.

FIG. 24 illustrates example results obtained using a nonlinear contrast ultrasound system. As shown in FIG. 24, the system was used to image a portion of a pig kidney, a portion of salmon tissue, and a mouse brain. FIG. 24 shows that nonlinear contrast images in accordance with the principles and advantages discussed herein can provide clearer ultrasound images than corresponding linear contrast ultrasound images.

Image 2400 is an optical image of the pig kidney sample and an enlarged optical image focused on a 1.5 cm by 1.5 cm section of the pig kidney sample is shown in image 2402. The nonlinear contrast ultrasound system was used to obtain the nonlinear image 2404 of the 1.5 cm by 1.5 cm section of pig kidney. In nonlinear image 2404, the minor calyx is clearly seen. In contrast, the minor calyx is unidentifiable in the linear contrast image 2406.

Image 2410 is an optical image of the salmon tissue sample and an enlarged optical image focused on a 1.0 cm by 1.0 cm section of the salmon tissue is shown in image 2412. The nonlinear contrast ultrasound system was used to obtain the nonlinear image 2414 of the 1.0 cm by 1.0 cm section of salmon tissue. In nonlinear image 2414, the fat layers in the salmon tissue are visible, while these fat layers are not visible over noise in the linear contrast image 2416.

Image 2420 is an optical image of the mouse brain sample, which includes a millimeter sized glioblastoma tumor, and an enlarged optical image focused on a 0.6 cm by 0.6 cm section of the mouse brain is shown in image 2422. The nonlinear contrast ultrasound system was used to obtain the nonlinear image 2424 of the 0.6 cm by 0.6 cm section of mouse brain. In nonlinear image 2424, the millimeter sized glioblastoma tumors are visible, while these tumors are not visible over noise in the linear contrast image 2426.

XV. Imaging Fluid Flows in a Nonlinear Ultrasound Imaging System

Figure 26C:
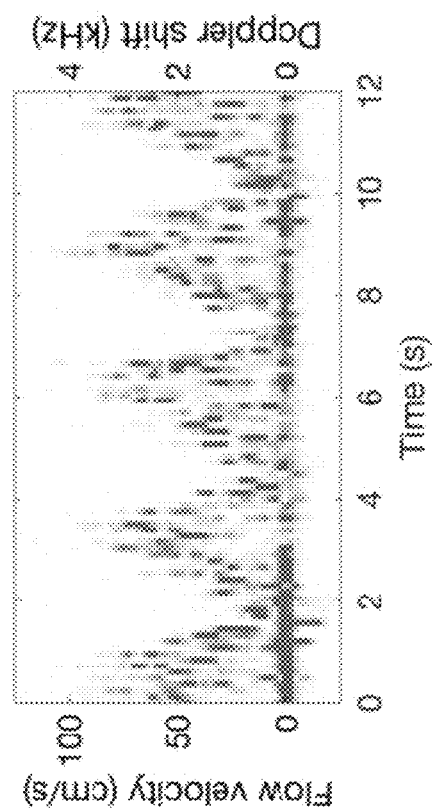
FIG. 26C is a graph of flow velocity over time as measured using a nonlinear ultrasound imaging system according to an embodiment of the disclosed technology.

The nonlinear ultrasound imaging systems and methods disclosed herein can be used in imaging fluid flows, such as blood flow in a patient. When imaging fluid flows, the nonlinear return signal is subjected to a Doppler shift, due to the motion of the fluid, given by $\Delta f_{Doppler} = (f_1 - f_2) + (\Delta f_{1D} + \Delta f_{2D})$, where $\Delta f_{1D}/f_1 = (v_{blood\ flow}/v_{sound}) \cos \theta$, as shown in FIG. 26A. The geometrically defined voxel may also be free from the aliasing artifact in the conventional pulse width and color Doppler.

Figure 26B:
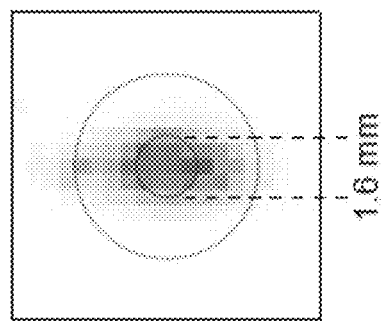
FIG. 26B illustrates a nonlinear ultrasonic image of fluid flow through tubing according to an embodiment of the disclosed technology.
Figure 26A:
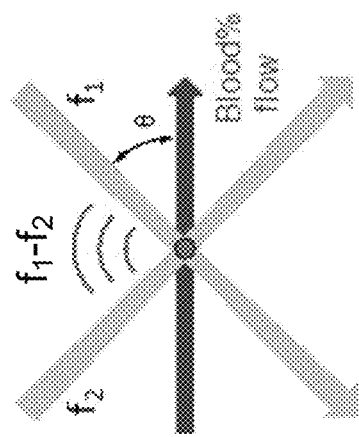
FIG. 26A is a diagram associated with a nonlinear ultrasound imaging system measuring fluid flow according to an embodiment of the disclosed technology.

In one example, a micro-bubble contrast agent (in particular, SonoVue from Bracco Inc.) at a diluted concentration allowed by the FDA was used to enhance a nonlinear signal in a blood flow through tubing (having a 1.6 mm inner diameter) and the nonlinear ultrasound imaging system was used to obtain the nonlinear image shown in FIG. 26B depicting the spatial distribution of the nonlinear Doppler signal intensity. As shown in FIG. 26B, the image is consistent with the expected image from the moving bubbles confined within the tubing and the image shows a spatial resolution of 0.75 mm by 1.2 mm.

The Doppler shift (right y-axis) and corresponding flow velocity (left y-axis) as a function of time (x-axis) at the center of the tubing is shown in FIG. 26C. When capturing the image of FIG. 26C, the flow velocity was modulated at a frequency of about ⅓ Hz. When measuring blood flow in a live animal or patient, the signal acquisition can be synchronized with breathing and heartbeat to reduce motion artifacts. The direct measurement of blood flow at the locations of regions of interest, such as partial coronary blockages throughout the heart, may be non-invasively imaged at high levels of quality with the nonlinear ultrasound imaging systems provided herein.

XVI. A Method of Nonlinear Imaging

Figure 27:
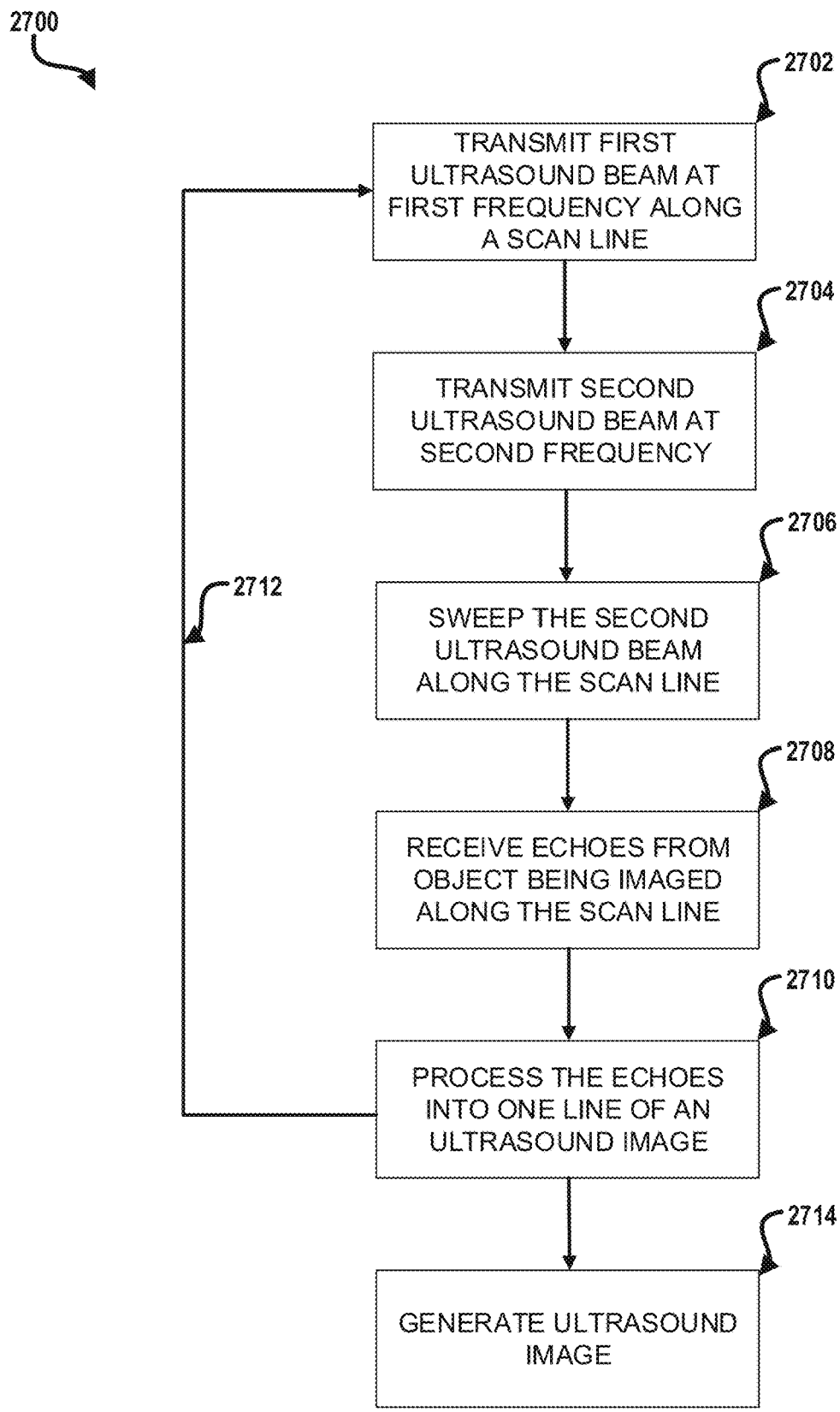
FIG. 27 is a flowchart of a method of nonlinear ultrasound imaging according to an embodiment of the disclosed technology.

FIG. 27 is a flowchart of method 2700 of nonlinear imaging according to an embodiment of the disclosed technology.

In block 2702, method 2700 transmits a first ultrasound beam at a first frequency along a scan line (e.g., transmits one or more ultrasound pulses in the A beam along a given scan line in the B-scan sweep, as depicted in FIG. 13A).

In block 2704, method 2700 transmits a second ultrasound beam at a second frequency. As an example, block 2704 may involve transmitting one or more ultrasound pulses in the A* beam. The pulses transmitted in block 2704 may be timed to intersect with corresponding pulses of the A beam at one or more voxels being imaged, as depicted in FIG. 13A.

In block 2706, method 2700 sweeps the second ultrasound beam along the scan line of the first ultrasound beam. As an example, block 2706 may involve sweeping the A* beam along the scan line of the A beam (e.g., along the current scan line of the B-scan sweep) as illustrated in FIG. 13A.

In block 2708, method 2700 receives echoes along the scan line from the object being imaged. The echoes may result from nonlinear interactions of the first and second scan beams and may have a frequency equal to the difference of the first and second frequency.

In block 2710, method 2700 processes the echoes into one line of an ultrasound image (e.g., a B-scan image).

As indicated by arrow 2712, blocks 2702-2710 may be repeated for multiple scan lines. In particular, the A beam may be swept along the B-scan sweep direction 1310, as illustrated in FIG. 13A, and the A* beam may be adjusted to continue to sweep along the new scan lines of the A beam. In this manner, each of the lines of a B-mode image can be obtained.

In block 2714, method 2700 combines the lines of the ultrasound image, obtains via multiple iterations of blocks 2702-2710, into an ultrasound image, such as a B mode image. The B mode image may be stored in memory or storage and may be displayed or otherwise provided to a user.

In at least some embodiments, the blocks of method 2700 may be performed at least partially in parallel. As an example, blocks 2702, 2704, and 2706 may be performed substantially in parallel such that the transmitted pulses in the first and second ultrasound beams intersect in time and space at the desired voxels being imaged, for example, as depicted in FIG. 13A. Similarly, blocks such as block 2708 and 2710 can be performed substantially in parallel, but delayed with respect to blocks 2702, 2704, and 2706 to account for the round-trip time of the ultrasound beams to and from the voxels being imaged.

XVII. Conclusion

While certain embodiments have been described, these embodiments have been presented by way of example only, and are not intended to limit the scope of the disclosure. Indeed, the novel devices, systems, apparatus, and methods described herein may be embodied in a variety of other forms. The principles and advantages of the embodiments can be used for any other suitable devices, systems, apparatuses, and/or methods that could benefit from such principles and advantages. Furthermore, various omissions, substitutions and changes in the form of the methods and systems described herein may be made without departing from the spirit of the disclosure. All possible combinations and sub combinations are intended to fall within the scope of this disclosure. For example, while blocks are presented in a given arrangement, alternative embodiments may perform similar functionalities with different components and/or circuit topologies, and some blocks may be deleted, moved, added, subdivided, combined, and/or modified. Each of these blocks may be implemented in a variety of different ways. As another example, methods discussed herein can be performed in any suitable order. Any suitable combination of the elements and acts of the various embodiments described above can be combined to provide further embodiments.

What is claimed is:

1. A method of ultrasound imaging with frequency compounding for speckle reduction, the method comprising:
    applying a drive signal to a transducer array so that the transducer array is excited and transmits a broadband ultrasound signal into a medium being imaged, wherein a frequency response of the transducer array comprises a peak response frequency at a first frequency, wherein a frequency spectrum of the drive signal comprises a peak drive frequency at a second frequency, different than the first frequency, in order to compensate for the peak response frequency of the frequency response of the transducer array so that the broadband ultrasound signal resulting from excitation of the transducer array by the drive signal comprises a flattened spectrum across a bandwidth of the transducer array;
    receiving echoes of the broadband ultrasound signal from the medium;
    frequency filtering, with a plurality of digital filters, the received echoes to produce a plurality of ultrasound images; and
    generating a frequency-compounded ultrasound image by compounding the ultrasound images.

2. The method of claim 1, further comprising:
    generating a plurality of additional frequency-compounded ultrasound images;
    forming a B-mode scan from the additional frequency compounded ultrasound images and the frequency-compounded ultrasound image; and
    outputting a representation of the B-mode scan.

3. The method of claim 1, wherein the transmitting of the broadband ultrasound signal comprises transmitting the broadband ultrasound signal with a phased array that focuses the broadband ultrasound signal on at least one voxel within the medium being imaged.

4. The method of claim 1, further comprising:
    Fourier transforming the received echoes, wherein the frequency filtering is performed on the Fourier transformed received echoes; and
    inverse Fourier transforming the ultrasound images to the time domain after the frequency filtering.

5. The method of claim 4, wherein the time domain signals are used to produce the frequency-compounded ultrasound image.

6. The method of claim 1, wherein the receiving of the echoes comprises receiving the echoes with a phased array configured to focus on at least one voxel within the medium being imaged.

7. The method of claim 1, wherein the transmitting of the broadband ultrasound signal comprises transmitting the broadband ultrasound signal with a first phased array that focuses the broadband ultrasound signal at a at least one voxel within the medium being imaged, and the receiving of the echoes comprises receiving the echoes with a second phased array configured to focus on at least one voxel within the medium being imaged.

8. The method of claim 7, wherein the first and second phased array each comprise a plurality of array elements and wherein the array elements of the first phased array are interleaved with the array elements of the second phased array.

9. The method of claim 1, wherein the frequency-compounded ultrasound image is a nonlinear ultrasound image.

10. The method of claim 1, wherein the plurality of digital filters comprises Gaussian filters.

11. The method of claim 1, wherein the generating the frequency-compounded ultrasound image comprises averaging the ultrasound images.

12. A method of ultrasound imaging with frequency compounding for speckle reduction, the method comprising:
    transmitting a pulse of a broadband ultrasound signal comprising a substantially flat spectrum from a transducer in a medium being imaged, wherein the transmitting of the broadband ultrasound signal results from applying a drive signal to the transducer so as to excite the transducer, wherein a frequency response of the transducer comprises a peak response frequency at a first frequency, wherein a frequency spectrum of the drive signal comprises a peak drive frequency at a second frequency, different than the first frequency, in order to compensate for the peak response frequency of the frequency response of the transducer so that the broadband ultrasound signal comprises the substantially flat spectrum;

receiving echoes of the broadband ultrasound signal from a plurality of depths within the medium;

frequency filtering the received echoes to produce a plurality of A-scan speckle images, wherein each A-scan speckle image is obtained from the pulse of the broadband ultrasound signal and comprises independent speckle relative to the other A-scan speckle images; and generating an A-scan frequency-compounded ultrasound image by compounding the A-scan speckle images together to reduce speckle.

13. The method of claim 12 further comprising:
repeating the transmitting, receiving, frequency filtering, and generating steps to generate a plurality of A-scan frequency-compounded ultrasound images; and
combining the plurality of A-scan frequency-compounded ultrasound images to form a B-mode frequency-compounded ultrasound image of the medium being imaged.

14. The method of claim 12, wherein the transmitting of the broadband ultrasound signal comprises transmitting the broadband ultrasound signal with a phased array that focuses the broadband ultrasound signal on at a at least one voxel within the medium being imaged.

15. The method of claim 12, wherein the receiving of the echoes comprises receiving the echoes with a phased array configured to focus on at least one voxel within the medium being imaged.

16. The method of claim 12, wherein the transmitting of the broadband ultrasound signal comprises transmitting the broadband ultrasound signal with a first phased array that focuses the broadband ultrasound signal at a at least one voxel within the medium being imaged, wherein the receiving of the echoes comprises receiving the echoes with a second phased array configured to focus on at least one voxel within the medium being imaged.

17. The method of claim 16 wherein the first and second phased array each comprise a plurality of array elements and wherein the array elements of the first phased array are interleaved with the array elements of the second phased array.

18. A method of ultrasound imaging with frequency compounding for speckle reduction, the method comprising:
transmitting a broadband ultrasound signal from a transducer in a medium being imaged, wherein the transmitting of the broadband ultrasound signal results from applying a drive signal to the transducer so as to excite the transducer, wherein a frequency response of the transducer comprises a peak response frequency at a first frequency, wherein a frequency spectrum of the drive signal comprises a peak drive frequency at a second frequency, different than the first frequency, in order to compensate for the peak response frequency of the frequency response of the transducer and cause the transmitted broadband ultrasound signal to comprise a substantially flat spectrum;

receiving echoes of the broadband ultrasound signal from a plurality of depths within the medium;

Fourier transforming the received echoes;

frequency filtering the Fourier transformed received echoes to produce a plurality of frequency-domain speckle images;

inverse Fourier transforming the speckle images to produce a plurality of time-domain speckle images, each time-domain speckle image having independent speckle relative to the other time-domain speckle images; and generating a frequency-compounded ultrasound image by compounding the speckle images together.

19. The method of claim 18, wherein the plurality of time-domain speckle images having independent speckle arc obtained using a single pulse of the transmitted broadband ultrasound signal.

20. The method of claim 1, wherein the transmitted broadband ultrasound signal comprises a pulse of the broadband ultrasound signal, and wherein each of the plurality of ultrasound images is obtained from the pulse of the broadband ultrasound signal and has independent speckle relative to the other ultrasound images.

* * * * *